(12) United States Patent
Collins et al.

(10) Patent No.: US 7,618,632 B2
(45) Date of Patent: Nov. 17, 2009

(54) METHOD OF TREATING OR AMELIORATING AN IMMUNE CELL ASSOCIATED PATHOLOGY USING GITR LIGAND ANTIBODIES

(75) Inventors: Mary Collins, Natick, MA (US); Ethan Menahem Shevach, Rockville, MD (US); Rebecca Suzanne McHugh, Wellington (NZ); Matthew James Whitters, Hudson, MA (US); Deborah Ann Young, Melrose, MA (US); Michael Chapman Byrne, Brookline, MA (US); Padmalatha S. Reddy, Walpole, MA (US); Geoffrey Laurence Stephens, Damascus, MD (US); Beatriz M. Carreno, Acton, MA (US)

(73) Assignees: Wyeth, Madison, NJ (US); The United States of America as represented by the Secretary of the Department of Health and Human Services, Washington, DC (US)

(*) Notice: Subject to any disclaimer, the term of this patent is extended or adjusted under 35 U.S.C. 154(b) by 147 days.

(21) Appl. No.: 10/853,032

(22) Filed: May 24, 2004

(65) Prior Publication Data

US 2005/0014224 A1    Jan. 20, 2005

Related U.S. Application Data

(60) Provisional application No. 60/472,844, filed on May 23, 2003, provisional application No. 60/547,975, filed on Feb. 26, 2004.

(51) Int. Cl.
*A61K 39/395* (2006.01)
*C07K 16/00* (2006.01)
(52) U.S. Cl. ............................... 424/144.1; 530/388.22
(58) Field of Classification Search ...................... None
See application file for complete search history.

(56) References Cited

U.S. PATENT DOCUMENTS

| | | | |
|---|---|---|---|
| 5,593,972 A | 1/1997 | Weiner et al. | 514/44 |
| 5,624,821 A | 4/1997 | Winter et al. | 435/69.6 |
| 5,648,260 A | 7/1997 | Winter et al. | 435/252.3 |
| 5,714,147 A | 2/1998 | Capon et al. | 424/178.1 |
| 5,998,171 A | 12/1999 | Yu et al. | 435/69.5 |
| 6,077,673 A | 6/2000 | Chenchick et al. | 435/6 |
| 6,406,867 B1 | 6/2002 | Yu et al. | 435/7.2 |
| 6,506,559 B1 | 1/2003 | Fire et al. | 435/6 |
| 6,521,742 B2 | 2/2003 | Yu et al. | 530/351 |
| 2002/0146389 A1* | 10/2002 | Ashkenazi et al. | 424/85.1 |
| 2003/0133936 A1 | 7/2003 | Byrne et al. | 424/146.1 |

FOREIGN PATENT DOCUMENTS

WO    WO 98/24895    6/1998

OTHER PUBLICATIONS

Merrill JT. Emergence of targeted immune therapies for systemic lupus. Expert Opin. Emerging Drugs. 2005. vol. 10, No. 1, pp. 53-65.*
Galon J., et al. TNFSF1A mutations and autoinflammatory syndroms. Current Opinion in Immunology. 2000. vol. 12, p. 479-486.*
Arts et al. "Adenoviral Vectors Expressing siRNAs for Discovery and Validation of Gene Function" Genome Res. 13:2325-32 (2003).
Aseffa et al. "The Early IL-4 Response to *Leishmania major* and the Resulting Th2 Cell Maturation Steering Progressive Disease in BALB/c Mice are Subject to the control of Regulatory CD4(+)CD25(+) T Cells[1]" J. Immunol. 169:3232-41 (2002).
Banchereau and Steinman "Dendritic Cells and the Control of Immunity" Nature 392:245-52 (1998).
Bass "The Short Answer" Nature 411:428-29 (2001).
Belkaid et al. "CD4(+)CD25(+) Regulatory T cells Control *Leishmania major* Persistence and Immunity" Nature 420:502-07 (2002).
Bockamp et al. "Of Mice and Models: Improved Animal Models for Biomedical Research" Physiol. Genomics 11(3):115-32 (2002).
Brenne et al. "Interleukin-21 is a Growth and Survival Factor for Human Myeloma Cells" Blood 99(10):3756-62 (2002).
Cerundolo et al. "Dendritic Cells: A Journey from Laboratory to Clinic" Nat. Immunol. 5(1):7-10 (2004).
Chothia and Lesk "Canonical Structures for the Hypervariable Regions of Immunoglobulins" J. Mol. Biol. 196:901-17 (1987).
Claros and von Heijne "TopProd II: an improved software of membrane protein structure predictions" Comput. Appl. Biosci. 10:685-86 (1994).
Croft "Co-Stimulatory Members of the TNFR Family: Keys to Effective T-Cell Immunity" Nat. Rev. Immunol. 3:609-20 (2003).
Degermann et al. "On the Various Manifestations of Spontaneous Autoimmune Diabetes in Rodent Models" Eur. J. Immunol. 24:3155-66 (1994).
Desbarats et al. "Newly Discovered Role for Fas Ligand in the Cell-Cycle Arrest of CD4+ T Cells" Nat. Med. 4:1377-82 (1998).

(Continued)

*Primary Examiner*—Robert Landsman
*Assistant Examiner*—Bruce D Hissong
(74) *Attorney, Agent, or Firm*—Fitzpatrick Cella Harper & Scinto

(57) ABSTRACT

The present invention provides novel isolated and purified polynucleotides and polypeptides related to a novel ligand for glucocorticoid-induced TNF receptor (GITR). The invention also provides antibodies to the GITR ligand (GITRL). The present invention also is directed to novel methods for diagnosing, prognosing, monitoring the progress of, and treating disorders arising from disregulation of the immune system (e.g., autoimmune disorders, inflammatory diseases, and transplant rejection, and cancers and infectious diseases) using GITRL and/or modulators of GITRL. The present invention is further directed to novel therapeutics and therapeutic targets and to methods of screening and assessing test compounds for the intervention (treatment) and prevention of said disorders arising from disregulation of the immune system, as related to GITRL and GITR.

4 Claims, 25 Drawing Sheets

OTHER PUBLICATIONS

Dorn et al. "siRNA Relieves Chronic Neuropathic Pain" Nucleic Acids Res. 32(5):e49(pp. 1-6) (2004).

Elbashir et al. "Functional Anatomy of siRNAs for Mediating Efficient PNAi in *Drosophila melanogaster* Embryo Lysate" EMBO J. 20(23):6877-88 (2001).

Elbashir et al. "Duplexes of 21-Nucleotide RNAs Mediate RNA Interference in Cultured Mammalian Cells" Nature 411:494-98 (2001).

Galderisi et al. "Antisense Oligonucleotides as Therapeutic Agents" J. Cell. Physiol. 181:251-57 (1999).

Gavin et al. "Homeostasis and Anergy of CD4+CD25+ Suppressor T Cells In Vivo" Nat. Immunol. 3(1): 33-41 (2002).

Gilfillan et al. "Expression of the Costimulatory Receptor CD30 is Regulated by Both CD28 and Cytokines" J. Immunol. 160(5):2180-87 (1998).

Giulietti et al. "An Overview of Real-Time Quantitative PCR: Applications to Quantify Cytokine Gene Expression" Methods 25(4):386-401 (2001).

Gurney et al. "Identification of a New Member of the Tumor Necrosis Factor Family and Its Receptor, a Human Ortholog of Mouse GITR" Curr. Biol. 9(4):215-18 (1999).

Han et al. "Extracellular Matrix Protein 1 (ECM1) has Angiogenic Properties and is Expressed by Breast Tumor Cells" FASEB J. 15(6):988-94 (2001).

Heasman "Morpholino Oligos: Making Sense of Antisense?" Dev. Biol. 243(2):209-14 (2002).

Heid et al. "Real Time Quantitative PCR" Genome Res. 6(10):986-94 (1996).

Henikoff and Henikoff "Amino Acid Substitution Matrices from Protein Blocks" Proc. Natl. Acad. Sci. USA 89:10915-19 (1992).

Hisaeda et al. "Escape of Malaria Parasites from Host Immunity Requires CD4+CD25+ Regulatory T Cells" Nat. Med. 10(1):29-30 (2004).

Ji et al. "Cutting edge: the natural ligand for glucocorticoid-induced TNF receptor-related protein abrogates regulatory T cell suppression" J. Immunol. 172:5823-27 2004.

Jordan et al. "Thymic Selection of CD4+CD25+ Regulatory T Cells Induced by an Agonist Self-peptide" Nat. Immunol. 2(4):301-06 (2001).

Kim et al. "Cloning and Characterization of GITR Ligand" Genes Immun. 4:564-69 (2003).

Knauert and Glazer "Triplex Forming Oligonucleotides: Sequence-specific Tools for Gene Targeting" Hum. Mol. Genet. 10:2243-51 (2001).

Ko et al. "Immunotherapy of Malignant Diseases" Int. Arch. Allergy Immunol. 132(4):294-309 (2003).

Kumanogoh et al. "Increased T Cell Autoreactivity in the Absence of CD40-CD40 Ligand Interactions: A Role of CD40 in Regulatory T Cell Development" J. Immunol. 166:353-60 (2001).

Kursar et al. "Regulatory CD4+CD25+ T Cells Restrict Memory CD8+ T Cell Responses" J. Exp. Med. 196(12):1585-92 (2002).

Kuwana "Induction of Anergic and Regulatory T Cells by Plasmacytoid Dendritic Cells and Other Dendritic Cell Subsets" Hum. Immunol. 63:1156-63 (2002).

Kwon et al. "Identification of a Novel Activation-inducible Protein of the Tumor Necrosis Factor Receptor Superfamily and Its Ligand" J. Biol. Chem. 274(10):6056-61 (1999).

Lu and Thomson "Manipulation of Dendritic Cells for Tolerance Induction in Transplantation and Autoimmune Disease" Transplantation 73:S19-S22 (2002).

Lundgren et al. "Helicobacter Pylori-specific CD4+CD25(high) Regulatory T Cells Suppress Memory T-cell Responses to H. Pylori in Infected Individuals" Infect. Immun. 71(4):1755-62 (2003).

Maloy et al. "CD4+CD25+ T(R) Cells Suppress Innate Immune Pathology Through Cytokine-dependent Mechanisms" J. Exp. Med. 197(1):111-19 (2003).

Mancini et al. "The Management of Immunosuppression: The Art and The Science" Crit. Care. Nurs. Q. 27:61-64 (2004).

McHugh and Shevach "The Role of Suppressor T Cells in Regulation of Immune Responses" J. Allergy Clin. Immunol. 110:693-702 (2002).

McHugh et al. "CD4(+)CD25(+) Immunoregulatory T Cells: Gene Expression Analysis Reveals a Functional Role for the Glucocorticoid-induced TNF Receptor" Immunity 16:311-23 (2002).

Micklefield "Backbone Modification of Nucleic Acids: Synthesis, Structure and Therapeutic Applications" Curr. Med. Chem. 8:1157-79 (2001).

Mullah et al. "Efficient Synthesis of Double Dye-labeled Oligodeoxyribonucleotide Probes and their application in a Real Time PCR Assay" Nucleic Acids Res. 26(4)1026-31 (1998).

Nakano et al. "CD11c(+)B220(+)Gr-1(+) Cells in Mouse Lymph Nodes and Spleen Display Characteristics of Plasmacytoid Dendritic Cells" J. Exp. Med. 194(8):1171-78 (2001).

Nocentini et al. "A New Member of the Tumor Necrosis Factor / Nerve Growth Factor Receptor Family Inhibits T Cell Receptor-induced Apoptosis" Proc. Natl. Acad. Sci. USA 94:6216-21 (1997).

Oshima et al. "Characterization of Murine CD70 by Molecular Cloning and mAb" Int. Immunol. 10(4):517-26 (1998).

Ouyang et al. "Inhibition of Th1 Development Mediated by GATA-3 Through an IL-4-Independent Mechanism" Immunity 9:745-55 (1998).

Paddison et al. "Stable Suppression of Gene Expression by RNAi in Mammalian Cells" Proc. Natl. Acad. Sci. USA 99:1443-48 (2002).

Papiernik et al. "Regulatory CD4 T Cells: Expression of IL-2Rα Chain, Resistance to Clonal Deletion and IL-2 Dependency" Int. Immunol. 10(4):371-78 (1998).

Piccirillo and Shevach "Cutting Edge: Control of CD8+ T Cell Activation by CD4(+)CD25(+) Immunoregulatory Cells" J. Immunol. 167:1137-40 (2001).

Reynolds et al. "Rational siRNA Design for RNA Interference" Nat. Biotechnol. 22:326-30 (2004).

Riccardi et al. "Glucocorticoid Hormone-induced Modulation of Gene Expression and Regulation of T-cell Death: Role of GITR and GILZ, Two Dexamethasone-induced Genes" Cell Death Differ. 6:1182-89 (1999).

Rifle and Mousson "Dendritic Cells and Second Signal Blockade: A Step Toward Allograft Tolerance?" Transplantation 73:S1-S2 (2002).

Rogers et al. "OX40 Promotes BcI-xL and BcI-2 Expression and is Essential for Long-term Survival of CD4 T Cells" Immunity 15:445-55 (2001).

Ronchetti et al. "Role of GITR in Activation Response of T Lymphocytes" Blood 100:350-52 (2002).

Sakaguchi et al. "Immunologic Self-tolerance Maintained by Activated T Cells Expressing IL-2 Receptor α-Chains (CD25)" J. Immunol. 155:1151-64 (1995).

Salomon et al. "B7/CD28 Costimulation is Essential for the Homeostasis of the CD4(+)CD25(+) Immunoregulatony T Cells that Control Autoimmune Diabetes" Immunity 12:431-40 (2000).

Shevach "Regulatory T Cells in Autoimmmunity" Ann. Rev. Immunol. 18:423-49 (2000).

Shevach "Certified Professionals: CD4(+)CD25(+) Suppressor T Cells" J. Exp. Med. 193(11):F41-F45 (2001).

Shimizu et al. "Stimulation of CD25(+)CD4(+) Regulatory T Cells Through GITR Breaks Immunological Self-tolerance" Nat. Immunol. 3(2):135-42 (2002).

Sioud "Nucleic Acid Enzymes as a Novel Generation of Anti-gene Agents" Curr. Mol. Med. 1:575-88 (2001).

Song et al. "RNA Interference Targeting Fas Protects Mice from Fulminant Hepatitis" Nat. Med. 9:347-51 (2003).

Sui et al. "A DNA Vector-based RNAi Technology to Suppress Gene Expression in Mammalian Cells" Proc. Natl. Acad. Sci. USA 99:5515-20 (2002).

Suri-Payer et al. "Post-thymectomy Autoimmune Gastritis: Fine Specificity and Pathogenicity of anti-H/K ATPase-reactive T Cells" Eur. J. Immunol. 29:669-77 (1999).

Suri-Payer et al. "CD4(+)CD25(+) T Cells Inhibit Both the Induction and Effector Function of Autoreactive T Cells and Represent a Unique Lineage of Immunoregulatory Cells" J. Immunol. 160:1212-18 (1998).

Suvas et al. "CD4(+)CD25(+) T Cells Regulate Virus-specific Primary and Memory CD8+ T Cell Responses" J. Exp. Med. 198(6):889-901 (2003).

Takahashi et al. "Immunologic Self-tolerance Maintained by CD25+CD4+ Naturally Anergic and Suppressive T Cells: Induction of Autoimmune Disease by Breaking their Anergic/Suppressive State" Int. Immunol. 10(12)1969-80 (1998).

Takahashi et al. "Immunologic Self-tolerance Maintained by CD25+CD4+ Regulatory T Cells Constitutively Expressing Cytotoxic T Lymphocyte-associated Antigen 4" J. Exp. Med. 192(2):303-09 (2000).

Tamayo et al. "Interpreting Patterns of Gene Expression with Self-organizing Maps: Methods and Application to Hematopoietic Differentiation" Proc. Natl. Acad. Sci. USA 96:2907-12 (1999).

Thornton and Shevach "Suppressor Effector Function of CD4(+)CD25(+) Immunoregulatory T Cells is Antigen Nonspecific" J. Immunol. 164:183-90 (2000).

Thornton and Shevach "CD4(+)CD25(+) Immunoregulatory T Cells Suppress Polyclonal T Cell Activation In Vitro by Inhibiting Interleukin 2 Production" J. Exp. Med. 188(2):287-96 (1998).

Tone et al. "Mouse Glucocorticoid-induced Tumor Necrosis Factor Receptor Ligand is Costimulatory for T Cells" Proc. Natl. Acad. Sci. USA 100(25)15059-64 (2003).

Uraushihara et al. "Regulation of Murine Inflammatory Bowel Disease by CD25(+) and CD25(-31 ) CD4(+) Glucocorticoid-induced TNF Receptor Family-related Gene+ Regulatory T Cells" J. Immunol. 171:708-16 (2003).

Valmori et al. "An Antigen-targeted Approach to Adoptive Transfer Therapy of Cancer", Cancer Res. 59:2167-73 (1999).

Vremec and Shortman "Dendritic Cell Subtypes in Mouse lymphoid Organs: Cross-correlation of Surface Markers, Changes with Incubation and Differences Among Thymus, Spleen and Lymph Nodes" J. Immunol. 159:565-73 (1997).

Vremec et al. "CD4 and CD8 Expression by Dendritic Cell Subtypes in Mouse Thymus and Spleen" J. Immunol. 164:2978-86 (2000).

Wolfer et al. "Knockout Mice: Simple Solutions to the Problems of Genetic Background and Flanking Genes" Trends Neurosci. 25(7):336-40 (2002).

Xiao et al. "Dendritic Cell Vaccine Design: Strategies for Eliciting Peripheral Tolerance as Therapy of Autoimmune Diseases" BioDrugs 17:103-11 (2003).

Yu et al. "RNA Interference by Expression of Short-interfering RNAs and Hairpin RNAs in Mammalian Cells", Proc. Natl. Acad. Sci. USA 99:6047-52 (2002).

Yu et al. "Identification of a Ligand for Glucocorticoid-induced Tumor Necrosis Factor Receptor Constitutively Expressed in Dendritic Cells" Biochem. Biophys. Res. Commun. 310:433-38 (2003).

Database EMBL 'Online!, EBI; XP002307885 retrieved from EBI Database accession No. AY234223 abstract.

Database EMBL 'Online!, EBI; XP002307923 retrieved from EBI Database accession No. Q7TNY2 abstract.

Database EMBL 'Online!, EBI; XP002307924 retrieved from EBI Database accession No. Q80YG2 abstract.

* cited by examiner

```
m   1    ......MEEMPLRESSPQRAERCK.KSWLLCIVALLMLLCSLGTLIYTSL   44
              :|  |||    ||   |: ||| |||  :|| ||| ||:
h   1    MCLSHLENMPLSHSRTQGAQRSSWKLWLFCSIVMLL.FLCSFSWLIFIFL   49 m   45   K.PTAIESCMVKFELSSSKWHMTSPKPHCVNTTSDGKLKILQSGTYLIYG   93
          . |||  ||   ||   ||| |||  ||| ||   |||||| ||||||
h   50   QLETAKEPCMAKFGPLPSKWQMASSEPPCVNKVSDWKLEILQNGLYLIYG   99 m   94   QVIPVDKKYIKDNAPFVVQIYKKNDVLQTLMNDFQILPIGGVYELHAGDN   143
         ||  . |||| ||| || |||||  ||| :||||||||  | :|| :||
h   100  QVAP.NANY.NDVAPFEVRLYKNKDMIQTLTNKSKIQNVGGTYELHVGDT   147 m   144  IYLKFNSKDHIQKNNTYWGIILMPDLPFIS    173
         |||  . : ||||||||||||||||  .  |||
h   148  IDLIFNSEHQVLKNNTYWGIILLANPQFIS    177 m = SEQ ID NO:2
                                                h = SEQ ID NO:9
```

FIGURE 1

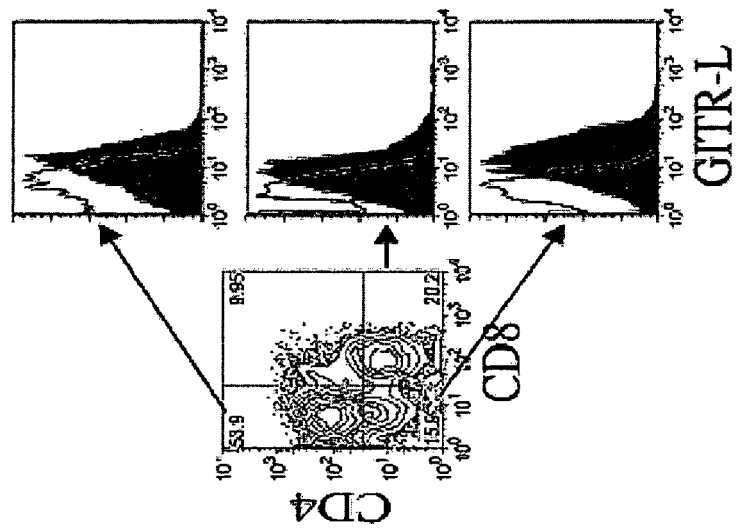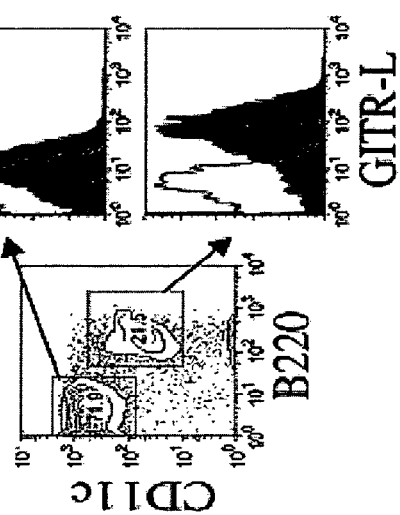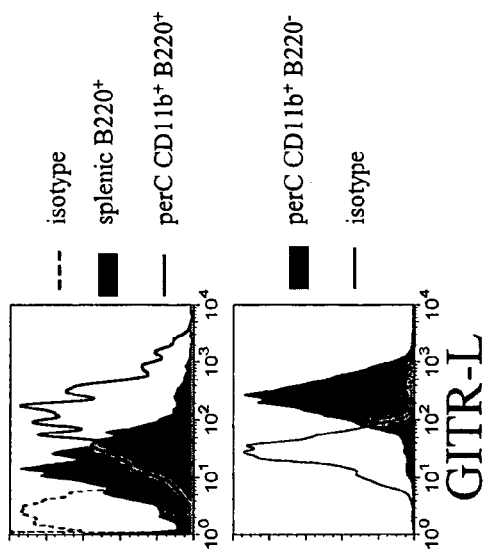
FIGURE 7

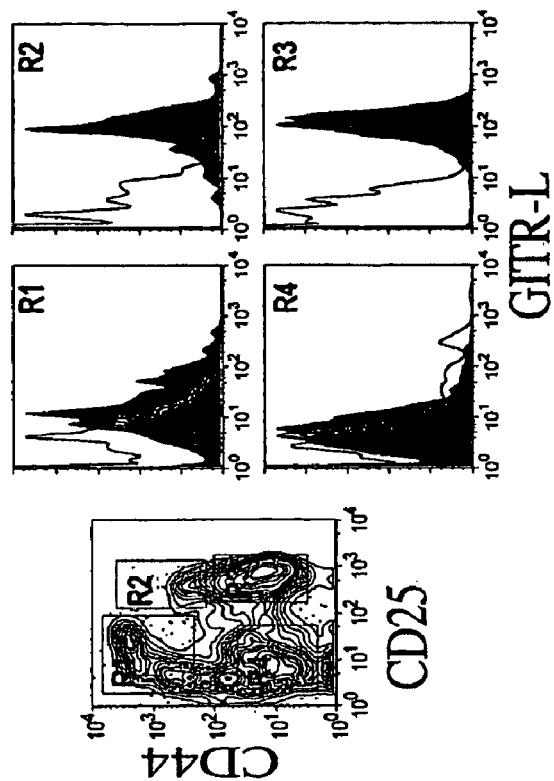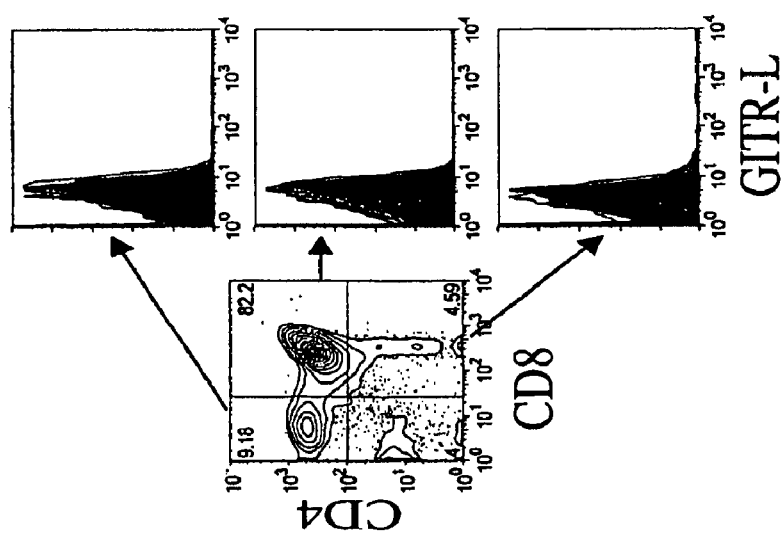
FIGURE 7 CONTINUED

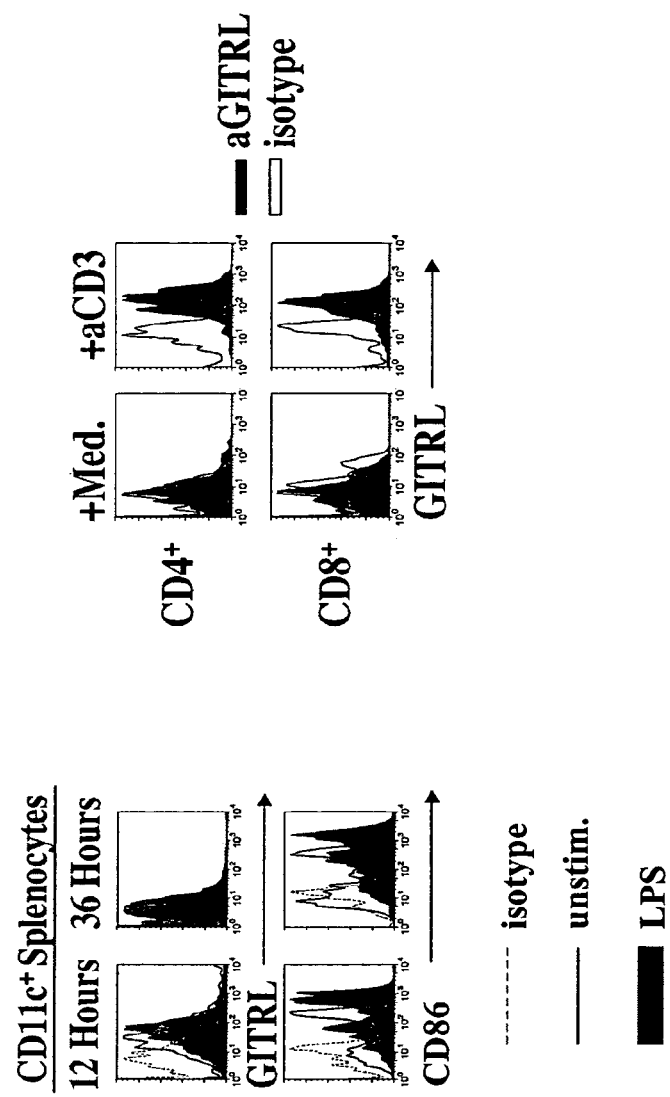
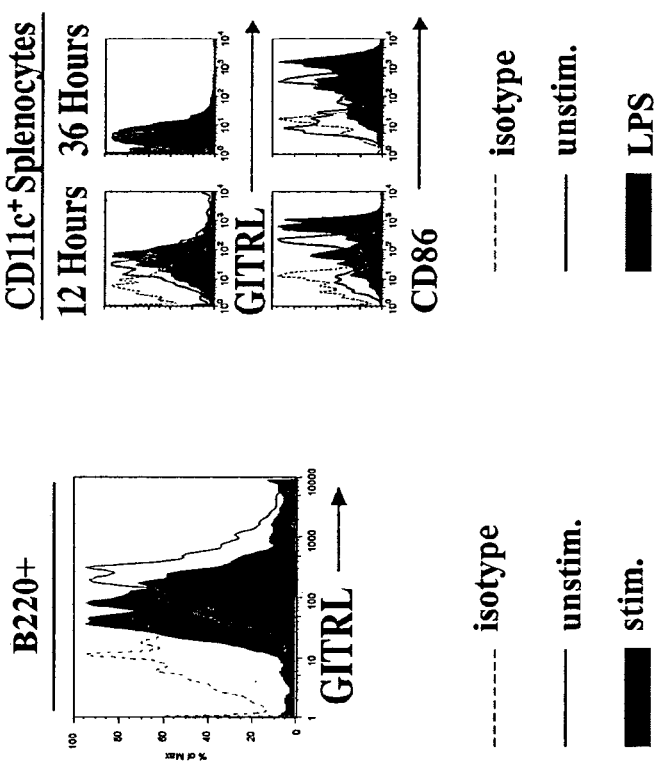
FIGURE 8

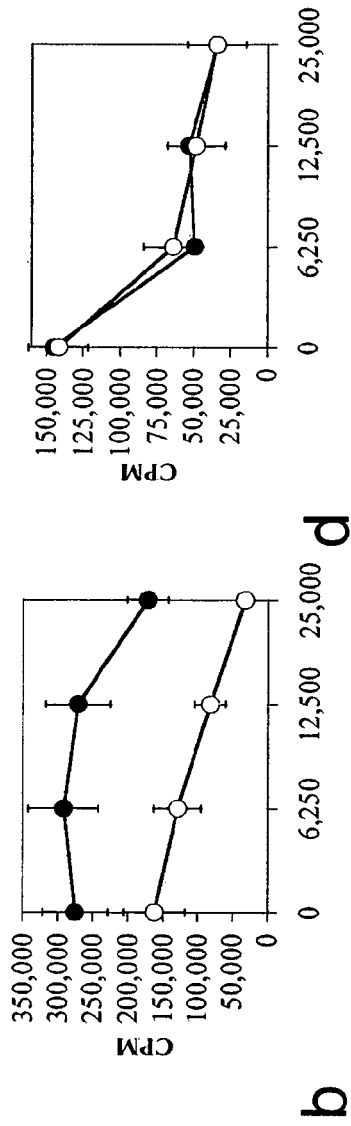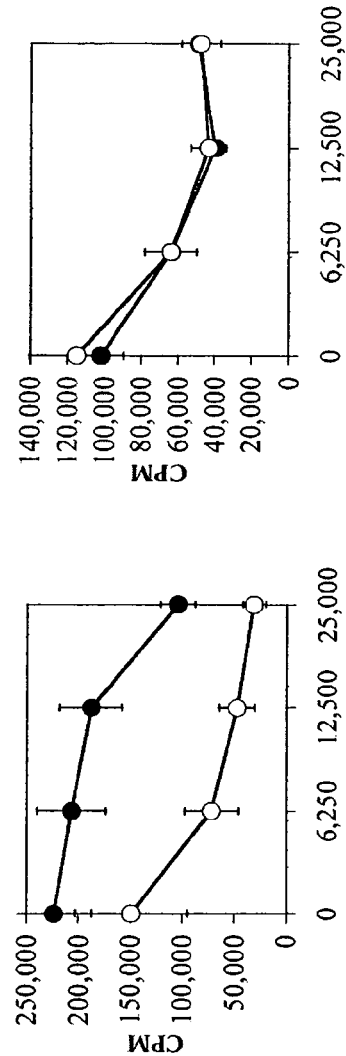
FIGURE 10

B

C
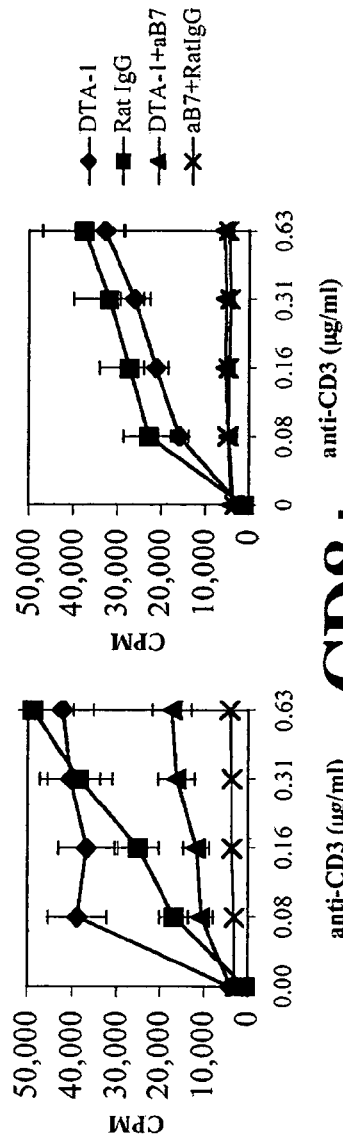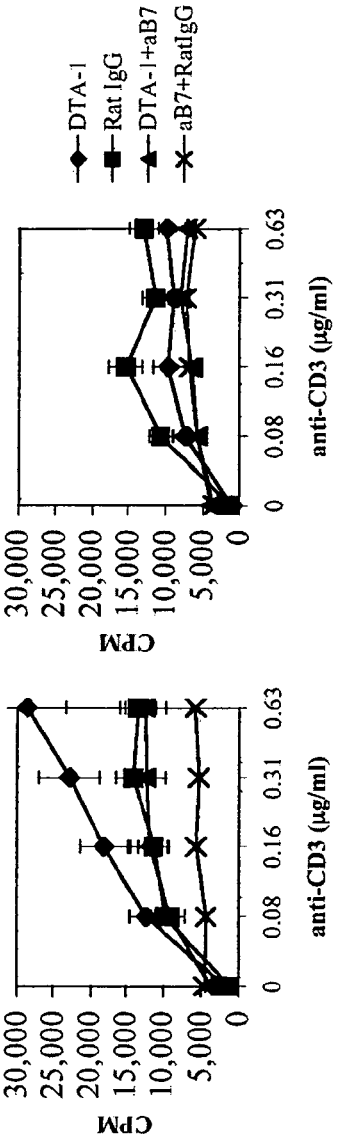
FIGURE 12

C

METHOD OF TREATING OR AMELIORATING AN IMMUNE CELL ASSOCIATED PATHOLOGY USING GITR LIGAND ANTIBODIES

This application claims the benefit of U.S. Provisional Application Ser. No. 60/472,844, filed May 23, 2003, and U.S. Provisional Application Ser. No. 60/547,975, filed Feb. 26, 2004, both of which are incorporated herein by reference in their entireties.

This invention was made with Government support under NIH Intramural Research Project #Z01-AI-000224. The Government has certain rights in the invention.

BACKGROUND OF THE INVENTION

1. Field of the Invention

The present invention is directed to novel methods for diagnosing, prognosing, monitoring the progress of, and treating disorders arising from disregulation of the immune system (e.g., autoimmune disorders, inflammatory diseases, and transplant rejection, and cancer and infectious diseases) related to glucocorticoid-induced TNF receptor (GITR) and the ligand associated with GITR (GITRL) and modulators related thereto. The present invention is further directed to novel therapeutics and therapeutic targets, and to methods of screening and assessing test compounds for the intervention (treatment) and prevention of disorders arising from disregulation of the immune system, as related to GITR and GITRL.

2. Related Background Art

Generally, T lymphocytes are responsible for cell-mediated immunity and play a regulatory role by enhancing or suppressing the responses of other white blood cells. The notion that T lymphocytes play a role in suppression of the immune response is well known (see, e.g., Gershon et al. (1970) *Immunology* 18:723-35). However, the target antigens for these suppressor cells and the mechanisms controlling their function are still subjects of study.

One population of regulatory T cells that is generated in the thymus is distinguishable from effector T cells by the expression of unique membrane antigens. These regulatory T cells make up a subpopulation of $CD4^+$ T cells (i.e., T cells that express the CD4 antigen) that coexpress the CD25 antigen. CD25 is also known as the interleukin-2 receptor (IL-2R) α-chain. Cotransfer of, or reconstitution with, $CD25^+$ T cells is associated with prevention of both inflammatory lesions and autoimmunity in various animal models (see Shevach (2000) *Ann. Rev. Immunol.* 18:423-49, and references therein). $CD4^+CD25^+$ T cells have also been associated with inhibition of T cell activation in vitro, and adoptive suppression of $CD4^+CD25^-$ T cells in coculture (Shevach, supra).

More than two decades ago it was demonstrated that some self-reactive T cells escape mechanisms of central tolerance and exist in the periphery under the control of thymic-derived regulatory T cells. In 1995, Sakaguchi and colleagues demonstrated that a small population of $CD4^+$ T cells that naturally express the α-chain of IL-2R (i.e., CD25) are involved in the control of organ-specific autoreactive T cells (Sakaguchi et al. (1995) *J. Immunol.* 155:1151-64). Specifically, they demonstrated that transfer of $CD4^+CD25^-$ T cells to immunodeficient hosts led to a spectrum of autoimmune diseases, which could be prevented by cotransfer of $CD4^+CD25^+$ T cells (Sakaguchi et al., supra). Subsequent studies have implicated $CD4^+CD25^+$ regulatory T cells in the suppression of immune responses to viral, bacterial and protozoal infections (Aseffa et al. (2002) *J. Immunol.* 169:3232-41; Belkaid et al. (2002) *Nature* 420:502-07; Hisaeda et al. (2004) *Nat. Med.* 10:29-30; Kursar et al. (2002) *J. Exp. Med.* 196:1585-92; Lundgren et al. (2003) *Infect. Immun.* 71:1755-62; Maloy et al. (2003) *J. Exp. Med.* 197:111-19). Together, these studies provided evidence that removal of $CD4^+CD25^+$ T cells enhanced the immune response. Many attempts have been made to define the activation of, and suppression by, these $CD4^+CD25^+$ T cells. These cells represent a unique lineage of thymic-derived cells that potently suppress both in vitro and in vivo effector T cell function.

Several in vitro studies revealed that $CD4^+CD25^+$ cells suppress proliferation of $CD4^+$ T cells in response to both mitogens and antigens by turning off transcription of IL-2 (e.g., Thornton and Shevach (1998) *J. Exp. Med.* 188:287-96; Takahashi et al. (1998) *Int. Immunol.* 10:1969-80). Cotransfer of $CD4^+CD25^+$ T cells in vivo with autoreactive $CD4^+$ T cells is sufficient to suppress both the induction and effector phase of organ-specific autoimmunity (Suri-Payer et al. (1999) *Eur. J. Immunol.* 29:669-77; Suri-Payer et al. (1998) *J. Immunol.* 160:1212-18). Other properties of the $CD4^+CD25^+$ T cells include hyporesponsiveness to T cell receptor (TCR) stimulation in the absence of exogenous IL-2, immunosuppression via cell-cell interaction, and a requirement for TCR signaling to induce their suppressive phenotype (once they have been activated, however, their suppressive function is independent of antigenic stimulus). It has also been demonstrated that the mere acquisition of CD25 expression, as can be achieved by stimulation of $CD4^+CD25^-$ T cells, does not induce the suppressive phenotype. These $CD4^+CD25^+$ T cells are known to exist in humans (Shevach (2001) *J. Exp. Med.* 193:F1-F6).

One study demonstrated that altered thymic selection is required for generation of regulatory $CD4^+CD25^+$ T cells (Jordan et al. (2001) *Nat. Immunol.* 2:301-06). In addition, studies with knockout mice demonstrated that molecules involved in IL-2 synthesis and responsiveness are required for generation of these cells; mice genetically deficient for IL2 or IL2Rβ, or B7.1 (CD80) and B7.2 (CD86), or CD28 all have severe reduction in $CD4^+CD25^+$ cells, with resulting lymphadenopathy and hyperproliferation in the periphery of some of these mice (Papiernik et al. (1998) *Int. Immunol.* 10:371-78; Salomon et al. (2000) *Immunity* 12:431-40; Kurnanogoh et al. (2001) *J. Immunol.* 166:353-60).

Until recently, the art had failed to determine the mechanisms involved in $CD4^+CD25^+$-mediated suppression of the immune system, e.g., the antigen specificity, the molecules involved in acquisition of suppression, and the cell surface molecules or short acting cytokines involved in the effector phase of suppression; the molecular targets of $CD25^+$ T cells in modulating autoimmunity remained largely unknown as well. It has now been demonstrated, by examining differential expression of genes through the use of gene chip analyses on $CD4^+CD25^+$ and $CD4^+CD25^-$ T cells, that several $CD25^+$ differential genes exist (McHugh et al. (2002) *Immunity* 16:311-23; see also U.S. patent application Ser. No. 10/194,754, incorporated herein by reference in its entirety). These genes, determined to be preferentially expressed on the $CD4^+CD25^+$ T cells, can serve as targets for therapeutic intervention and screening methods for autoimmune disorders, inflammatory diseases and transplant rejection, as well as for cancer and infectious diseases.

Significantly, one of the genes determined to be differentially expressed in $CD25^+$ cells is glucocorticoid-induced TNF receptor (GITR) (McHugh et al., supra). GITR, a cell-surface, transmembrane protein receptor, is a member of the tumor necrosis factor receptor (TNFR) superfamily. GITR has been demonstrated to be constitutively present on nonactivated T cells (Gavin et al. (2002) *Nat. Immunol.* 3:33-41;

McHugh et al., supra; Shimizu et al. (2002) *Nat. Immunol.* 3:135-42). GITR binds to another transmembrane protein referred to as GITR Ligand (GITRL). Agonistic antibodies to GITR have been shown to abrogate the suppressor activity of $CD4^+CD25^+$ T cells, demonstrating a functional role for GITR in regulating the activity of these cells (McHugh et al., supra). Another study confirmed that stimulation of GITR with a specific monoclonal antibody abrogated $CD4^+CD25^+$ T cell-mediated suppression, thereby inducing autoimmunity (Shimizu et al., supra). These studies have led to the proposal that GITR is a more faithful marker of $CD4^+CD25^+$ T cells (Uraushihara et al. (2003) *J. Immunol.* 171:708-16); however, GITR expression alone does not exclusively distinguish this subset, as upregulation of GITR also occurs following activation of $CD4^+CD25^-$ T cells (McHugh et al., supra; Shimizu et al., supra).

Because GITR has been shown to be important in the regulation of suppressor activity of $CD4^+CD25^+$ T cells on $CD4^+CD25^-$ T cells, it is desirable to identify and characterize novel molecules that interact with GITR. Such novel molecules that interact with GITR are disclosed herein. Additionally, modulators of these molecules are provided.

SUMMARY OF THE INVENTION

The present invention provides the nucleotide and amino acid sequences of a novel mouse homolog of human GITRL. The present invention also provides antibodies to mouse GITRL. The present invention also provides methods both to reverse immune suppression by inducing agonistic GITR-GITRL binding, and to restore or enhance immune suppression by antagonizing GITR-GITRL binding, e.g., through the use of neutralizing antibodies that inhibit GITRL activity (e.g., that block the interaction between GITR and GITRL). Such reversal, or restoration/enhancement, of immune suppression is beneficial in the treatment of varied disorders resulting from disregulated immune responses, such as autoimmune disorders, inflammatory diseases and transplant rejection, and cancer and infectious diseases. The methods of the present invention are directed to manipulation of GITRL and GITR, including, but not limited to, mouse GITRL and GITR and their homologs; specifically included among these homologs are human GITRL and human GITR.

The present invention provides novel isolated and purified polynucleotides and polypeptides related to a novel ligand for GITR (GITRL). The invention also provides antibodies to GITRL, as well as methods for treating, diagnosing, prognosing, and monitoring the progress of autoimmune disorders, inflammatory diseases, and transplant rejection, and cancers and infectious diseases. In one embodiment of the invention, the disclosed methods and molecules can be used to manipulate the outcome of an immune response during the treatment of a disease or disorder, including autoimmune disorders, inflammatory diseases, and transplant rejection, as well as cancers and infectious diseases. In another embodiment, disclosed polynucleotides and polypeptides of the invention that block or inhibit the interaction between GITR and GITRL, for example by downregulating the expression or activity of GITRL or by binding to GITRL, but do not induce GITR signaling, can be used to restore or enhance suppression of the immune system. In another embodiment, the interaction between GITR and GITRL can be blocked or inhibited by a small molecule. It will be appreciated by one of skill in the art that these types of regulation (i.e., these embodiments) will be most beneficial in the treatment of autoimmune disorders and some inflammatory diseases, and similar or related disorders, as well as in the treatment of transplant rejection. In another embodiment, disclosed polynucleotides and polypeptides of the invention that induce GITR signaling, for example by upregulating the expression or activity of GITRL or by agonistic binding to GITR, can be used to reverse, block, or abrogate suppression of the immune system. In another embodiment, the interaction between GITR and GITRL can be enhanced or mimicked by a small molecule. It will be appreciated by one of skill in the art that these types of regulation will be most beneficial in the treatment of cancers and like diseases, as well as infectious diseases. One of skill in the art would also be aware of the likely benefits of combining these novel therapies with established and other therapies.

In one embodiment, the invention provides an isolated nucleic acid molecule comprising the nucleotide sequence of SEQ ID NO:1 or SEQ ID NO:3. In another embodiment, the nucleic acid molecule is operably linked to at least one expression control sequence. In another embodiment, a host cell transformed or transfected with the nucleic acid molecule is provided.

In another embodiment, the invention provides an isolated allele of SEQ ID NO:1 or SEQ ID NO:3. In another embodiment, the invention provides an isolated gene comprising the nucleotide sequence of SEQ ID NO:3.

In another embodiment, the invention provides an isolated nucleic acid molecule that specifically hybridizes under highly stringent conditions to the nucleotide sequence set forth in SEQ ID NO:1 or SEQ ID NO:3, or the complement thereto.

In another embodiment, the invention provides an isolated nucleic acid molecule that encodes a protein comprising the amino acid sequence of SEQ ID NO:2, or a fragment thereof that encodes an active fragment of the protein. In another embodiment, the nucleic acid molecule, or fragment thereof, is operably linked to at least one expression control sequence. In another embodiment, a host cell transformed or transfected with the isolated nucleic acid molecule, or fragment thereof, operably linked to at least one expression control sequence is provided. In another embodiment, the invention provides a nonhuman transgenic animal in which the somatic and germ cells contain the isolated nucleic acid molecule, or fragment thereof. In another embodiment, the invention provides a nonhuman transgenic animal in which the somatic and germ cells contain DNA comprising the nucleotide sequence of SEQ ID NO:1 or SEQ ID NO:3.

In another embodiment, the invention provides an isolated protein comprising the amino acid sequence encoded for by an isolated nucleic acid that specifically hybridizes under highly stringent conditions to the nucleotide sequence set forth in SEQ ID NO:1 or SEQ ID NO:3, or the complement thereto. In another embodiment, the invention provides an isolated protein comprising the amino acid sequence of SEQ ID NO:2, or an active fragment thereof.

In another embodiment, the invention provides an isolated nucleic acid molecule comprising a nucleotide sequence complementary to the nucleotide sequence of SEQ ID NO:1 or SEQ ID NO:3, or a fragment thereof, wherein expression of the nucleic acid molecule in a cell results in decreased production of GITRL. In another embodiment, the nucleic acid molecule, or fragment thereof, is operably linked to at least one expression control sequence. In another embodiment, a host cell transformed or transfected with the isolated nucleic acid molecule, or fragment thereof, operably linked to at least one expression control sequence is provided. In another embodiment, the invention provides a nonhuman transgenic animal in which the somatic and germ cells contain the isolated nucleic acid molecule, or fragment thereof.

In another embodiment, the invention provides an antisense oligonucleotide complementary to a mRNA corresponding to a nucleic acid molecule comprising the nucleotide sequence of SEQ ID NO:1 or SEQ ID NO:3, or a fragment thereof, wherein the oligonucleotide inhibits expression of GITRL. In another embodiment, the invention provides a siRNA molecule corresponding to a nucleic acid molecule comprising the nucleotide sequence of SEQ ID NO:1 or SEQ ID NO:3, or a fragment thereof, wherein the siRNA molecule inhibits expression of GITRL.

In another embodiment, the invention provides an isolated antibody capable of specifically binding to an isolated protein comprising the amino acid sequence encoded for by an isolated nucleic acid that specifically hybridizes under highly stringent conditions to the nucleotide sequence set forth in SEQ ID NO:1 or SEQ ID NO:3, or the complement thereto. In another embodiment, the antibody neutralizes GITRL activity. In another embodiment, the antibody is 5F1, having ATCC number PTA-5336, or 10F12, having ATCC number PTA-5337. In another embodiment, the antibody comprises the antigen binding fragments of 5F1 or 10F12. In another embodiment, the invention provides an isolated antibody capable of specifically binding to an isolated protein comprising the amino acid sequence of SEQ ID NO:2, or an active fragment thereof. In another embodiment, the antibody neutralizes GITRL activity. In another embodiment, the antibody is 5F1, having ATCC number PTA-5336, or 10F12, having ATCC number PTA-5337. In another embodiment, the antibody comprises the antigen binding fragments of 5F1 or 10F12.

In another embodiment, the invention provides a method of screening for test compounds capable of inhibiting or blocking the interaction of GITRL with GITR comprising the steps of contacting a sample containing GITRL and GITR with a test compound and determining whether the interaction of GITRL with GITR in the sample is decreased relative to the interaction of GITRL with GITR in a sample not contacted with the compound, whereby a decrease in the interaction of GITRL with GITR in the sample contacted with the compound identifies the compound as one that inhibits or blocks the interaction of GITRL with GITR. In another embodiment, the identified compound is used in a method of treating a subject at risk for, or diagnosed with, an autoimmune disorder, an inflammatory disease, or transplant rejection, the method comprising the steps of isolating T cells from the subject, treating the isolated T cells with the identified compound, and transferring the treated T cells back into the subject. In another embodiment, the identified compound is used in a method of treating a subject at risk for, or diagnosed with, an autoimmune disorder, an inflammatory disease, or transplant rejection, the method comprising administering to the subject the identified compound. In another embodiment, the invention provides a method for assessing the efficacy of the identified compound in a subject comprising the steps of detecting a first number of effector T cells from the subject prior to administration of the compound to the subject, detecting a second number of effector T cells from the subject after administration of the compound to the subject, and comparing the first number and the second number, whereby a significant decrease in the number of effector T cells in the second number as compared to the first number indicates that the compound is efficacious in treating an autoimmune disorder, an inflammatory disease, or transplant rejection in the subject. In another embodiment, the effector T cells are CD4$^+$ T cells or CD8$^+$ T cells.

In another embodiment, the invention provides a method of screening for test compounds capable of enhancing or mimicking the interaction of GITRL with GITR comprising the steps of contacting a sample containing GITRL and GITR with a test compound and determining whether the interaction of GITRL with GITR in the sample is increased relative to the interaction of GITRL with GITR in a sample not contacted with the compound, whereby an increase in the interaction of GITRL with GITR in the sample contacted with the compound identifies the compound as one that enhances or mimics the interaction of GITRL with GITR. In another embodiment, the identified compound is used in a method of treating a subject at risk for, or diagnosed with, cancer or an infectious disease, the method comprising the steps of isolating T cells from the subject, treating the isolated T cells with the identified compound, and transferring the treated T cells back into the subject. In another embodiment, the identified compound is used in a method of treating a subject at risk for, or diagnosed with, cancer or an infectious disease, the method comprising administering to the subject the identified compound. In another embodiment, the invention provides a method for assessing the efficacy of the identified compound in a subject comprising the steps of detecting a first number of effector T cells from the subject prior to administration of the compound to the subject, detecting a second number of effector T cells from the subject after administration of the compound to the subject, and comparing the first number and the second number, whereby a significant increase in the number of effector T cells in the second number as compared to the first number indicates that the compound is efficacious in treating cancer or an infectious disease in the subject. In another embodiment, the effector T cells are CD4$^+$ T cells or CD8$^+$ T cells.

In another embodiment, the invention provides a method for diagnosing an autoimmune disorder, an inflammatory disease, or transplant rejection in a subject comprising the steps of detecting a test amount of a GITRL gene product in a sample from the subject, and comparing the test amount with a normal amount of the GITRL gene product in a control sample, whereby a test amount significantly above the normal amount provides a positive indication in the diagnosis of an autoimmune disorder, an inflammatory disease, or transplant rejection. In another embodiment, the invention provides a method for diagnosing cancer or an infectious disease in a subject comprising the steps of detecting a test amount of a GITRL gene product in a sample from the subject, and comparing the test amount with a normal amount of the GITRL gene product in a control sample, whereby a test amount significantly below the normal amount provides a positive indication in the diagnosis of cancer or an infectious disease.

In another embodiment, the invention provides a method of treating a subject at risk for, or diagnosed with, an autoimmune disorder, inflammatory disease, or transplant rejection comprising administering to the subject a GITR antagonist. In another embodiment, the method comprises administering the GITR antagonist such that the susceptibility of the effector T cells in the subject to suppression by CD4$^+$CD25$^+$ regulatory T cells is maintained (e.g., in an amount effective to maintain such susceptibility). In another embodiment, the GITR antagonist is selected from the group consisting of a neutralizing anti-GITRL antibody, a neutralizing anti-GITR antibody, a fusion protein containing GITR, a fusion protein containing an active fragment of GITR, an antagonistic small molecule, an antisense GITRL nucleic acid molecule, and a siRNA GITRL nucleic acid molecule. In another embodiment, the autoimmune disorder or inflammatory disease is selected from the group consisting of rheumatoid arthritis, encephalomyelitis, osteoarthritis, multiple sclerosis, autoimmune gastritis, systemic lupus erythematosus, psoriasis and other inflammatory dermatoses, type I diabetes, asthma, allergy, and inflammatory bowel diseases, including Crohn's disease and ulcerative colitis.

In another embodiment, the invention provides a method of treating a subject at risk for, or diagnosed with, cancer or an infectious disease comprising administering to the subject a GITR agonist. In another embodiment, the method comprises administering the GITR agonist such that GITR agonist provides a costimulatory signal to effector T cells in the subject and renders them less susceptible to suppression by $CD4^+$ $CD25^+$ regulatory T cells in the subject (e.g., in an amount effective to provide such a signal). In another embodiment, the GITR agonist is selected from the group consisting of GITRL, an active fragment of GITRL, a fusion protein containing GITRL, a fusion protein containing an active fragment of GITRL, and an agonistic GITR antibody.

In another embodiment, the invention provides a method of inducing proliferation of a cell population containing effector T cells comprising administering a GITR agonist to the cell population. In another embodiment, the GITR agonist is selected from the group consisting of GITRL, an active fragment of GITRL, a fusion protein containing GITRL, a fusion protein containing an active fragment of GITRL, and an agonistic GITR antibody. In another embodiment, the effector T cells are $CD4^+$ T cells or $CD8^+$ T cells.

In another embodiment, the invention provides a method of inhibiting proliferation of a cell population containing effector T cells comprising administering a GITR antagonist to the cell population. In another embodiment, the GITR antagonist is selected from the group consisting of a neutralizing anti-GITRL antibody, a neutralizing anti-GITR antibody, a fusion protein containing GITR, a fusion protein containing an active fragment of GITR, an antagonistic small molecule, an antisense GITRL nucleic acid molecule, and a siRNA GITRL nucleic acid molecule. In another embodiment, the effector T cells are $CD4^+$ T cells or $CD8^+$ T cells. In another embodiment, the GITR antagonist is 5F1 or 10F12.

In another embodiment, the invention provides a method of inhibiting or blocking suppression of a cell population comprising effector T cells in the presence of $CD4^+CD25^+$ regulatory T cells comprising administering a GITR agonist to the cell population. In another embodiment, the method comprises administering the GITR agonist such that the GITR agonist provides a costimulatory signal to the effector T cells and renders them less susceptible to suppression by the $CD4^+$ $CD25^+$ regulatory T cells (e.g., in an amount effective to provide such a signal). In another embodiment, the GITR agonist is selected from the group consisting of GITRL, an active fragment of GITRL, a fusion protein containing GITRL, a fusion protein containing an active fragment of GITRL, and an agonistic GITR antibody. In another embodiment, the effector T cells are $CD4^+$ T cells or $CD8^+$ T cells.

In another embodiment, the invention provides a method of suppressing a cell population comprising effector T cells in the presence of $CD4^+CD25^+$ regulatory T cells comprising administering a GITR antagonist to the cell population. In another embodiment, the method comprises administering the GITR antagonist such that the susceptibility of the effector T cells to suppression by the $CD4^+CD25^+$ regulatory T cells is maintained (e.g., in an amount effective to maintain such susceptibility). In another embodiment, the GITR antagonist is selected from the group consisting of a neutralizing anti-GITRL antibody, a neutralizing anti-GITR antibody, a fusion protein containing GITR, a fusion protein containing an active fragment of GITR, an antagonistic small molecule, an antisense GITRL nucleic acid molecule, and a siRNA GITRL nucleic acid molecule. In another embodiment, the effector T cells are $CD4^+$ T cells or $CD8^+$ T cells. In another embodiment, the GITR antagonist is 5F1 or 10F12.

In another embodiment, the invention provides a method of inhibiting the expression of GITRL in a cell population comprising treating the cell population with an isolated nucleic acid molecule comprising a nucleotide sequence complementary to the nucleotide sequence of SEQ ID NO:1 or SEQ ID NO:3, or a fragment thereof, wherein expression of the nucleic acid molecule in a cell results in decreased production of GITRL In another embodiment, the invention provides a method of inhibiting the expression of GITRL in a cell population comprising treating the cell population with an antisense oligonucleotide complementary to a mRNA corresponding to a nucleic acid molecule comprising the nucleotide sequence of SEQ ID NO:1 or SEQ ID NO:3, or a fragment thereof, wherein the oligonucleotide inhibits expression of GITRL.

In another embodiment, the invention provides a method of inhibiting the expression of GITRL in a cell population comprising treating the cell population with a siRNA molecule targeted to a mRNA corresponding to an isolated nucleic acid molecule comprising the nucleotide sequence of SEQ ID NO:1 or SEQ ID NO:3. In another embodiment, the invention provides a method of inhibiting the expression of GITRL in a cell population comprising treating the cell population with a siRNA molecule targeted to a mRNA corresponding to an isolated nucleic acid molecule comprising a nucleotide sequence complementary to the nucleotide sequence of SEQ ID NO:1 or SEQ ID NO:3.

In another embodiment, the invention provides a method of inhibiting the expression of GITRL in a cell population comprising treating the cell population with an antisense oligonucleotide to a nucleic acid molecule encoding GITRL. In another embodiment, the invention provides a method of inhibiting the expression of GITRL in a cell population comprising treating the cell population with a siRNA molecule targeted to a mRNA encoding GITRL.

In another embodiment, the invention provides a method of inducing the expression of GITRL in a cell population comprising treating the cell population by transforming or transfecting the cell population with an isolated nucleic acid molecule comprising the nucleotide sequence of SEQ ID NO:1 or SEQ ID NO:3, or with an isolated nucleic acid molecule that encodes a protein comprising the amino acid sequence of SEQ ID NO:2, or a fragment thereof that encodes an active fragment of the protein, wherein the nucleic acid molecule is operably linked to at least one expression control sequence.

In another embodiment, the invention provides a population of effector T cells that have been contacted in vitro or ex vivo with a GITR agonist. In another embodiment, the GITR agonist is selected from the group consisting of GITRL, or an active fragment of GITRL, a fusion protein containing GITRL, a fusion protein containing an active fragment of GITRL, an agonistic small molecule, and an agonistic anti-GITR antibody. In another embodiment, the effector T cells are $CD4^+$ T cells or $CD8^+$ T cells.

In another embodiment, the invention provides a method of treating cancer or an infectious disease in a subject, the method comprising the steps of obtaining a population of effector T cells, treating the population with a GITR agonist, and administering the treated population to the subject afflicted with cancer or an infectious disease. In another embodiment, the GITR agonist is selected from the group consisting of GITRL, an active fragment of GITRL, a fusion protein containing GITRL, a fusion protein containing an active fragment of GITRL, an agonistic small molecule, and an agonistic anti-GITR antibody. In another embodiment, the subject is afflicted with cancer and the treated population is used as a tumor vaccine.

In another embodiment, the invention provides a pharmaceutical composition comprising a GITR agonist and a pharmaceutically acceptable carrier. In another embodiment, the GITR agonist is selected from the group consisting of GITRL, an active fragment of GITRL, a fusion protein containing GITRL, a fusion protein containing an active fragment of GITRL, an agonistic small molecule, and an agonistic anti-GITR antibody.

In another embodiment, the invention provides a pharmaceutical composition comprising a GITR antagonist and a pharmaceutically acceptable carrier. In another embodiment, the GITR antagonist is selected from the group consisting of a neutralizing anti-GITRL antibody, a neutralizing anti-GITR antibody, a fusion protein containing GITR, a fusion protein containing an active fragment of GITR, an antagonistic small molecule, an antisense GITRL nucleic acid molecule, and a siRNA GITRL nucleic acid molecule. In another embodiment, the antibody comprises the antigen binding fragments of 5F1 or 10F12.

In another embodiment, the invention provides a vaccine adjuvant comprising a GITR agonist and an antigen selected from the group consisting of a viral antigen, a bacterial antigen, a fungal antigen, a parasitic antigen, a cancer antigen, a tumor-associated antigen, and fragments thereof. In another embodiment, the GITR agonist is selected from the group consisting of GITRL, or an active fragment of GITRL, a fusion protein containing GITRL, a fusion protein containing an active fragment of GITRL, an agonistic small molecule, and an agonistic anti-GITR antibody.

In another embodiment, the invention provides a vaccine adjuvant comprising a GITR antagonist and an antigen selected from the group consisting of an autoantigen, amyloid peptide protein, an alloantigen, a transplant antigen, an allergen, and fragments thereof. In another embodiment, the GITR antagonist is selected from the group consisting of a neutralizing anti-GITRL antibody, a neutralizing anti-GITR antibody, a fusion protein containing GITR, a fusion protein containing an active fragment of GITR, an antagonistic small molecule, an antisense GITRL nucleic acid molecule, and a siRNA GITRL nucleic acid molecule. In another embodiment, the antibody comprises the antigen binding fragments of 5F1 or 10F12.

In another embodiment, the invention provides a method of screening for test compounds capable of neutralizing GITRL activity comprising the steps of contacting a sample containing GITRL and a neutralizing antibody with the compound, and determining whether the interaction of GITRL with the neutralizing antibody in the sample is decreased relative to the interaction of GITRL with the neutralizing antibody in a sample not contacted with the compound, whereby a decrease in the interaction of GITRL with the neutralizing antibody in the sample contacted with the compound identifies the compound as one that inhibits or blocks the interaction of GITRL with the neutralizing antibody. In another embodiment, the antibody is 5F1 or 10F12.

In another embodiment, the invention provides a method of providing a costimulatory signal to a cell population comprising effector T cells, the method comprising administering a GITR agonist. In another embodiment, the GITR agonist is protein selected from the group consisting of selected from the group consisting of GITRL, or an active fragment of GITRL, a fusion protein containing GITRL, a fusion protein containing an active fragment of GITR, and an agonistic anti-GITR antibody. In another embodiment, the effector T cells are $CD4^+$ T cells or $CD8^+$ T cells.

BRIEF DESCRIPTION OF THE DRAWINGS

FIG. 1 shows the alignment (based on BLOSUM62 amino acid substitution matrix; see Henikoff and Henikoff (1992) *Proc. Natl. Acad. Sci. USA* 89:10915-19) of the amino acid sequences for mouse (m; SEQ ID NO:2) and human (h; SEQ ID NO:9) GITRL.

FIG. 2A shows that an agonistic anti-GITR antibody stimulated the proliferation of $CD4^+CD25^+$ T cells, but not $CD4^+CD25^-$ T cells. FIG. 2B shows that YB2/0 cells expressing GITRL stimulated the proliferation of $CD4^+CD25^+$ cells.

FIG. 5B includes an additional experiment showing that a control antibody ("control Ig") did not restore suppression.

FIG. 6A shows the suppression of the proliferation of lymph node cells in the presence of anti-GITRL antibody (5F1). FIG. 6B shows the lack of the suppressive activity of anti-GITRL antibody when the lymph node cell population was depleted of $CD4^+CD25^+$ T cells.

FIG. 7A: Flow cytometric analysis was performed on $CD11c^+$ cells, enriched from the spleen of BALB/c mice with magnetic beads, by staining with anti-CD4, anti-CD8 and anti-GITRL antibodies. GITRL expression was determined by comparing the fluorescence intensity of $CD4^+$, $CD8^+$, and $CD4^- CD8^-$-gated subsets (top, middle, and bottom histogram panels, respectively) stained with anti-GITRL antibody (filled histograms) to the fluorescence intensity of these cells stained with an isotype control antibody (unfilled histograms). FIG. 7B: Expression of GITRL by splenic dendritic cells (DCs) and B-1 B cells was determined by staining freshly isolated BALB/c $CD11c^+$ splenic DCs (top histogram panel) and $CD11c^{low}B220^+$ plasmacytoid DCs (bottom histogram panel) with anti-GITRL mAb (filled histograms) or an isotype control antibody (unfilled histograms) and performing flow cytometric analysis. FIG. 7C (top histogram panel): The fluorescence intensities of $B220^+$ B cells among total splenocytes (filled histogram), and $CD11b^+B220^+$-gated peritoneal (perc) B-1 B cells (solid line unfilled histogram) stained with anti-GITRL antibody were compared with the fluorescence intensity of cells stained with an isotype control (broken line unfilled histogram). FIG. 7C (bottom histogram panel): A comparison of the fluorescence intensity of GITRL-antibody stained (filled histogram) and isotype antibody stained (unfilled histogram) perc macrophages (CD11B$^+$B220$^-$ cells) is shown. FIG. 7D: Thymocytes were stained for expression of CD4, CD8, and either GITRL or an isotype control. The fluorescence intensities of CD4$^+$ CD8$^-$ (top left quadrant), CD4$^+$CD8$^+$ (top right quadrant) and CD4$^-$CD8$^+$ (bottom right quadrant) cells stained with anti-GITRL antibody (filled histogram) were compared with the fluorescence intensities of these cells stained with an isotype control antibody (unfilled histogram). FIG. 7E: Expression of GITRL by gated CD44$^+$CD25$^-$ (R1), CD44$^+$CD25$^+$ (R2), CD44$^-$CD25$^+$ (R3) or CD44$^-$CD25$^-$ (R4) thymic precursors was determined by comparing the fluorescence of these cells stained with anti-GITRL antibody (filled histogram) with the fluorescence of these cells stained with isotype control antibody (unfilled histogram). FIG. 7F: Unstimulated lymph node cells were stained with anti-CD4, anti-CD8, anti-CD25 and/or anti-GITRL antibodies. CD4$^+$CD8$^-$ cells (top left quadrant), and not CD4$^-$ CD8$^+$ cells (bottom right quadrant), were further delineated with respect to the expression of CD25 by these cells. Expression of GITRL by CD4$^+$CD8$^-$CD25$^-$ (top right histogram panel), CD4$^+$CD8$^-$CD25$^+$ (lower right histogram panel) or CD4$^-$CD8$^+$ (bottom (middle) histogram panel)-gated lymph node cells was determined by comparing the fluorescence intensity of these cells stained with anti-GITRL antibody (filled histograms) with the fluorescence of these cells stained with an isotype control antibody (unfilled histograms). Results are representative of five independent experiments.

FIG. 8A: Expression of GITRL by purified splenic B220$^+$ B cells or total peritoneal (PerC) B220$^+$ CD11b$^+$ B-1 B cells was determined for different time points following treatment with polyI:C (10 µg/ml), LPS (0.5 µg/ml), CpGs (ODN 1826, 1 µM), anti-CD40 and IL-4 (10 µg/ml and 20 ng/ml, respectively) and anti-IgM (F(ab')$_2$ fragment of goat-anti-IgM µ-chain, 1 µg/ml). The fluorescence intensities of anti-GITRL-stained stimulated cells (filled histograms), anti-GITRL-stained unstimulated (medium) cells (solid line unfilled histograms) and isotype control antibody stained cells (broken line unfilled histograms) are presented. FIG. 8B: Expression of GITRL by B220$^+$ B cells (filled histogram) present among total splenocytes treated with anti-CD3 mAb (0.5 µg/ml) after a 48-hour culture period was compared with expression of GITRL by unstimulated B220$^+$ B cells (solid line unfilled histogram) and B220$^+$ B cells stained with an isotype control antibody (broken line unfilled histogram). FIG. 8C: Expression of GITRL (top histogram panels) and B7.2 (i.e., CD86) (bottom histogram panels) by purified CD11c$^+$ DCs following culture with or without LPS (0.5 µg/ml) at the indicated time points. FIG. 8D: Expression of GITRL by total splenocytes gated on CD4$^+$ or CD8$^+$-expressing cells after a 48-hour culture period in the absence or presence of soluble anti-CD3 mAb (0.5 µg/ml). Graphs are representative of two to four independent experiments; all experiments were carried out with tissues isolated from BALB/c mice.

FIG. 9A: Proliferation (y-axis) of lymph node (LN; 1×10$^5$) and spleen cells (Sp; 0.5×10$^5$) with or without CD25$^+$ cells (Total or Δ25, respectively) was determined after 72-hour culture with different concentrations of soluble anti-CD3 (x-axis). Cells were incubated either in the presence of purified anti-GITRL mAb (10 µg/ml; closed circles) or a rat IgG2$_a$ isotype control (10 µg/ml; open circles). Results are representative of three independent experiments. FIG. 9B: CD4$^+$CD25$^-$ or CD8$^+$ T cells were cultured in the presence of 5×10$^4$ irradiated (3000R) T-depleted APCs and 5×10$^4$ irradiated (8000R) YB2/0-GITRL (open circles) or control YB2/0 (closed circles) cells. Cultures were activated with different concentrations of soluble anti-CD3 mAb (x-axis), and proliferation (y-axis) was measured after a 72-hour culture period. FIG. 9C: Mean fluorescence (x-axis) of purified CD4$^+$CD25$^-$ T cells stained with anti-GITR antibody was determined at different time points following activation with soluble anti-CD3 (0.5 µg/ml) in the presence of irradiated (3000R) T-depleted splenocytes. Results are representative of at least two independent experiments.

FIG. 10A: Proliferation of cocultures of CD4$^+$CD25$^-$ T cells (5×10$^4$) from various knockout mice, and variable numbers of CD4$^+$CD25$^+$ T cells (x-axis) from various knockout mice [(Aa) CD4$^+$CD25$^-$: GITR$^{+/+}$, CD4$^+$CD25$^+$: GITR$^{+/+}$; (Ab) CD4$^+$CD25$^-$: GITR$^{+/+}$, CD4$^+$CD25$^+$: GITR$^{-/-}$; (Ac) CD4$^+$CD25$^-$: GITR$^{-/-}$, CD4$^+$CD25$^+$: GITR$^{+/+}$; and (Ad) CD4$^+$CD25$^-$: GITR$^{-/-}$, CD4$^+$CD25$^+$: GITR$^{-/-}$], incubated with irradiated APCs from wild type mice (5×10$^4$) and with soluble anti-CD3 (0.5 µg/ml) and 2 µg/ml of either anti-GITR antibody (filled circles) or an isotype control antibody (open circles) was determined by measuring $^3$H-thymidine uptake (cpm; y-axis). FIG. 10B: Proliferation of cocultures was performed as above (FIG. 10A) with variable numbers of mouse CD4$^+$CD25$^+$ T cells (x-axis) and either (Ba) mouse CD4$^+$CD25$^-$ T cells or (Bb) rat CD4$^+$CD25$^-$ T cells in the presence of irradiated (3000R) rat APCs. Cultures were stimulated with a cocktail of antibodies against both rat and mouse anti-CD3 (0.25 µg/ml of each), and were treated with 2 µg/ml of either an isotype control (Rat IgG; open circles) or anti-GITR (DTA-1; filled circles) antibody. Bars indicate the s.d. values calculated from proliferation in triplicate cultures. FIG. 10C: Fluorescence (x-axis) of CFSE-stained mouse CD4$^+$CD25$^+$ (top panels) and rat CD4$^+$CD25$^-$ T cells (bottom panels) cocultured at a 1:8 suppressor to responder ratio with isotype control (Rat IgG; left panels) or anti-GITR antibody (DTA-1; right panels) is depicted. Mouse and rat T cell subsets were distinguished by staining with specific anti-CD4 antibodies. Results are representative of two to four independent experiments.

FIG. 11 A: CFSE-labeled lymph node (LN) cells (5×10$^4$) from B6 (wild type), GITR$^{+/-}$, CD28$^{-/-}$ and GITR$^{-/-}$ mice were cultured for 72 hours with different concentrations of soluble anti-CD3 mAb (x-axis). Total LN cells were cultured without (Aa) or with (Ac) exogenous of IL-2 (50 U/ml). LN cells depleted of CD25$^+$ cells (LNΔ25) were cultured without (Ab) or with (Ad) exogenous IL-2 (50 U/ml). Bars indicating the s.d. values were omitted for clarity. FIG. 11B: Flow cytometric assessment of CFSE dilution by CD4$^+$ and CD8$^+$-gated lymph node T cells isolated from CD28$^{-/-}$, GITR$^{-/-}$, GITR$^{+/+}$ or GITR$^{+/-}$ animals was performed after 72-hour culture. The results correspond to the 0.63 µg/ml concentration of soluble anti-CD3 (as in FIG. 11A). FIG. 11C: Flow cytometric analysis of CD25 expression was performed on H-2D$^b$ positive CD4$^+$CD25$^-$ cells that remained unstimulated (broken line unfilled histograms), were obtained from GITR$^{-/-}$ mice (solid line unfilled histograms), or were obtained from GITR$^{+/+}$ mice (filled histograms). CD25 expression by CD4$^+$CD25$^-$ cells obtained from GITR$^{-/-}$ or GITR$^{+/+}$ mice was determined after 24-hour culture with LN APCs from wild type mice, in the presence of anti-CD3 (0.5 µg/ml), and in the absence (left histogram panels) or presence (right histogram panels) of CD4$^+$CD25$^+$ cells from BALB/c mice at a 1:2 suppressor to responder ratio. CD25 expression was also determined in the absence (top histogram panels) or presence (bottom histogram panels) of 50 U/ml rhIL-2. Results above are representative of three independent experiments.

FIG. 12A: Flow cytometric analysis of GITR expression by purified CD4$^+$CD25$^-$ or CD8$^+$ T cells (2.5×10$^4$) after 72-hour culture with plate-bound anti-CD3 and 2 µg/ml of either plate-bound hamster isotype ("aCD3") or plate-bound anti-CD28 ("aCD3+aCD28"). FIG. 12B (left histogram panel): Anti-GITR staining of CD4$^+$CD25$^-$ T cells cultured in the presence of irradiated, T cell-depleted splenocytes and soluble anti-CD3 (0.5 µg/ml) with or without a cocktail of anti-CD80/86 (10 µg/ml of each) antibodies (i.e., anti-B7.1/7.2 antibodies) for 72 hours. FIG. 12B (right histogram panel): Anti-GITR staining of CD4$^+$CD25$^-$ T cells cultured in the presence of irradiated, T cell-depleted splenocytes and soluble anti-CD3 (0.5 µg/ml) with or without a cocktail of antibodies against IL-2 and IL-2Rα. FIG. 12C: Proliferation was assessed in the presence or absence of anti-CD80/86 mAbs (10 µg/ml of each; "aB7") with the addition of either anti-GITR mAb (2 µg/ml; "DTA-1") or an isotype control antibody (2 µg/ml; "Rat IgG"). Bars indicate the s.d. values. Results are representative of two to three independent experiments.

FIG. 13A: Proliferation of effector GITR$^+$/TCR$^+$ HT-2 T cells (4×10$^4$) alone (white bars) or cocultured with 1×10$^4$ control YB2/0 cells (cross-hatch bars) or GITRL-expressing YB2/0 cells (filled bars), in the absence or presence of one or two anti-CD3 beads per HT-2 cell, was determined by measuring $^3$H-thymidine uptake (cpm; y-axis). FIG. 13B: Proliferation of 4×10$^4$ HT-2 cells cocultured with two anti-CD3 beads per cell, 1×10$^4$ GITRL-expressing YB2/0 cells, and increasing concentrations (ng/ml; x-axis) of an anti-GITRL antibody (5F1.1; filled circles) or an isotype control antibody (rIgG1; open circles) was determined by measuring $^3$H-thymidine uptake (cpm; y-axis). FIG. 13C: Proliferation of 4×10$^4$ HT-2 cells cocultured with two anti-CD3 beads per cell, 1×10$^4$ GITRL-expressing YB2/0 cells, and increasing concentrations (ng/ml; x-axis) of four different anti-GITRL antibodies: 5F1.1 (filled circles), MGLT-10 (filled squares), MGTL-15 (open squares) or a polyclonal antibody (open circles) was determined by measuring $^3$H-thymidine uptake (cpm; y-axis).

DETAILED DESCRIPTION OF THE INVENTION

Figure 2:
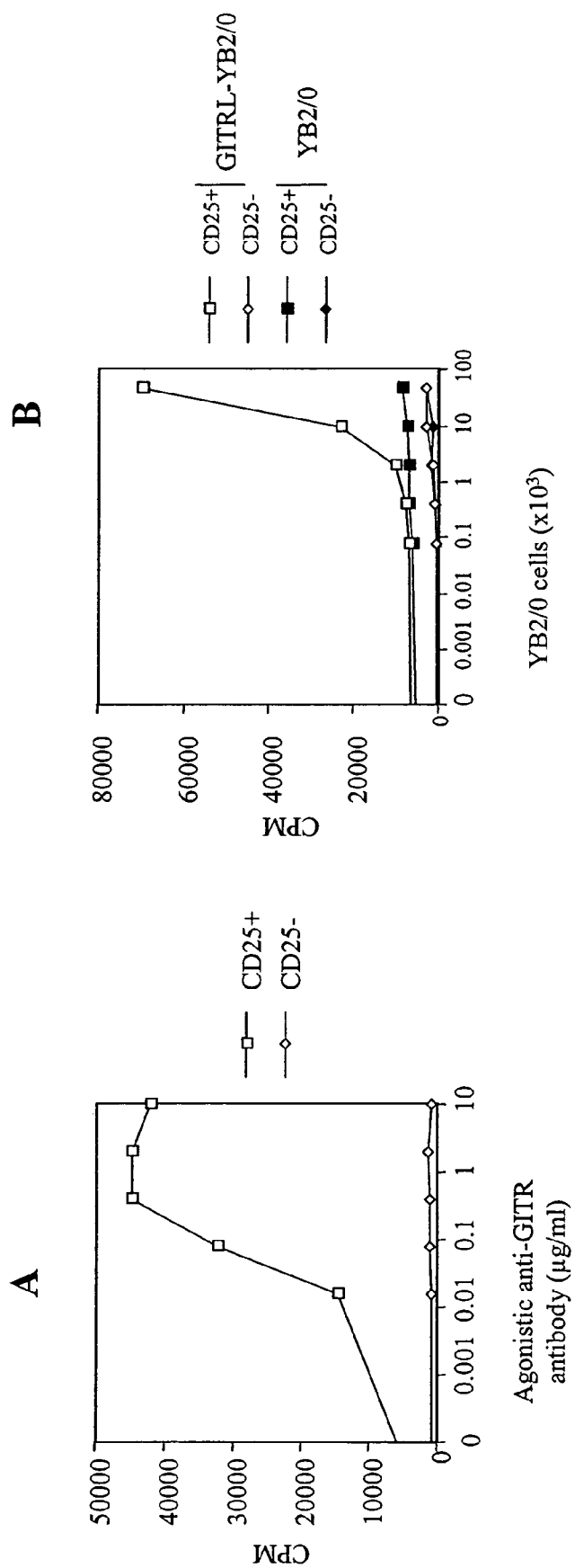
FIG. 2 shows the results of experiments on the effects of GITRL:GITR binding on proliferation of $CD4^+CD25^+$ T cells. Thymidine incorporation is measured (CPM) as a means of assessing cellular proliferation.

As the antibodies to GITR that produce a reversal of suppressive activity appear to produce an agonistic signal, it was predicted that engagement of GITR by GITRL should also inhibit the suppressive activity of regulatory T cells. The lack of suitable reagents previously has precluded a detailed functional analysis of GITR/GITRL interactions under more physiological conditions. Here, the mouse ortholog of GITRL has been identified, and antagonistic antibodies that specifically bind to the mouse ortholog of GITRL, i.e., do not cross-react with human GITRL, have been generated.

Using this reagent, the tissue distribution and regulation of GITRL were examined. In addition, the ability of GITR/GITRL interactions to regulate T cell suppression was investigated using GITR$^{-/-}$ mice. As both CD25$^-$ and CD25$^+$ T cells express GITR, albeit to varying degrees, the previous studies demonstrating an inhibition of suppressor function upon treatment of cocultures with an agonistic anti-GITR antibody yielded equivocal results regarding the cellular target of engagement of GITR. Here, using combinations of CD4$^+$CD25$^+$ and CD4$^+$CD25$^-$ T cells from wild type and GITR$^{-/-}$ mice in coculture experiments, it was found that ligation of GITR on the CD4$^+$CD25$^-$ responder T cells, not the CD4$^+$CD25$^-$ suppressor T cells, was required to abrogate suppression. In the absence of CD4$^+$CD25$^+$ T cells, GITR$^{-/-}$ T cells mounted proliferative responses similar to those of wild type animals, although they were totally suppressed in the presence of physiological numbers of CD4$^+$CD25$^+$ T cells. These results suggest, for the first time, that GITR/GITRL engagement provides a previously undefined signal that renders effector T cells resistant to the inhibitory effects of CD4$^+$CD25$^+$ T cells. Thus, the downregulation of GITRL expression subsequent to secondary inflammatory signals may facilitate CD4$^+$CD25$^+$-mediated suppression and prevent the deleterious consequences of an exuberant effector cell response.

This research has shed new light on the mechanisms underlying the interaction of GITR and its ligand, GITRL, especially regarding the effects on CD4$^+$CD25$^-$ T cells, the cells traditionally understood to be the target of suppressive activity. In summary, using GITR$^{-/-}$ mice, the capacity of anti-GITR mAb (the agonistic mouse antibody to GITR) to abrogate suppression was demonstrated to be mediated by its action on CD4$^+$CD25$^+$, not CD4$^+$CD25$^+$ T cells (as previously proposed by several studies). APCs (antigen presenting cells) constitutively express GITRL, which is downregulated following Toll-like receptor signaling. Although GITR$^{-/-}$ mouse CD4$^+$CD25$^-$ T cells were capable of mounting proliferative responses, they were incapable of proliferation in the presence of physiological numbers of CD4$^+$CD25$^+$ T cells. Thus, GITRL provides an important signal for CD4$^+$CD25$^-$ T cells, and other effector T cells (e.g., CD8$^+$ T cells), rendering them resistant to CD4$^+$CD25$^+$-mediated regulation at the initiation of the immune response. The downregulation of GITRL by inflammatory stimuli may enhance the susceptibility of effector T cells (e.g., CD4$^+$CD25$^-$ T cells) to suppressor activity during the course of, e.g., cancer or an infectious insult.

To this end, the present invention provides the nucleotide and amino acid sequences of a novel mouse homolog of human GITRL. Human GITRL has been identified (Kwon et al. (1999) *J. Biol. Chem.* 274:6056-61; Gurney et al. (1999) *Curr. Biol.* 9:215-18); in addition, several groups very recently also reported the cloning of the murine GITR ligand (Kim et al., 2003; Tone et al., 2003; Yu et al., 2003).

In one aspect, the present invention provides nucleotide sequences, and amino acid sequences, and active fragments and/or fusion proteins thereof, of a novel mouse homolog of human GITRL. GITRL polynucleotides of the invention include polynucleotides that modulate expression of GITRL, e.g., expression vectors comprising GITRL polynucleotides that may upregulate expression of GITRL, and/or antisense and/or RNAi GITRL polynucleotides that downregulate the expression of GITRL. Use of such polynucleotides to modulate the expression of GITRL in cells and/or animals are also provided. In addition to GITRL polypeptides, the invention also provides other agonistic polypeptides, e.g., active fragments of GITRL and/or GITRL fusion proteins that are capable of mimicking GITRL, i.e., inducing GITR activity in effector T cells. Transformed host cells and transgenic animals containing GITRL polynucleotides are also within the scope of the invention.

In another aspect, antibodies that specifically bind to the novel murine GITRL polypeptides of the invention (i.e., do not bind to human GITRL) are provided. In particular, neutralizing antibodies that inhibit the activity of GITRL (e.g., antibodies that prevent GITRL from binding GITR) are provided; these antibodies can be said to neutralize the activity of GITRL (i.e., render GITRL ineffective). Neutralizing antibodies of the invention include nonhuman and human antibodies to GITRL that inhibit GITRL activity, as well as chimerized and/or humanized versions of nonhuman antibodies of the invention that inhibit GITRL activity. Also included within the scope of the invention are antagonistic antibodies that may have one or more mutations, which may function to increase the half-life, stability or affinity of the antibody, or may function to modify the effector function of the antibody.

Another aspect of the invention provides screening assays in which the GITRL polynucleotides and polypeptides, including but not limited to human homologs thereof, are used to identify compounds capable of modulating the activity of GITR in a cell, organism or subject. The invention also provides methods to assess the efficacy of identified compounds whereby the number of T cells in a patient is determined before and after administration of the identified compound. Additionally, the invention provides methods of treating patients or subjects using the identified compounds.

In addition to providing methods of screening test compounds capable of modulating GITR activity, e.g., GITR agonists or GITR antagonists, the invention provides methods for diagnosing, prognosing and monitoring the progress of disorders related to disregulation of the immune system, e.g., autoimmune diseases, inflammatory diseases and transplant rejection, and cancer and infectious diseases.

Methods for using GITRL and related molecules of the invention are also disclosed herein, including agonistic GITR molecules (i.e., GITRL polynucleotides, GITRL polypeptides, active fragments thereof and/or fusion proteins thereof, agonistic small molecules, and agonistic GITR antibodies), and antagonistic GITR molecules (i.e., GITRL inhibitory polynucleotides, neutralizing GITR antibodies, neutralizing GITRL antibodies, antagonistic small molecules, and GITR fusions proteins), for the therapeutic treatment of disorders related to disregulation of the immune system. For example, methods for treating a subject at risk for, or diagnosed with, an autoimmune disorder, transplant rejection, and/or other inflammatory diseases comprising administering GITR antagonists, e.g., a neutralizing anti-GITRL antibody to the subject are provided; also, methods of treating a subject at risk for, or diagnosed with, cancer or infectious diseases comprising administering GITR agonists, e.g., GITRL, or an agonistic fusion protein thereof, are provided. Alternatively, methods of inducing or inhibiting proliferation of T cells via the administration of GITR agonists, e.g., GITRL (including agonistic fusion proteins thereof), or GITR antagonists, e.g., neutralizing anti-GITRL antibodies or antagonistic GITR fusion proteins, respectively, are provided. Similarly, methods of blocking or enhancing suppression of T cells in the presence of $CD4^+CD25^+$ T cells comprising administration of GITR agonists, e.g., GITRL (including agonistic fusion proteins thereof), or GITR antagonists, e.g., neutralizing anti-GITRL antibodies, respectively, are also provided. T cell populations treated with GITRL polypeptides and related molecules (including agonistic fusion proteins thereof) are within the scope of the invention, and may be administered to a subject in a method of treating cancer or an infectious disease. Other methods of treatment are provided, including a method of treating a subject at risk for, or diagnosed with, an autoimmune disorder, an inflammatory disease, or transplant rejection with an antagonistic compound that decreases GITR activity, and methods of treating a subject at risk for, or diagnosed with, cancer or an infectious disease with an agonistic compound that increases GITR activity. Pharmaceutical compositions, e.g., vaccine adjuvants, comprising GITRL polynucleotides, polypeptides and related molecules (including agonistic GITRL fusion proteins and antagonistic anti-GITRL antibodies) of the invention are also within the scope of the invention. The methods of the present invention are directed to GITRL and GITR, including, but not limited to, mouse GITRL and GITR and their homologs; specifically included among these homologs is human GITRL and GITR.

GITRL Polynucleotides and Polypeptides

The present invention provides novel isolated and purified polynucleotides and polypeptides related to a novel ligand for GITR (GITRL). The genes, polynucleotides, proteins, and polypeptides of the present invention include, but are not limited to, mouse GITRL and its homologs.

For example, the invention provides purified and isolated polynucleotides encoding murine GITRL. Preferred DNA sequences of the invention include genomic, cDNA and chemically synthesized DNA sequences.

The nucleotide sequence of a cDNA encoding this novel ligand, designated mouse GITRL cDNA, is set forth in SEQ ID NO:1. Polynucleotides of the present invention also include polynucleotides that hybridize under stringent conditions to SEQ ID NO:1, or its complement, and/or encode polypeptides that retain substantial biological activity (i.e., active fragments) of full-length mouse GITRL. Polynucleotides of the present invention also include continuous portions of the sequence set forth in SEQ ID NO:1 comprising at least 21 consecutive nucleotides.

The nucleotide sequence of a genomic DNA encoding this novel ligand, designated mouse GITRL genomic DNA, is set forth in SEQ ID NO:3. Polynucleotides of the present invention also include polynucleotides that hybridize under stringent conditions to SEQ ID NO:3, or its complement, and/or encode polypeptides that retain substantial biological activity of full-length mouse GITRL. Polynucleotides of the present invention also include continuous portions of the sequence set forth in SEQ ID NO:3 comprising at least 21 consecutive nucleotides.

The amino acid sequence of mouse GITRL is set forth in SEQ ID NO:2. Polypeptides of the present invention also include continuous portions of the sequence set forth in SEQ ID NO:2 comprising at least 7 consecutive amino acids. A preferred polypeptide of the present invention includes any continuous portion of the sequence set forth in SEQ ID NO:2 that retains substantial biological activity of full-length mouse GITRL. Polynucleotides of the present invention also include, in addition to those polynucleotides of murine origin described above, polynucleotides that encode the amino acid sequence set forth in SEQ ID NO:2 or a continuous portion thereof, and that differ from the polynucleotides described above only due to the well-known degeneracy of the genetic code.

The isolated polynucleotides of the present invention may be used as hybridization probes and primers to identify and isolate nucleic acids having sequences identical to or similar to those encoding the disclosed polynucleotides. Hybridization methods for identifying and isolating nucleic acids include polymerase chain reaction (PCR), Southern hybridizations, in situ hybridization and Northern hybridization, and are well known to those skilled in the art.

Hybridization reactions can be performed under conditions of different stringency. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

| Stringency Condition | Polynucleotide Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1 × SSC -or- 42° C.; 1 × SSC, 50% formamide | 65° C.; 0.3 × SSC |
| B | DNA:DNA | <50 | $T_B^*$; 1 × SSC | $T_B^*$; 1 × SSC |
| C | DNA:RNA | >50 | 67° C.; 1 × SSC -or- 45° C.; 1 × SSC, 50% formamide | 67° C.; 0.3 × SSC |
| D | DNA:RNA | <50 | $T_D^*$; 1 × SSC | $T_D^*$; 1 × SSC |
| E | RNA:RNA | >50 | 70° C.; 1 × SSC -or- 50° C.; 1 × SSC, 50% formamide | 70° C.; 0.3 × SSC |
| F | RNA:RNA | <50 | $T_F^*$; 1 × SSC | $T_F^*$; 1 × SSC |
| G | DNA:DNA | >50 | 65° C.; 4 × SSC -or- 42° C.; 4 × SSC, 50% formamide | 65° C.; 1 × SSC |
| H | DNA:DNA | <50 | $T_H^*$; 4 × SSC | $T_H^*$; 4 × SSC |
| I | DNA:RNA | >50 | 67° C.; 4 × SSC -or- 45° C.; 4 × SSC, 50% formamide | 67° C.; 1 × SSC |
| J | DNA:RNA | <50 | $T_J^*$; 4 × SSC | $T_J^*$; 4 × SSC |
| K | RNA:RNA | >50 | 70° C.; 4 × SSC -or- 50° C.; 4 × SSC, 50% formamide | 67° C.; 1 × SSC |
| L | RNA:RNA | <50 | $T_L^*$; 2 × SSC | $T_L^*$; 2 × SSC |
| M | DNA:DNA | >50 | 50° C.; 4 × SSC -or- 40° C.; 6 × SSC, 50% formamide | 50° C.; 2 × SSC |
| N | DNA:DNA | <50 | $T_N^*$; 6 × SSC | $T_N^*$; 6 × SSC |
| O | DNA:RNA | >50 | 55° C.; 4 × SSC -or- 42° C.; 6 × SSC, 50% formamide | 55° C.; 2 × SSC |
| P | DNA:RNA | <50 | $T_P^*$; 6 × SSC | $T_P^*$; 6 × SSC |
| Q | RNA:RNA | >50 | 60° C.; 4 × SSC -or- 45° C.; 6 × SSC, 50% formamide | 60° C.; 2 × SSC |
| R | RNA:RNA | <50 | $T_R^*$; 4 × SSC | $T_R^*$; 4 × SSC |

[1] The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2] SSPE (1 × SSPE is 0.15M NaCl, 10 mM $NaH_2PO_4$, and 1.25 mM EDTA, pH 7.4) can be substituted for SSC (1 × SSC is 0.15M NaCl and 15 mM sodium citrate) in the hybridization and wash buffers; washes are performed for 15 minutes after hybridization is complete.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.) = 2(\# of A + T bases) + 4(\# of G + C bases)$. For hybrids between 18 and 49 basepairs in length, $T_m(° C.) = 81.5 + 16.6(\log_{10} Na^+) + 0.41(\% G + C) - (600/N)$, where N is the number of bases in the hybrid, and $Na^+$ is the concentration of sodium ions in the hybridization buffer ($Na^+$ for 1 × SSC = 0.165 M).
Additional examples of stringency conditions for polynucleotide hybridization are provided in Sambrook et al., Molecular Cloning: A Laboratory Manual, Chs. 9 & 11, Cold Spring Harbor Laboratory Press, Cold Spring Harbor, NY (1989), and Ausubel et al., eds., Current Protocols in Molecular Biology, Sects. 2.10 & 6.3-6.4, John Wiley & Sons, Inc. (1995), herein incorporated by reference.

The isolated polynucleotides of the present invention may be used as hybridization probes and primers to identify and isolate DNA having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides.

The isolated polynucleotides of the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least 50% sequence identity (more preferably, at least 75% identity; most preferably, at least 90% identity) with the disclosed polynucleotides, whereas polypeptide homologs have at least 30% sequence identity (more preferably, at least 45% identity; most preferably, at least 60% identity) with the disclosed polypeptides. Preferably, homologs of the disclosed polynucleotides and polypeptides are those isolated from mammalian species.

The isolated polynucleotides of the present invention may also be used as hybridization probes and primers to identify cells and tissues that express the polypeptides of the present invention and the conditions under which they are expressed.

Additionally, the isolated polynucleotides of the present invention may be used to alter (i.e., enhance, reduce, or modify) the expression of the genes corresponding to the polynucleotides of the present invention in a cell or organism. These corresponding genes are the genomic DNA sequences of the present invention (e.g., SEQ ID NO:3) that are transcribed to produce the mRNAs from which the cDNA polynucleotides of the present invention (e.g., SEQ ID NO:1) are derived.

Altered expression of the genes of the present invention, including but not limited to mouse GITRL and its homologs, may be achieved in a cell or organism through the use of various inhibitory polynucleotides, such as antisense polynucleotides (e.g., antisense GITRL nucleic acid molecules) and ribozymes that bind and/or cleave the mRNA transcribed from the genes of the invention (see, e.g., Galderisi et al. (1999) *J. Cell Physiol*. 181:251-57; Sioud (2001) *Curr. Mol. Med*. 1:575-88). Such inhibitory polynucleotides may be useful in preventing or treating autoimmune disorders, inflammatory diseases, transplant rejection, and similar or related disorders.

The antisense polynucleotides or ribozymes of the invention can be complementary to an entire coding strand of a gene of the invention, or to only a portion thereof. Alternatively, antisense polynucleotides or ribozymes can be complementary to a noncoding region of the coding strand of a gene of the invention. The antisense polynucleotides or ribozymes can be constructed using chemical synthesis and enzymatic ligation reactions using procedures well known in the art. The nucleoside linkages of chemically synthesized polynucleotides can be modified to enhance their ability to resist nuclease-mediated degradation, as well as to increase their sequence specificity. Such linkage modifications include, but are not limited to, phosphorothioate, methylphosphonate, phosphoroamidate, boranophosphate, morpholino, and peptide nucleic acid (PNA) linkages (Galderisi et al., supra; Heasman (2002) *Dev. Biol*. 243:209-14; Micklefield (2001) *Curr. Med. Chem*. 8:1157-79). Alternatively, these molecules can be produced biologically using an expression vector into which a polynucleotide of the present invention has been subcloned in an antisense (i.e., reverse) orientation.

The inhibitory polynucleotides of the present invention also include triplex-forming oligonucleotides (TFOs) that bind in the major groove of duplex DNA with high specificity and affinity (Knauert and Glazer (2001) *Hum. Mol. Genet*. 10:2243-51). Expression of the genes of the present invention can be inhibited by targeting TFOs complementary to the regulatory regions of the genes (i.e., the promoter and/or enhancer sequences) to form triple helical structures that prevent transcription of the genes.

In one embodiment of the invention, the inhibitory polynucleotides of the present invention are short interfering RNA (siRNA) molecules (e.g., siRNA GITRL nucleic acid molecules). These siRNA molecules are short (preferably 19-25 nucleotides; most preferably 19 or 21 nucleotides), double-stranded RNA molecules that cause sequence-specific degradation of target mRNA. This degradation is known as RNA interference (RNAi) (e.g., Bass (2001) *Nature* 411:428-29). Originally identified in lower organisms, RNAi has been effectively applied to mammalian cells and has recently been shown to prevent fulminant hepatitis in mice treated with siRNA molecules targeted to Fas mRNA (Song et al. (2003) *Nature Med*. 9:347-51). In addition, intrathecally delivered siRNA has recently been reported to block pain responses in two models (agonist-induced pain model and neuropathic pain model) in the rat (Dorn et al. (2004) *Nucleic Acids Res*. 32(5):e49).

The siRNA molecules of the present invention can be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) *Proc. Natl. Acad. Sci. USA* 99:6047-52). The siRNA molecules can be chemically synthesized (Elbashir et al. (2001) *Nature* 411:494-98) or produced by in vitro transcription using single-stranded DNA templates (Yu et al., supra). Alternatively, the siRNA molecules can be produced biologically, either transiently (Yu et al., supra; Sui et al. (2002) *Proc. Natl. Acad. Sci. USA* 99:5515-20) or stably (Paddison et al. (2002) *Proc. Natl. Acad. Sci. USA* 99:1443-48), using an expression vector(s) containing the sense and antisense siRNA sequences. Recently, reduction of levels of target mRNA in primary human cells, in an efficient and sequence-specific manner, was demonstrated using adenoviral vectors that express hairpin RNAs, which are further processed into siRNAs (Arts et al. (2003) *Genome Res*. 13:2325-32).

The siRNA molecules targeted to the polynucleotides of the present invention can be designed based on criteria well known in the art (e.g., Elbashir et al. (2001) *EMBO J*. 20:6877-88). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; and the target segment preferably should be in the ORF region of the target mRNA and preferably should be at least 75 bp after the initiation ATG and at least 75 bp before the stop codon. Based on these criteria, or on other known criteria (e.g., Reynolds et al. (2004) *Nature Biotechnol.* 22:326-30), siRNA molecules of the present invention, targeted to the mRNA polynucleotides of the present invention, can be designed by one of ordinary skill in the art.

Altered expression of the genes of the present invention in an organism may also be achieved through the creation of nonhuman transgenic animals into whose genomes polynucleotides of the present invention have been introduced. Such transgenic animals include animals that have multiple copies of a gene (i.e., the transgene) of the present invention. A tissue-specific regulatory sequence(s) may be operably linked to the transgene to direct expression of a polypeptide of the present invention to particular cells or a particular developmental stage. Methods for generating transgenic animals via embryo manipulation and microinjection, particularly animals such as mice, have become conventional and are well known in the art (e.g., Bockamp et al., *Physiol. Genomics*, 11:115-32 (2002)).

Altered expression of the genes of the present invention in an organism may also be achieved through the creation of animals whose endogenous genes corresponding to the polynucleotides of the present invention have been disrupted through insertion of extraneous polynucleotide sequences (i.e., a knockout animal). The coding region of the endogenous gene may be disrupted, thereby generating a nonfunctional protein. Alternatively, the upstream regulatory region of the endogenous gene may be disrupted or replaced with different regulatory elements, resulting in the altered expression of the still-functional protein. Methods for generating knockout animals include homologous recombination and are well known in the art (e.g., Wolfer et al., *Trends Neurosci.*, 25:336-40 (2002)).

The isolated polynucleotides of the present invention may be operably linked to an expression control sequence and/or ligated into an expression vector for recombinant production of the polypeptides of the present invention. General methods of expressing recombinant proteins are well known in the art. Such recombinant proteins may be expressed in soluble form for use in treatment of disorders resulting from disregulation of the immune system; such disorders include, for example, cancers and infectious diseases, and autoimmune disorders and inflammatory diseases, and transplant rejection. Autoimmune disorders and inflammatory diseases include, but are not limited to, rheumatoid arthritis, encephalomyelitis, osteoarthritis, multiple sclerosis, autoimmune gastritis, systemic lupus erythematosus, psoriasis and other inflammatory dermatoses, type I diabetes, asthma, allergy, and inflammatory bowel diseases, including Crohn's disease and ulcerative colitis.

An expression vector, as used herein, is intended to refer to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as recombinant expression vectors (or simply, expression vectors). In general, expression vectors of utility in recombinant DNA techniques are often in the form of plasmids. In the present specification, plasmid and vector may be used interchangeably as the plasmid is the most commonly used form of vector. However, the invention is intended to include other forms of expression vectors, such as viral vectors (e.g., replication defective retroviruses, adenoviruses and adeno-associated viruses) that serve equivalent functions.

In one embodiment, the polynucleotides of the present invention are used to create GITR agonists, e.g., GITRL polypeptides, including active fragments and/or fusion polypeptides thereof, which are also within the scope of the invention. For example, a GITRL polypeptide or active fragments thereof may be fused to a second moiety, e.g., an immunoglobulin or a fragment thereof (e.g., an Fc binding fragment thereof). In some embodiments, the first polypeptide includes full-length GITRL polypeptide. Alternatively, the first polypeptide may comprise less than the full-length GITRL polypeptide. Additionally, soluble forms of GITRL may be fused through "linker" sequences to the Fc portion of an immunoglobulin. Other fusions proteins, such as those with glutathione-S-transferase (GST), Lex-A, thioredoxin (TRX) or maltose-binding protein (MBP), may also be used.

The fusion proteins may additionally include a linker sequence joining the GITRL or GITRL fragment to the second moiety. Use of such linker sequences are well known in the art. For example, the fusion protein can include a peptide linker, e.g., a peptide linker of about 2 to 20, more preferably less than 10, amino acids in length. In one embodiment, the peptide linker may be 2 amino acids in length.

In another embodiment, the fusion protein includes a heterologous signal sequence (i.e., a polypeptide sequence that is not present in a polypeptide encoded by a GITRL nucleic acid) at its N-terminus. For example, a signal sequence from another protein may be fused with a GITRL polypeptide, including active fragments and/or fusion proteins thereof. In certain host cells (e.g., mammalian host cells), expression and/or secretion of GITRL can be increased through use of a heterologous signal sequence.

A signal peptide that can be included in the fusion protein is MKFLVNVALVFMVVYISYIYA (SEQ ID NO:11). If desired, one or more amino acids can additionally be inserted between the first polypeptide moiety comprising the GITRL moiety and the second polypeptide moiety. The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second GITRL polypeptide. In preferred embodiments, the second polypeptide includes at least a region of an immunoglobulin polypeptide. Immunoglobulin fusion polypeptide are known in the art and are described in e.g., U.S. Pat. Nos. 5,516,964; 5,225,538; 5,428,130; 5,514,582; 5,714,147; and 5,455,165, all of which are hereby incorporated by reference.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A GITRL-encoding nucleic acid can be cloned into such an expression vector such that the fusion moiety is linked in-frame to the immunoglobulin protein. In some embodiments, GITRL fusion polypeptides exist as oligomers, such as dimers or trimers.

A number of cell lines may act as suitable host cells for recombinant expression of the polypeptides of the present invention. Mammalian host cell lines include, for example, COS cells, CHO cells, 293T cells, A431 cells, 3T3 cells, CV-1 cells, HeLa cells, L cells, BHK21 cells, HL-60 cells, U937 cells, HaK cells, Jurkat cells, as well as cell strains derived from in vitro culture of primary tissue and primary explants.

Alternatively, it may be possible to recombinantly produce the polypeptides of the present invention in lower eukaryotes such as yeast or in prokaryotes. Potentially suitable yeast strains include *Saccharomyces cerevisiae, Schizosaccharomycespombe, Kluyveromyces* strains, and *Candida* strains. Potentially suitable bacterial strains include *Escherichia coli, Bacillus subtilis*, and *Salmonella typhimurium*. If the polypeptides of the present invention are made in yeast or bacteria, it may be necessary to modify them by, for example, phosphorylation or glycosylation of appropriate sites, in order to obtain functionality. Such covalent attachments may be accomplished using well-known chemical or enzymatic methods.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are disclosed in Kohno (1990) *Meth. Enzymol.* 185:187-95. EP 0433225, and patent application U.S. Ser. No. 08/163,877 describe other appropriate methods.

The polypeptides of the present invention may also be recombinantly produced by operably linking the isolated polynucleotides of the present invention to suitable control sequences in one or more insect expression vectors, such as baculovirus vectors, and employing an insect cell expression system. Materials and methods for baculovirus/Sf9 expression systems are commercially available in kit form (e.g., the MaxBac® kit, Invitrogen, Carlsbad, Calif.).

GITR agonists, e.g., GITRL protein, active fragments and/or fusion protein thereof, may be prepared by growing a culture transformed host cells under culture conditions necessary to express the desired protein. Following recombinant expression in the appropriate host cells, the polypeptides of the present invention may then be purified from culture medium or cell extracts using known purification processes, such as gel filtration and ion exchange chromatography. Soluble forms of GITR agonists, e.g., GITRL protein, active fragments and/or fusion protein thereof, can be purified from conditioned media. Membrane-bound forms of, e.g., a GITRL protein of the invention can be purified by preparing a total membrane fraction from the expressing cell and extracting the membranes with a nonionic detergent such as Triton X-100. Purification may also include affinity chromatography with agents known to bind the polypeptides of the present invention. These purification processes may also be used to purify the polypeptides of the present invention from other sources, including natural sources. As previously described, GITR agonists, e.g., GITRL protein, active fragments and/or fusion protein thereof, may also be expressed as a product of transgenic animals, e.g., as a component of the milk of transgenic cows, goats, pigs, or sheep, which are characterized by somatic or germ cells containing a polynucleotide sequence encoding the GITR agonists.

The methods that may be used to purify GITR agonists, e.g., GITRL protein, active fragments and/or fusion protein thereof, are known to those skilled in the art. For example, a GITRL protein of the invention may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of GITR agonists, e.g., GITRL protein, active fragments and/or fusion protein thereof, from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the GITRL protein. Affinity columns including antibodies to the GITRL protein can also be used in purification in accordance with known methods. Some or all of the foregoing purification steps, in various combinations or with other known methods, can also be employed to provide a substantially purified isolated recombinant protein. Preferably, the isolated GITRL protein is purified so that it is substantially free of other mammalian proteins.

Alternatively, GITR agonists, e.g., GITRL protein, active fragments and/or fusion protein thereof, may also be recombinantly expressed in a form that facilitates purification. For example, the polypeptides may be expressed as fusions with proteins such as maltose-binding protein (MBP), glutathione-S-transferase (GST), or thioredoxin (TRX). Kits for expression and purification of such fusion proteins are commercially available from New England BioLabs (Beverly, Mass.), Pharmacia (Piscataway, N.J.), and Invitrogen, respectively. GITR agonists, e.g., GITRL protein, active fragments and/or fusion protein thereof, can also be tagged with a small epitope and subsequently identified or purified using a specific antibody to the epitope. A preferred epitope is the FLAG epitope, which is commercially available from Eastman Kodak (New Haven, Conn.).

GITR agonists, e.g., GITRL protein, active fragments and/or fusion protein thereof, may also be produced by known conventional chemical synthesis. Methods for chemically synthesizing such polypeptides are well known to those skilled in the art. Such chemically synthetic polypeptides may possess biological properties in common with the natural, purified polypeptides, and thus may be employed as biologically active or immunological substitutes for the natural polypeptides.

GITR agonists, e.g., GITRL protein, active fragments and/or fusion protein thereof, also encompass molecules that are structurally different from the disclosed polypeptides (e.g., which have a slightly altered sequence), but which have substantially the same biochemical properties as the disclosed polypeptides (e.g., are changed only in functionally nonessential amino acid residues). Such molecules include naturally occurring allelic variants and deliberately engineered variants containing alterations, substitutions, replacements, insertions, or deletions. Techniques for such alterations, substitutions, replacements, insertions, or deletions are well known to those skilled in the art. In some embodiments, the GITRL polypeptide moiety is provided as a variant GITRL polypeptide having mutations in the naturally occurring GITRL sequence (wild type) that results in a GITRL sequence more resistant to proteolysis (relative to the nonmutated sequence).

The methods disclosed herein for the generation of GITR agonists, e.g., GITRL, active fragments thereof and/or fusion proteins thereof, may be used to generate GITR antagonists, especially soluble GITR proteins, active fragments thereof and/or fusion proteins thereof. One of skill in the art will recognize that to generate GITR antagonists, e.g., soluble GITR, active fragments thereof, and/or fusion proteins thereof, all that would be required is the nucleic acid sequence or amino acid sequence of GITR, both of which are known. Using these sequences, GITR antagonists, e.g., soluble GITR, active fragments thereof, and/or fusion proteins thereof, may be generated using recombinant DNA techniques and/or chemical synthesis, as described above.

Anti-GITRL Antibodies

In other embodiments, the invention provides GITR antagonists as antibodies, or antigen binding fragments thereof, that specifically bind to GITRL, preferably, mammalian (e.g., murine) GITRL, and neutralize GITR activity.

One of skill in the art will recognize that as used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" ("FR"). The extent of the FRs and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are hereby incorporated by reference). Each VH and VL is composed of three CDRs and four FRs, arranged from amino-terminus to carboxy-terminus in the following order: FR1, CDR1, FR2, CDR2, FR3, CDR3, FR4.

The antibody can further include a heavy and light chain constant region to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1 q) of the classical complement system.

Immunoglobulin refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd, or 214 amino acids) are encoded by a variable region gene at the NH2-terminus (about 110 amino acids) and a kappa or lambda constant region gene at the COOH-terminus. Full-length immunoglobulin "heavy chains" (about 50 Kd, or 446 amino acids), are similarly encoded by a variable region gene (about 116 amino acids) and one of the other aforementioned constant region genes, e.g., gamma (encoding about 330 amino acids). The immunoglobulin heavy chain constant region genes encode for the antibody class, i.e., isotype (e.g., IgM or IgG1). The antigen binding fragment of an antibody (or simply "antibody portion," or "fragment"), as used herein, refers to one or more fragments of a full-length antibody that retain the ability to specifically bind to an antigen (e.g., CD3). Examples of binding fragments encompassed within the term "antigen binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-46), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-26; and Huston et al. (1988) Proc. Natl. Acad. Sci. USA 85:5879-83). Such single chain antibodies are also intended to be encompassed within the term "antigen binding fragment" of an antibody. These antibody fragments are obtained using conventional techniques known to those skilled in the art, and the fragments are screened for utility in the same manner as are intact antibodies.

One of skill in the art will recognize that the methods disclosed herein for generation of antibody molecules to the polypeptides of the present invention, e.g., murine GITRL, may also be used to generate antibody molecules to other proteins, e.g., GITR or human GITRL. Consequently, the methods for generating antibody molecules apply not only to the polypeptides of the present invention as disclosed, but also to, for example, GITR or human GITRL.

Antibody molecules to the polypeptides of the present invention, e.g., neutralizing antibodies to murine GITRL, including but not limited to mouse GITRL and its homologs, may be useful in preventing or treating autoimmune disorders, inflammatory diseases, transplant rejections, and similar or related disorders. Other antibody molecules e.g., agonistic GITR antibodies, may be useful in the methods of the invention for treating cancer, infectious diseases, and similar and related disorders. Such antibody molecules may be produced by methods well known to those skilled in the art. For example, monoclonal antibodies can be produced by generation of hybridomas in accordance with known methods. Hybridomas formed in this manner are then screened using standard methods, such as enzyme-linked immunosorbent assay (ELISA), to identify one or more hybridomas that produce an antibody that specifically binds with the polypeptides of the present invention. For example, GITRL proteins of the invention may also be used to immunize animals to obtain polyclonal and monoclonal antibodies that specifically react with the GITRL protein and which may inhibit binding of ligands to the receptor, i.e., GITR. Similarly, GITR proteins may also be used to obtain polyclonal and monoclonal antibodies that specifically react with GITR. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in Merrifield (1963) *J. Amer. Chem. Soc.* 85:2149-54; Krstenansky et al. (1987) *FEBS Lett.* 211:10. A full-length polypeptide of the present invention may be used as the immunogen, or, alternatively, antigenic peptide fragments of the polypeptides may be used. An antigenic peptide of a polypeptide of the present invention comprises at least 7 continuous amino acid residues and encompasses an epitope such that an antibody raised against the peptide forms a specific immune complex with the polypeptide. Preferably, the antigenic peptide comprises at least 10 amino acid residues, more preferably at least 15 amino acid residues, even more preferably at least 20 amino acid residues, and most preferably at least 30 amino acid residues.

Monoclonal antibodies may be generated by other methods known to those skilled in the art of recombinant DNA technology. As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention (e.g., GITRL) or with GITR, to thereby isolate immunoglobulin library members that bind to the polypeptides of the present invention, or to GITR, respectively. Techniques and commercially available kits for generating and screening phage display libraries are well known to those skilled in the art. Additionally, examples of methods and reagents particularly amenable for use in generating and screening antibody display libraries can be found in the literature. For example, the "combinatorial antibody display" method has been developed to identify and isolate antibody fragments having a particular antigen specificity, and can be utilized to produce monoclonal antibodies (for descriptions of combinatorial antibody display, see, e.g., Sastry et al. (1989) *Proc. Natl. Acad. Sci. USA* 86:5728; Huse et al. (1989) *Science* 246:1275; Orlandi et al. 1989 *Proc. Natl. Acad. Sci. USA* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers to a conserved 3' constant region can be used for PCR amplification of the heavy and light chain variable regions from a number of murine antibodies (Larrick et al. (1991) *Biotechniques* 11: 152-56). A similar strategy can also been used to amplify human heavy and light chain variable regions from human antibodies (Larrick et al. (1991) *Methods: Companion to Methods in Enzymology* 2:106-10).

Polyclonal sera and antibodies may be produced by immunizing a suitable subject with a polypeptide of the present invention. The antibody titer in the immunized subject may be monitored over time by standard techniques, such as with ELISA using immobilized marker protein. If desired, the antibody molecules directed against a polypeptide of the present invention may be isolated from the subject or culture media and further purified by well-known techniques, such as protein A chromatography, to obtain an IgG fraction.

Fragments of antibodies to the polypeptides of the present invention may be produced by cleavage of the antibodies in accordance with methods well known in the art. For example, immunologically active Fab and F(ab')$_2$ fragments may be generated by treating the antibodies with an enzyme such as pepsin.

Additionally, chimeric, humanized, and single-chain antibodies to the polypeptides of the present invention, comprising both human and nonhuman portions, may be produced using standard recombinant DNA techniques and/or a recombinant combinatorial immunoglobulin library. Humanized antibodies may also be produced using transgenic mice which are incapable of expressing endogenous immunoglobulin heavy and light chain genes, but which can express human heavy and light chain genes. For example, human monoclonal antibodies (mAbs) directed against GITRL may be generated using transgenic mice carrying the human immunoglobulin genes rather than murine immunoglobulin genes. Splenocytes from these transgenic mice immunized with the antigen of interest may then be used to produce hybridomas that secrete human mabs with specific affinities for epitopes from a human protein (see, e.g., Wood et al., WO 91/00906; Kucherlapati et al., WO 91/10741; Lonberg et al. WO 92/03918; Kay et al., WO 92/03917; Lonberg et al. (1994) *Nature* 368:856-59; Green et al. (1994) *Nat. Genet.* 7:13-21; Morrison et al. (1994) *Proc. Natl. Acad. Sci. USA* 81:6851-55; Bruggeman (1993) *Year Immunol* 7:33-40; Tuaillon et al. (1993) *Proc. Natl. Acad. Sci. USA* 90:3720-24; Bruggeman et al. (1991) *Eur. J. Immunol.* 21:1323-26).

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, European Patent Application 171,496; Morrison et al., European Patent Application 173,494; Neuberger et al., WO 86/01533; Cabilly et al., U.S. Pat. No. 4,816,567; Cabilly et al., European Patent Application 125,023; Better et al. (1988) *Science* 240:1041-43; Liu et al. (1987) *Proc. Natl. Acad. Sci. USA* 84:3439-43; Liu et al. (1987) *J. Immunol.* 139:3521-26; Sun et al. (1987) *Proc. Natl. Acad. Sci. USA* 84:214-18; Nishimura et al. (1987) *Cancer Res.* 47:999-1005; Wood et al. (1985) *Nature* 314:446-49; and Shaw et al. (1988) *J. Natl. Cancer Inst.* 80:1553-59).

An antibody or an immunoglobulin chain may be humanized by methods known in the art. Humanized antibodies, including humanized immunoglobulin chains, may be generated by replacing sequences of the Fv variable region that are not directly involved in antigen binding with equivalent sequences from human Fv variable regions. General methods for generating humanized antibodies are provided by Morrison (1985) *Science* 229:1202-07; Oi et al. (1986) *BioTechniques* 4:214; Queen et al., U.S. Pat. Nos. 5,585,089; 5,693, 761; 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid sequences are well known to those skilled in the art and, for example, may be obtained from a hybridoma producing an antibody against a predetermined target. The recombinant DNA encoding the humanized antibody, or fragment thereof, can then be cloned into an appropriate expression vector.

For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or an aromatic nonpolar residue such as phenylalanine, tyrosine, tryptophan or alanine (see, e.g., U.S. 5,624,821).

Anti-GITRL antibodies of the invention may be useful for isolating, purifying, and/or detecting GITRL polypeptides in supernatant, cellular lysate, or on the cell surface. Antibodies disclosed in this invention can be also used diagnostically to monitor GITRL protein levels as part of a clinical testing procedure, or clinically to target a therapeutic modulator to a cell or tissue comprising the antigen of the GITRL antibody. For example, a therapeutic such as a small molecule, or other therapeutic of the invention can be linked to the GITRL antibody in order to target the therapeutic to the cell or tissue expressing GITRL. Neutralizing or nonneutralizing antibodies (preferably monoclonal antibodies) binding to GITRL protein may also be useful in the treatment of conditions involving disregulation of the immune system, e.g., autoimmune diseases. These neutralizing monoclonal antibodies may be capable of blocking GITRL binding to GITR. The present invention further provides compositions comprising an antibody that specifically reacts with GITRL. Similarly, anti-GITR antibodies may be useful in isolating, purifying and/or detecting GITR, diagnostically monitoring GITR levels, or clinically targeting a therapeutic modulator to a cell or tissue comprising GITR. Agonistic antibodies to GITR (preferably monoclonal antibodies) may also be useful in the treatment of conditions involving disregulation of the immune system e.g., cancer or infectious diseases. These agonistic antibodies may be capable of inducing GITR activity. Thus the present invention further provides compositions comprising an antibody to GITR.

GITRL Screening Assays

The polynucleotides and polypeptides of the present invention may be used in screening assays to identify pharmacological agents or lead compounds for agents that are capable of modulating the activity of GITRL, and thereby GITR, in a cell or organism, and are thereby potential regulators of immune Humanized or CDR-grafted antibody molecules or immunoglobulins may be produced by CDR grafting or CDR substitution, wherein one, two, or all CDRs of an immunoglobulin chain can be replaced. See, e.g., U.S. Pat. No. 5,225,539; Jones et al. (1986) *Nature* 321:552-25; Verhoeyan et al. (1988) *Science* 239:1534; Beidler et al. (1988) *J. Immunol.* 141:4053-60; Winter, U.S. Pat. No. 5,225,539, the contents of all of which are hereby incorporated by reference. Winter describes a CDR-grafting method that may be used to prepare the humanized antibodies of the present invention (UK Patent Application GB 2188638A; Winter, U.S. Pat. No. 5,225,539), the contents of which are hereby incorporated by reference. All of the CDRs of a particular human antibody may be replaced with at least a portion of a nonhuman CDR, or only some of the CDRs may be replaced with nonhuman CDRs. It is only necessary to replace the number of CDRs required for binding of the humanized antibody to a predetermined antigen.

Monoclonal, chimeric and humanized antibodies that have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability, or affinity of the antibody, or a constant region from another species or antibody class; or (iii) by modifying one or more amino acids in the constant region to alter, for example, the number of glycosylation sites, effector cell function, Fc receptor (FcR) binding, complement fixation, etc.

Methods for altering an antibody constant region are known in the art. Antibodies with altered function, e.g. altered affinity for an effector ligand, such as FcR on a cell, or the C1 component of complement, can be produced by replacing at least one amino acid residue in the constant portion of the antibody with a different residue (see, e.g., EP 388,151 A1, U.S. Pat. No. 5,624,821 and U.S. Pat. No. 5,648,260, the contents of all of which are hereby incorporated by reference). Similar types of alterations to the murine (or other species') immunoglobulin may be applied to reduce or eliminate these functions. Such alterations are known in the art. responses. For example, samples containing GITRL (either natural or recombinant) can be contacted with one of a plurality of test compounds (either biological agents or small organic molecules), and the activity of GITRL in each of the treated samples can be compared with the activity of GITRL in untreated samples or in samples contacted with different test compounds. Such comparisons will determine whether any of the test compounds results in: 1) a substantially decreased level of expression or activity of GITRL, thereby indicating an inhibitor of GITRL (e.g., a compound that restores or enhances immune suppression), or 2) a substantially increased level of expression or activity of GITRL, thereby indicating an activator of GITRL (e.g., a compound that reverses immune suppression). In one embodiment, the identification of test compounds capable of modulating GITRL activity is performed using high-throughput screening assays, such as BIACORE® (Biacore International AB, Uppsala, Sweden), BRET (bioluminescence resonance energy transfer), and FRET (fluorescence resonance energy transfer) assays, as well as ELISA and cell-based assays.

Small Molecules

Decreased GITR activity in an organism (or subject) afflicted with (or at risk for) autoimmune disorders, inflammatory diseases, or transplant rejection, or in a cell from such an organism (or subject) involved in such disorders, may also be achieved through the use of small molecules (usually organic small molecules) that antagonize, i.e., inhibit the activity of, GITR. Novel antagonistic small molecules may be identified by the screening methods described above and may be used in the treatment methods of the present invention described below. Conversely, increased GITR activity in an organism (or subject) afflicted with (or at risk for) cancer or infectious disease, or in a cell from such an organism (or subject) involved in such disorders, may also be achieved through the use of small molecules (usually organic small molecules) that agonize, i.e., enhance the activity of, GITR. Novel agonistic small molecules may be identified by the screening methods described above and may be used in the methods of treating cancer and/or infectious disease as described below.

Methods for Diagnosing, Prognosing, and Monitoring the Progress of Autoimmune Disorders and Cancers It is well known in the art that immunological mechanisms studied in animal models, particularly murine models, may be and often are, translatable to the human immune system. As such, although the Examples disclosed herein demonstrate the role of GITR in immune suppression by $CD4^+CD25^+$ regulatory cells in a murine model, the disclosed methods for diagnosing, prognosing, and monitoring disorders related to disregulation of the immune system, e.g., autoimmune disorders, inflammatory disorders and transplant rejection, and cancer and infectious disease, will be particularly useful for diagnosing, prognosing and monitoring such disorders in humans. In practicing the disclosed methods, a skilled artisan will recognize that the human homologs of GITR and GITRL, as well as human GITR agonists and antagonists, may be used in the claimed methods of diagnosing, prognosing, and monitoring such disorders in humans.

The present invention provides methods for diagnosing, prognosing, and monitoring the progress of autoimmune disorders in a subject (e.g., that directly or indirectly involve increases in the levels of GITRL) by detecting an upregulation of GITR activity, e.g., by detecting the upregulation of GITRL, including but not limited to the use of such methods in human subjects. One of skill in the art will recognize that these methods can apply to inflammatory diseases and transplant rejection as well. These methods may be performed by utilizing prepackaged diagnostic kits comprising at least one of the group comprising GITRL polynucleotide or fragments thereof, GITRL polypeptide or portions thereof (including fusion proteins thereof), or antibodies to GITRL polypeptides or derivatives thereof, or modulators of GITRL polynucleotides and/or polypeptides as described herein, which may be conveniently used, for example, in a clinical setting. In addition, one of skill in the art would recognize that the upregulation of GITRL could also be detected by indirect methods, such as counting the number of immune cells.

"Diagnostic" or "diagnosing" means identifying the presence or absence of a pathologic condition. Diagnostic methods include detecting upregulation of GITRL by determining a test amount of GITRL gene product (e.g., mRNA, cDNA, or polypeptide, including fragments thereof) in a biological sample from a subject (human or nonhuman mammal), and comparing the test amount with a normal amount or range (i.e., an amount or range from an individual(s) known not to suffer from autoimmune disorders) for the GITRL gene product. Although a particular diagnostic method may not provide a definitive diagnosis of autoimmune disorders, it suffices if the method provides a positive indication that aids in diagnosis.

The present invention also provides methods for prognosing such autoimmune disorders by detecting the upregulation of GITR activity, e.g., by detecting upregulation of GITRL.

"Prognostic" or "prognosing" means predicting the probable development and/or severity of a pathologic condition. Prognostic methods include determining the test amount of a GITRL gene product in a biological sample from a subject, and comparing the test amount to a prognostic amount or range (i.e., an amount or range from individuals with varying severities of autoimmune disorders) for the GITRL gene product. Various amounts of the GITRL gene product in a test sample are consistent with certain prognoses for autoimmune disorders. The detection of an amount of GITRL gene product at a particular prognostic level provides a prognosis for the subject.

The present invention also provides methods for monitoring the progress or course of such autoimmune disorders by detecting the upregulation of GITR activity, e.g., by detecting upregulation of GITRL. Monitoring methods include determining the test amounts of a GITRL gene product in biological samples taken from a subject at a first and second time, and comparing the amounts. A change in amount of GITRL gene product between the first and second times indicates a change in the course of autoimmune disorders, with a decrease in amount indicating remission of autoimmune disorders, and an increase in amount indicating progression of autoimmune disorders. Such monitoring assays are also useful for evaluating the efficacy of a particular therapeutic intervention in patients being treated for autoimmune disorders.

Increased expression of GITRL in methods outlined above can be detected in a variety of biological samples, including bodily fluids (e.g., whole blood, plasma, and urine), cells (e.g., whole cells, cell fractions, and cell extracts), and tissues. Biological samples also include sections of tissue, such as biopsies and frozen sections taken for histological purposes. Preferred biological samples include blood, plasma, lymph, tissue biopsies, urine, CSF (cerebrospinal fluid), synovial fluid, and BAL (bronchoalveolar lavage). It will be appreciated that analysis of a biological sample need not necessarily require removal of cells or tissue from the subject. For example, appropriately labeled agents that bind GITRL gene products (e.g., antibodies, nucleic acids) can be administered to a subject and visualized (when bound to the target) using standard imaging technology (e.g., CAT, NMR (MRI), and PET).

In the diagnostic and prognostic assays of the present invention, the GITRL gene product is detected and quantified to yield a test amount. The test amount is then compared with a normal amount or range. An amount significantly above the normal amount or range is a positive sign in the diagnosis of autoimmune disorders. Particular methods of detection and quantitation of GITRL gene products are described below.

Normal amounts or baseline levels of GITRL gene products can be determined for any particular sample type and population. Generally, baseline (normal) levels of GITRL protein or MRNA are determined by measuring the amount of GITRL protein or mRNA in a biological sample type from normal (i.e., healthy) subjects. Alternatively, normal values of GITRL gene product can be determined by measuring the amount in healthy cells or tissues taken from the same subject from which the diseased (or possibly diseased) test cells or tissues were taken. The amount of GITRL gene product (either the normal amount or the test amount) can be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values of GITRL gene product because relative values are sufficient for many applications of these methods. It will also be appreciated that in addition to the quantity or abundance of GITRL gene products, variant or abnormal GITRL gene products or their expression patterns (e.g., mutated transcripts, truncated polypeptides) may be identified by comparison to normal gene products and expression patterns.

The diagnostic, prognostic, and monitoring assays of the present invention involve detecting and quantifying GITRL gene products in biological samples. GITRL gene products include GITRL mRNA and GITRL polypeptide, and both can be measured using methods well known to those skilled in the art.

For example, GITRL mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention are based on the nucleic acid sequence of GITRL and are well known in the art.

Alternatively, GITRL mRNA can be amplified before detection and quantitation. Such amplification-based assays are well known in the art and include polymerase chain reaction (PCR), reverse-transcription-PCR (RT-PCR), PCR-enzyme-linked immunosorbent assay (PCR-ELISA), and ligase chain reaction (LCR). Primers and probes for producing and detecting amplified GITRL gene products (e.g., mRNA or cDNA) may be readily designed and produced without undue experimentation by those of skill in the art based on the nucleic acid sequence of GITRL. Amplified GITRL gene products may be directly analyzed, for example, by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that whichever amplification method is used, a variety of quantitative methods known in the art (e.g., quantitative PCR) may be used if quantitation of GITRL gene products is desired.

GITRL polypeptide (or fragments thereof) can be detected using various well-known immunological assays employing the anti-GITRL antibodies described above. Immunological assays refer to assays that utilize an antibody (e.g., polyclonal, monoclonal; chimeric, humanized, scFv, and fragments thereof) that specifically binds to GITRL polypeptide (or a fragment thereof). Such well-known immunological assays suitable for the practice of the present invention include ELISA, radioimmunoassay (RIA), immunoprecipitation, immunofluorescence, fluorescence-activated cell sorting (FACS), and Western blotting. GITRL polypeptide can also be detected using labeled GITR.

One of skill in the art will understand that the aforementioned methods can be applied to autoimmune disorders and other disorders (such as inflammatory diseases), including, but not limited to, rheumatoid arthritis, osteoarthritis, multiple sclerosis, autoimmune gastritis, systemic lupus erythematosus, psoriasis and other inflammatory dermatoses, type I diabetes, asthma, allergy, and inflammatory bowel diseases, including Crohn's disease and ulcerative colitis.

One of skill in the art will also recognize that the aforementioned methods or variations thereupon can also be used for diagnosing, prognosing, and monitoring the progress of various cancers and infectious diseases in a subject (e.g., that directly or indirectly involve decreases in the levels of GITRL) by detecting a downregulation of GITR activity, e.g., by detecting the downregulation of GITRL, including but not limited to the use of such methods in human subjects.

Uses of GITRL and Related Molecules in Therapy

Applicants believe they are the first to recognize that binding of GITR on effector T cells by GITRL, or other GITR agonists, provides a costimulatory signal to effector T cells, wherein such signal renders the effector T cells less susceptible to suppression by $CD4^+CD25^+$ regulatory T cells and increases the ability of effector T cells to proliferate in response to anti-CD3 or other activating signals. Although the murine model was used to uncover the mechanism, it is well known in the art that immunological mechanisms studied in murine models, may be and often are, translatable to the human immune system. As such, the disclosed methods for using GITRL and related molecules, i.e., GITR agonists or GITR antagonists, to treat disorders related to the disregulation of the of the immune system, e.g., autoimmune disorders, inflammatory disorders and transplant rejection, and cancer and infectious disease, will be particularly useful for treating such disorders in humans. In practicing the disclosed methods, a skilled artisan will recognize that the human homologs of GITR and GITRL, as well as human GITR agonists and antagonists, may be used in the claimed methods of using GITRL and GITRL-related proteins, i.e., GITR agonists and antagonists, in treating autoimmune disorders, inflammatory disorders and transplant rejection, and cancer and infectious diseases in humans.

The GITRL-related molecules disclosed herein, i.e., GITR agonists and antagonists, including modulators of GITRL polynucleotide and/or polypeptide activity identified using the methods described above, can be used in vitro, ex vivo, or incorporated into pharmaceutical compositions and administered to individuals in vivo to treat, for example, autoimmune disorders by administration of a GITR antagonist (e.g., GITRL inhibitory polynucleotides, antagonistic small molecules, neutralizing anti-GITR antibodies, and/or neutralizing anti-GITRL antibodies), or, e.g., cancers by administration of a GITR agonist (e.g., GITRL polynucleotides, GITRL polypeptides, or fusion proteins thereof, agonistic small molecules and/or agonistic anti-GITR antibodies). Such GITRL and/or related molecules (including modulators) include, but are not limited to, mouse GITRL and its homologs (and antibodies to such molecules), and such homologs include, but are not limited to, human GITRL. Several pharmacogenomic approaches to be considered in determining whether to administer GITRL and/or GITRL related molecules are well known to one of skill in the art and include genome-wide association, candidate gene approach, and gene expression profiling. A pharmaceutical composition of the invention is formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

GITR agonists or antagonists may be used as pharmaceutical compositions when combined with a pharmaceutically acceptable carrier. Such a composition may contain, in addition to the GITR agonists or antagonists and carrier, various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-14, IL-15, G-CSF, stem cell factor, and erythropoietin. The pharmaceutical composition may also include anticytokine antibodies as described in more detail below. The pharmaceutical composition may contain thrombolytic or antithrombotic factors such as plasminogen activator and Factor VIII. The pharmaceutical composition may further contain other anti-inflammatory agents as described in more detail below. Such additional factors and/or agents may be included in the pharmaceutical composition to produce a synergistic effect with GITR agonists or antagonists, or to minimize side effects caused by the GITR agonists or antagonists. Conversely GITR agonists or antagonists may be included in formulations of the particular cytokine, lymphokine, other hematopoietic factor, thrombolytic or antithrombotic factor, or anti-inflammatory agent to minimize side effects of the cytokine, lymphokine, other hematopoietic factor, thrombolytic or antithrombotic factor, or anti-inflammatory agent.

The pharmaceutical composition of the invention may be in the form of a liposome in which GITR agonists or antagonists are combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, etc. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are hereby incorporated by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a GITR agonist (e.g., a GITRL polynucleotide or GITRL polypeptide expressed therefrom) or a GITR antagonist (e.g., a neutralizing anti-GITRL antibody or a neutralizing anti-GITR antibody) is administered to a subject, e.g., a mammal (e.g., a human). A GITR agonist or antagonist may be administered in accordance with the method of the invention either alone or in combination with other therapies, such as treatments employing cytokines, lymphokines or other hematopoietic factors, or anti-inflammatory agents. When coadministered with one or more agents, GITR agonists or antagonists may be administered either simultaneously with the second agent, or sequentially. If administered sequentially, the attending physician will decide on the appropriate sequence of administering, e.g., a GITRL polypeptide (or fusion protein thereof) or neutralizing anti-GITRL antibody in combination with other agents.

When a therapeutically effective amount of a GITR agonist or antagonist is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition contains from about 0.5 to 90% by weight of the binding agent, and preferably from about 1 to 50% by weight of the binding agent.

When a therapeutically effective amount of a GITR agonist or antagonist is administered by intravenous, cutaneous or subcutaneous injection, the GITR agonist or antagonist will be in the form of a pyrogen-free, parenterally acceptable aqueous solution. The preparation of such parenterally acceptable protein solutions, having due regard to pH, isotonicity, stability, and the like, is within the skill of those in the art. A preferred pharmaceutical composition for intravenous, cutaneous, or subcutaneous injection should contain, in addition to the GITR agonist or antagonist, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of a GITR agonist or antagonist in the pharmaceutical composition of the present invention will depend upon the nature and severity of the condition being treated, and on the nature of prior treatments that the patient has undergone. Ultimately, the attending physician will decide the amount of GITR agonist or antagonist with which to treat each individual patient. Initially, the attending physician will administer low doses of GITR agonist or antagonist and observe the patient's response. Larger doses of GITR agonist or antagonist may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of e.g., GITRL polypeptide or neutralizing anti-GITRL antibody per kg body weight.

The duration of intravenous (i.v.) therapy using a pharmaceutical composition of the present invention will vary, depending on the severity of the disease being treated and the condition and potential idiosyncratic response of each individual patient. It is contemplated that the duration of each application of the GITR agonist or antagonist may be in the range of 12 to 24 hours of continuous i.v. administration. Also contemplated is subcutaneous (s.c.) therapy using a pharmaceutical composition of the present invention. These therapies can be administered daily, weekly, or, more preferably, biweekly, or monthly. It is also contemplated that where the GITR agonist or antagonist is a small molecule, the therapies may be administered daily, twice a day, three times a day, etc.

Ultimately the attending physician will decide on the appropriate duration of i.v. or s.c. therapy, or therapy with a small molecule, and the timing of administration of the therapy, using the pharmaceutical composition of the present invention.

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Uses of GITRL and other GITR Agonists to Enhance an Immune Response

In one aspect, the present invention provides methods for increasing immune cell, e.g., T cell (e.g., an effector T cell) proliferation by contacting an immune cell or a population of immune cells with a GITR agonist, e.g., a GITRL polynucleotide or polypeptide of the invention (e.g., a fusion protein thereof) and/or an agonistic anti-GITR antibody, which potentiates or enhances the activity of GITR. These methods are based, at least in part, on the finding that an agonistic anti-GITR antibody reversed $CD4^+CD25^+$ T cell-mediated suppression of $CD4^+CD25^-$ T cell proliferation (Example 5). The methods are also based, in part, on the finding that GITR binding by, e.g., GITRL or an agonistic anti-GITR antibody, induces proliferation of effector T cells (e.g., $CD4^+CD25^-$ and $CD8^+$ T cells) (Example 9 and Example 13). Applicants also showed that GITR binding by GITRL provides a costimulatory signal to effector T cells (e.g., $CD4^+$ and $CD8^+$ T cells), thereby increasing the abilities of effector T cells to overcome suppression mediated by $CD4^+CD25^+$ regulatory T cells and proliferate in response to anti-CD3 (Examples 11 and 13); i.e., binding of GITR expressed on effector T cells by GITR agonists (e.g., GITRL polypeptide, active fragments thereof, and/or agonistic anti-GITR antibody) renders effector T cells less susceptible to suppression by $CD4^+CD25^+$ regulatory T cells. Accordingly, GITR agonists that stimulate the GITR activity in effector T cells can be used by themselves or in combination with an antigen, e.g., as an adjuvant (e.g., a vaccine adjuvant), to upregulate an immune response in vivo, e.g., for use in treating cancer and infectious disorders.

In one embodiment, GITR agonists (e.g., GITRL polynucleotides, polypeptides, active fragments and/or fusion proteins thereof, agonistic small molecules and/or agonistic anti-GITR antibodies) may be useful in the treatment of various immune deficiencies and disorders (including severe combined immunodeficiency (SCID)), e.g., in upregulating growth and proliferation of T cells. These immune deficiencies may be genetic or be caused by viral (e.g., HIV) as well as bacterial or fungal infections, or may result from autoimmune disorders. More specifically, infectious diseases causes by viral, bacterial, fingal or other infection may be treatable using a protein of the present invention, including infections by HIV, hepatitis viruses, herpesviruses, mycobacteria, *Leishmania* spp., *malaria* spp. and various fungal infections such as candidiasis. Of course, in this regard, a protein of the present invention may also be useful where a boost to the immune system generally may be desirable, i.e., in the treatment of cancer.

Upregulation of antigen presenting cell (APC) antigens (e.g., upregulation of B7.1, B7.2, and B7.3), as a means of upregulating immune responses, may also be useful in therapy. Upregulation of immune responses may be in the form of enhancing an existing immune response or eliciting an initial immune response. For example, enhancing an immune response through stimulating dendritic cell antigen presenting functions may be useful in cases of viral infection. In addition, systemic viral diseases such as influenza, the common cold, and encephalitis might be alleviated by the administration of stimulatory forms antigen presenting molecules, e.g., dendritic cell antigens, systemically.

Alternatively, antiviral immune responses may be enhanced in an infected patient by removing T cells from the patient, costimulating the T cells ex vivo with viral antigen-pulsed professional APCs (e.g., B cells, macrophages and/or dendritic cells) and GITR agonists (e.g., GITRL polynucleotides, polypeptides, active fragments and/or fusion proteins thereof, agonistic small molecules and/or agonistic anti-GITR antibodies). GITR agonists (e.g., GITRL polynucleotides, polypeptides, active fragments and/or fusion proteins thereof, and/or agonistic anti-GITR antibodies) may be supplied either as soluble protein or as expressed by the APCs. Another method of enhancing antiviral immune responses would be to isolate infected cells from a patient, transfect them with a nucleic acid encoding a GITRL protein of the present invention as described herein, such that the cells express all or a portion of the protein on their surface, and reintroduce the transfected cells into the patient. The infected cells would now be capable of delivering a costimulatory signal to effector T cells in vivo, i.e., expression of GITRL protein, or an active fragment thereof, by the infected cell, and binding of such GITRL protein to GITR on effector T cells could render the effector T cells less susceptible to suppression by $CD4^+CD25^+$ regulatory T cells.

In another application, upregulation or enhancement of an APC antigen function may be useful in the induction of tumor immunity. Tumor cells (e.g., sarcoma, melanoma, lymphoma, leukemia, neuroblastoma, and carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a GITR agonist (e.g., GITR polypeptides, active fragments and/or fusion proteins thereof, and/or agonistic anti-GITR antibodies), alone or in combination with a peptide having B7.2-like activity alone, or in conjunction with a peptide having B7.1-like activity, etc. The transfected tumor cells are returned to the patient to result in expression of the peptides on the surface of the transfected cell. Alternatively, gene therapy techniques can be used to target a tumor cell for transfection in vivo.

The presence of a GITR agonist (e.g., a GITRL polypeptide, active fragments and/or fusion proteins thereof, an agonistic small molecule and/or an agonistic anti-GITR antibody), in combination with a peptide having the activity of an APC antigen (e.g., B7.1, B7.2, etc) on the surface of the tumor cell provides the necessary costimulatory signals to T cells to induce a T cell-mediated immune response against the transfected tumor cells. In addition, tumor cells which lack MHC class I or MHC class II molecules, or which fail to reexpress sufficient amounts of MHC class I or MHC class II molecules, can be transfected with nucleic acids encoding all or a portion (e.g., a cytoplasmic-domain truncated portion) of an MHC class I a chain protein and $\beta_2$ microglobulin protein or an MHC class II a chain protein and an MHC class II $\beta$ chain protein (or corresponding human HLA nucleic acids) to thereby express MHC class I or MHC class II proteins (or corresponding HLA molecules) on the cell surface. Expression of the appropriate class I or class II MHC in conjunction with a GITR agonist (e.g., a GITRL polypeptide, active fragments and/or fusion proteins thereof, and/or an agonistic anti-GITR antibody), and/or a peptide having the activity of an APC antigen (e.g., B7.1, B7.2, etc.) induces a T cell-mediated immune response against the transfected tumor cell. Optionally, a gene encoding an antisense construct which blocks expression of an MHC class II-associated protein, such as the invariant chain, can also be cotransfected with a DNA encoding a GITR agonist (e.g., a GITRL polypeptide, active fragment thereof, a fusion protein thereof, and/or an agonistic anti-GITR antibody) and/or a peptide having the activity of an APC antigen to promote presentation of tumor associated antigens and induce tumor specific immunity. Thus, the induction of a T cell-mediated immune response in a human subject may be sufficient to overcome tumor-specific tolerance in the subject.

In other embodiments, GITR agonists (e.g., GITRL polypeptides, active fragments and/or fusion proteins thereof, fusion proteins thereof, agonistic small molecules, and/or agonistic anti-GITR antibodies) of the invention may be used as vaccine adjuvants. Adjuvants are immune modulating compounds that have the ability to enhance and/or steer the development and profile of immune responses against various antigens that are themselves poorly immunogenic. Cytokines and/or lymphokines can be used as adjuvants. The appropriate selection of adjuvants can induce good humoral and cellular immune responses that would not develop in the absence of adjuvant. In particular, adjuvants have significant effects in enhancing the immune response to subunit and peptide antigens in vaccines. Their stimulatory activity is also beneficial to the development of antigen-specific immune responses directed against protein antigens. For a variety of antigens that require strong mucosal responses, high serum titers, induction of CTL (cytotoxic T lymphocytes) and vigorous cellular responses, adjuvant and cytokine/lymphokine combinations provide stimuli that are not provided by most antigen preparations.

As used herein, the phrase "vaccine adjuvant" or "vaccine therapy" is intended to mean the use of a GITR agonist (e.g., a GITRL polynucleotide, GITRL polypeptide, an active fragment thereof, a fusion protein thereof, and/or an agonistic anti-GITR antibody), in combination with an antigen (e.g., viral, parasitic and bacterial polypeptides, proteins or peptides), or other antigens (e.g., tumor or cancer cell polypeptides, proteins or peptides) or polynucleotides encoding the antigen to enhance, suppress or otherwise modulate an immune response to the antigen. For the purpose of this definition, "combination" shall mean use in conjunction with, simultaneous with (combined or uncombined) or sequentially with an antigen.

The term "vaccine adjuvant composition" refers to a vaccine adjuvant that additionally includes immunologically acceptable diluents or carriers in a conventional manner to prepare injectable liquid solutions or suspensions. The vaccine adjuvant composition may additionally include agents that further enhance an immune response elicited by a GITR agonist. For example, the vaccine adjuvant composition may additionally include 3-O-deacylated monophosphoryl lipid A (MPL®; Corixa Corporation, Seattle, Wash.) or monophosphoryl lipid A and derivatives and analogs thereof. MPL® can be used in a range of 1-100 μg/dose.

The antigens used for vaccine therapy include proteins, peptides or polypeptides derived from immunogenic and nonimmunogenic proteins, as well as any of the following: saccharides, proteins, polynucleotides or oligonucleotides, or other macromolecular components, or fragments thereof. As used in this section, a "peptide" comprises a series of at least six amino acids and contains at least one antigenic determinant, while a "polypeptide" is a longer molecule than a peptide, but does not constitute a full-length protein. As used herein, a "fragment" comprises a portion, but less than all of a saccharide, protein, polynucleotides or oligonucleotide, or other macromolecular components.

As used herein, the term "effective adjuvanting amount" means a dose of the combination of adjuvants described herein, which is suitable to elicit an increased immune response in a vertebrate host. The particular dosage will depend in part upon the age, weight and medical condition of the host, as well as on the method of administration and the antigen.

The vaccine adjuvant composition of the invention can be administered to a human or nonhuman vertebrate by a variety of routes, including, but not limited to, intranasal, oral, vaginal, rectal, parenteral, intradermal, transdermal (see, e.g., International application WO 98/20734, which is hereby incorporated by reference), intramuscular, intraperitoneal, subcutaneous, intravenous and intraarterial. The amount of the antigen component or components of the antigenic composition will vary depending in part upon the identity of the antigen, as well as upon the age, weight and medical condition of the subject, as well as on the method of administration. Again, suitable doses are readily determined by persons skilled in the art. It is preferable, although not required, that the antigen and the combination of adjuvants be administered at the same time. The number of doses and the dosage regimen for the antigenic composition are also readily determined by persons skilled in the art. In some instances, the adjuvant properties of the combination of adjuvants may reduce the number of doses needed or the time course of the dosage regimen.

The combinations of adjuvants of this invention are suitable for use in combination with wide variety of antigens from a wide variety of pathogenic microorganisms, including but not limited to those from viruses, bacteria, fingi or parasitic microorganisms that infect humans and nonhuman vertebrates, or from a cancer cell or tumor cell (e.g., sarcoma, melanoma, lymphoma, leukemia, neuroblastoma, and carcinoma). The antigen may comprise peptides or polypeptides derived from proteins, as well as fragments of any of the following: saccharides, proteins, polynucleotides or oligonucleotides, cancer or tumor cells, or other macromolecular components. In some instances, more than one antigen is included in the antigenic composition.

Desirable viral vaccines containing the adjuvant combinations of this invention include those directed to the prevention and/or treatment of disease caused by, without limitation, Human immunodeficiency virus, Simian immunodeficiency virus, Respiratory syncytial virus, Parainfluenza virus types 1-3, Influenza virus, Herpes simplex virus, Human cytomegalovirus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, rinderpest virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

Desirable bacterial vaccines containing the adjuvant combinations of this invention include those directed to the prevention and/or treatment of disease caused by, without limitation, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium* intracellular complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*.

Desirable vaccines against fungal pathogens containing the adjuvant combinations of this invention include those directed to the prevention and/or treatment of disease caused by, without limitation, *Aspergillis, Blastomyces, Candida, Coccidiodes, Cryptococcus* and *Histoplasma*.

Desirable vaccines against parasites containing the adjuvant combinations of this invention include those directed to the prevention and/or treatment of disease caused by, without limitation, *Leishmania major, Ascaris, Trichuris, Giardia, Schistosoma, Cryptosporidium, Trichomonas, Toxoplasma gondii* and *Pneumocystis carinii*.

Desirable vaccines for eliciting a therapeutic or prophylactic anticancer effect in a vertebrate host, which contain the adjuvant combinations of this invention, include those utilizing a cancer antigen or tumor-associated antigen including, without limitation, prostate specific antigen (PSA), prostate-specific membrane antigen (PSMA), carcino-embryonic antigen (CEA), MUC-1, Her2, CA-125, MAGE-3, EGFR, HELP, GCC, CD66-c, prostasin, TMPRSS3, TADG 12 and TADG 15.

In the case of HIV and SIV, the antigenic compositions comprise at least one protein, polypeptide, peptide or fragment derived from said virus. In some instances, multiple HIV or SIV proteins, polypeptides, peptides and/or fragments are included in the antigenic composition.

The adjuvant combination formulations of this invention are also suitable for inclusion as an adjuvant in polynucleotide vaccines (also known as DNA vaccines). Such vaccines may further include facilitating agents such as bupivicaine (see U.S. Pat. No. 5,593,972, which is hereby incorporated by reference).

Methods of 1) stimulating antigen presenting cell function, e.g., dendritic cell functions; 2) removing T cells from the patient, costimulating them ex vivo, and reintroducing them into the subject; 3) transfecting tumor cells to induce tumor immunity; and 4) using vaccine adjuvants are well known in the art (see, e.g., Cerundolo et al. (2004) Dendritic cells: a journey from laboratory to clinic. *Nat. Immunol.* 5(1):7-10; Ko et al. (2003) Immunotherapy of malignant diseases. *Int. Arch. Allergy Immunol.* 132:294-309; Valmori et al. (1999) An antigen-targeted approach to adoptive transfer therapy of cancer. *Cancer Res.* 59:2167-73).

Uses of GITR Antagonists to Decrease Immune Cell Activity

In yet another aspect, the invention features a method for maintaining the susceptibility of effector T cells, e.g., $CD4^+$ and $CD8^+$ T cells, or a population thereof, to suppression by $CD4^+CD25^+$ regulatory T cells. The method may comprise contacting a population of T cells with a GITR antagonist (e.g., GITRL inhibitory polynucleotides, an antagonistic small molecule, a neutralizing anti-GITR antibody, and/or a neutralizing anti-GITRL antibody) in an amount sufficient to inhibit the activity of the immune cell or population. Antagonists of GITR may also be administered to subjects for whom suppression of an immune response is desired. These conditions include, e.g., autoimmune disorders (e.g., arthritic disorders), inflammatory diseases, or organ transplantation.

These methods are based, at least in part, on the finding that reduction of GITR activity, e.g., by using a neutralizing anti-GITRL antibody, restores $CD4^+CD25^+$-mediated suppression (Example 13), i.e., neutralizing anti-GITRL antibody maintains the susceptibility of effector T cells, e.g., $CD4^+$ and $CD8^+$ T cells, to suppression by $CD4^+CD25^+$ regulatory T cell. Additionally, applicants have demonstrated that incubation of effector T cells with neutralizing anti-GITRL antibody ameliorates disease in murine experimental autoimmune encephalitis (EAE) (Example 14). Accordingly, GITR antagonists, i.e., molecules that inhibit GITR activity (e.g., anti-GITRL antibodies) may be used to maintain the susceptibility of effector T cells to suppression by $CD4^+CD25^+$ T cells in vivo, e.g., for treating or preventing immune cell-associated pathologies, including transplant rejection, inflammatory diseases, and autoimmune disorders.

The methods of using GITR antagonists may also be used inhibit the activity (e.g., proliferation, differentiation, survival) of an effector T cell, and thus, can be used to treat or prevent a variety of immune disorders. Nonlimiting examples of the disorders that can be treated or prevented include, but are not limited to, transplant rejection, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, spondyoarthropathy, ankylosing spondylitis, intrinsic asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, and allergy such as, atopic allergy. Preferred disorders that can be treated using methods which comprise the administration of GITR antagonists, e.g., a neutralizing GITRL antibody, include arthritic disorders (e.g., rheumatoid arthritis, juvenile rheumatoid arthritis, osteoarthritis, psoriatic arthritis, and ankylosing spondylitis (preferably, rheumatoid arthritis)), multiple sclerosis, type I diabetes, lupus (SLE), IBD, Crohn's disease, asthma, vasculitis, allergy, scleroderma and psoriasis.

In another embodiment, GITR antagonists, alone or in combination with, other therapeutic agents as described herein (e.g., TNF antagonists) can be used to treat multiple myeloma and related B lymphocytic malignancies (Brenne, A. et al. (2002) *Blood* 99(10):3756-62).

Using GITR antagonists (e.g., GITRL inhibitory polynucleotides, antagonistic small molecules, and/or neutralizing antibodies to GITR and/or GITRL), it is possible to modulate immune responses in a number of ways. Downregulation may be in the form of inhibiting or blocking an immune response already in progress, or may involve preventing the induction of an immune response. The functions of activated T cells may be inhibited by enhancing the suppression of T cell responses, or by inducing specific tolerance in T cells, or both. Immunosuppression of T cell responses is generally an active, non-antigen-specific, process that requires continuous exposure of the T cells to the suppressive agent. Tolerance, which involves inducing nonresponsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Downregulating or preventing one or more functions of an antigen presenting cell antigen (e.g., B7.1), and thus preventing high level lymphokine synthesis by activated T cells will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a GITR antagonist (e.g., GITRL inhibitory polynucleotides, an antagonistic small molecule, a neutralizing anti-GITR antibody, and/or a neutralizing anti-GITRL antibody), in combination with a molecule which inhibits or blocks interaction of a B7 lymphocyte antigen with its natural ligand(s) on immune cells (such as a soluble, monomeric form of a peptide having B7.2 activity alone or in conjunction with a monomeric form of a peptide having an activity of another B lymphocyte antigen (e.g., B7.1) or blocking antibody), prior to transplantation can lead to the binding of the molecule to the natural ligand(s) on the immune cells without transmitting the corresponding costimulatory signal. Blocking B7 lymphocyte antigen function in this manner prevents cytokine synthesis by immune cells, such as effector T cells, and thus acts as an immunosuppressant. Moreover, the lack of costimulation may also be sufficient to anergize the T cells, thereby inducing tolerance in a subject. Induction of long-term tolerance by B7 lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogenic cardiac grafts in rats and xenogenic pancreatic islet cell grafts in mice, both of which have been used to examine the immunosuppressive effects of CTLA4Ig fusion proteins in vivo as described in Lenschow et al. (1992) *Science* 257: 789-92 and Turka et al. (1992) *Proc. Natl. Acad. Sci. USA* 89:11102-05. In addition, murine models of GVHD (see, e.g., Paul, ed., Fundamental Immunology, Raven Press, New York, 1989, pp. 846-47) can be used to determine the effect of blocking B lymphocyte antigen function in vivo on the development of that disease.

Blocking the function of an APC antigen may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of GITR antagonists (e.g., GITRL inhibitory polynucleotides, antagonistic small molecules, and/or neutralizing antibodies to GITR and/or GITRL) in combination with reagents that block costimulation of T cells by disrupting receptor:ligand interactions of APC antigens can be used to inhibit T cell activation and prevent production of autoantibodies or T cell-derived cytokines that may be involved in the disease process. Additionally, GITR antagonists (e.g., GITRL inhibitory polynucleotides, antagonistic small molecules, and/or neutralizing antibodies to GITR and/or GITRL) in combination with blocking reagents may induce antigen-specific tolerance of autoreactive T cells, which could lead to long-term relief from the disease. The efficacy of these agents in preventing or alleviating autoimmune disorders can be determined using a number of well-characterized animal models of human autoimmune diseases. Examples include murine experimental autoimmune encephalitis (EAE), systemic lupus erythematosis in MRL/lpr/lpr mice or NZB hybrid mice, murine autoimmune collagen arthritis, diabetes mellitus in NOD mice and BB rats, and murine experimental myasthenia gravis (see, e.g., Paul, ed., Fundamental Immunology, Raven Press, New York, 1989, pp. 840-56).

In one embodiment, GITR antagonists (e.g., GITRL inhibitory polynucleotides, antagonistic small molecules, and/or neutralizing antibodies to GITR and/or GITRL), including pharmaceutical compositions thereof, are administered in combination therapy, i.e., combined with other agents, e.g., therapeutic agents, that are useful for treating pathological conditions or disorders, such as immune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more GITR antagonists (e.g., GITRL inhibitory polynucleotides, antagonistic small molecules, and/or neutralizing antibodies to GITR and/or GITRL), coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more GITR antagonists (e.g., GITRL inhibitory polynucleotides, antagonistic small molecules, and/or neutralizing antibodies to GITR and/or GITRL) described herein may be used in combination with two or more of the therapeutic agents described herein. Such combination therapies may advantageously utilize lower dosages of the administered therapeutic agents, thus avoiding possible toxicities or complications associated with the various monotherapies. Moreover, the therapeutic agents disclosed herein act on pathways that differ from the GITRL receptor pathway, and thus are expected to enhance and/or synergize with the effects of the GITR antagonists, i.e. wherein effector T cells maintain their susceptibility to suppression by $CD4^+CD25^+$ regulatory T cells.

Preferred therapeutic agents used in combination with a GITRL antagonist are those agents that interfere at different stages in the autoimmune and subsequent inflammatory response. In one embodiment, one or more GITR antagonists (e.g., GITRL inhibitory polynucleotides, antagonistic small molecules, and/or neutralizing antibodies to GITR and/or GITRL) described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof. Nonlimiting examples of the agents that can be used in combination with the GITR antagonists (e.g., GITRL inhibitory polynucleotides, antagonistic small molecules, and/or neutralizing antibodies to GITR and/or GITRL) described herein, include, but are not limited to, antagonists of one or more interleukins (ILs) or their receptors, e.g., antagonists of IL-1, IL-2, IL-6, IL-7, IL-8, IL-12, IL-13, IL-15, IL-16, IL-18, and IL-22; antagonists of cytokines or growth factors or their receptors, such as tumor necrosis factor (TNF), LT, EMAP-II, GM-CSF, FGF and PDGF. GITR antagonists (e.g., GITRL inhibitory polynucleotides, antagonistic small molecules, and/or neutralizing antibodies to GITR and/or GITRL) can also be combined with inhibitors of, e.g., antibodies to, cell surface molecules such as CD2, CD3, CD4, CD8, CD25, CD28, CD30, CD40, CD45, CD69, CD80 (B7.1), CD86 (B7.2), CD90, or their ligands, including CD154 (gp39 or CD40L), or LFA-1/ICAM-1 and VLA-4/VCAM-1 (Yusuf-Makagiansar et al. (2002) *Med. Res. Rev.* 22:146-67). Preferred antagonists that can be used in combination with GITR antagonists (e.g., GITRL inhibitory polynucleotides, antagonistic small molecules, and/or neutralizing antibodies to GITR and/or GITRL) described herein include antagonists of IL-1, IL-12, TNFa, IL-15, IL-17, IL-18, and IL-22.

Examples of those agents include IL-12 antagonists, such as chimeric, humanized, human or in vitro-generated antibodies (or antigen binding fragments thereof) that bind to IL-12 (preferably human IL-12), e.g., the antibody disclosed in WO 00/56772; IL-12 receptor inhibitors, e.g., antibodies to human IL-12 receptor; and soluble fragments of the IL-12 receptor, e.g., human IL-12 receptor. Examples of IL-15 antagonists include antibodies (or antigen binding fragments thereof) against IL-15 or its receptor, e.g., chimeric, humanized, human or in vitro-generated antibodies to human IL-15 or its receptor, soluble fragments of the IL-15 receptor, and IL-15-binding proteins. Examples of IL-18 antagonists include antibodies, e.g., chimeric, humanized, human or in vitro-generated antibodies (or antigen binding fragments thereof), to human IL-18, soluble fragments of the IL-18 receptor, and IL-18 binding proteins (IL-18BP, Mallet et al. (2001) *Circ. Res.* 28). Examples of IL-1 antagonists include Interleukin-1-converting enzyme (ICE) inhibitors, such as Vx740, IL-1 antagonists, e.g., IL-1RA (Anikinra, Amgen), sIL1RII (Immunex), and anti-IL-1 receptor antibodies (or antigen binding fragments thereof).

Examples of TNF antagonists include chimeric, humanized, human or in vitro-generated antibodies (or antigen binding fragments thereof) to TNF (e.g., human TNFa), such as D2E7, (human TNFa antibody, U.S. Pat. No. 6,258,562), CDP-571/CDP-870/BAY-10-3356 (humanized anti-TNFa antibody; Celltech/Pharmacia), cA2 (chimeric anti-TNFa antibody; Remicade™, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, Enbrel™; Immunex; see, e.g., *Arthritis & Rheumatism* (1994) 37:S295; *J. Invest. Med.* (1996) 44:235A), p55 kdTNFR-IgG (55 kD TNF receptor-IgG fusion protein (Lenercept)); enzyme antagonists, e.g., TNFa converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see e.g., *Arthritis & Rheumatism* (1996) 39(9)(supplement):S284; *Amer. J. Physiol.-Heart and Circulatory Physiology* (1995) 268:37-42). Preferred TNF antagonists are soluble fragments of the TNF receptors, e.g., p55 or p75 human TNF receptors or derivatives thereof, e.g., 75 kdTNFR-IgG, and TNFa converting enzyme (TACE) inhibitors.

In other embodiments, the GITR antagonists described herein can be administered in combination with one or more of the following: IL-13 antagonists, e.g., soluble IL-13 receptors (sIL-13) and/or antibodies against IL-13; IL-2 antagonists, e.g., DAB 486-IL-2 and/or DAB 389-IL-2 (IL-2 fusion proteins; Seragen; see, e.g., *Arthritis & Rheumatism* (1993) 36:1223), and/or antibodies to IL-2R, e.g., anti-Tac (humanized anti-IL-2R; Protein Design Labs, *Cancer Res.* (1990) 50(5):1495-502). Yet another combination includes GITR antagonists (e.g., GITRL inhibitory polynucleotides, antagonistic small molecules, and/or neutralizing antibodies to GITR and/or GITRL) in combination with nondepleting anti-CD4 inhibitors (IDEC-CE9.1/SB 210396; nondepleting primatized anti-CD4 antibody; IDEC/SmithKline). Yet other preferred combinations include antagonists of the costimulatory pathway CD80 (B7.1) or CD86 (B7.2), including antibodies, soluble receptors or antagonistic ligands; as well as p-selectin glycoprotein ligand (PSGL), anti-inflammatory cytokines, e.g., IL-4 (DNAX/Schering); IL-10 (SCH 52000; recombinant IL-10 DNAX/Schering); IL-13 and TGF-β, and agonists thereof (e.g., agonist antibodies).

In other embodiments, one or more GITR antagonists can be coformulated with, and/or coadministered with, one or more anti-inflammatory drugs, immunosuppressants, or metabolic or enzymatic inhibitors. Nonlimiting examples of the drugs or inhibitors that can be used in combination with the GITR antagonists (e.g., GITRL inhibitory polynucleotides, antagonistic small molecules, and/or neutralizing antibodies to GITR and/or GITRL) described herein, include, but are not limited to, one or more of: nonsteroidal anti-inflammatory drug(s) (NSAIDs), e.g., ibuprofen, tenidap (see, e.g., *Arthritis & Rheumatism* (1996) 39(9)(supplement): S280)), naproxen (see, e.g., *Neuro. Report* (1996) 7:1209-13), meloxicam, piroxicam, diclofenac, and indomethacin; sulfasalazine (see, e.g., *Arthritis & Rheumatism* (1996) 39(9) (supplement):S281); corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl]methylamino]benzoyl]-L-glutamic acid); and inhibitors of pyrimidine biosynthesis, e.g., dihydroorotate dehydrogenase (DHODH) inhibitors (e.g., leflunomide (see, e.g., *Arthritis & Rheumatism* (1996) Vol. 39, No. 9 (supplement), S131; *Inflammation Research* (1996) 45:103-07). Preferred therapeutic agents for use in combination with GITR antagonists (e.g., GITRL inhibitory polynucleotides, antagonistic small molecules, and/or neutralizing antibodies to GITR and/or GITRL) include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppresants, e.g., cyclosporin, tacrolimus (FK-506); and mTOR inhibitors, e.g., sirolimus (rapamycin) or rapamycin derivatives, e.g., soluble rapamycin derivatives (e.g., ester rapamycin derivatives, e.g., CCI-779 (Elit (2002) *Current Opinion Investig. Drugs* 3(8):1249-53; Huang et al. (2002) *Current Opinion Investig. Drugs* 3(2):295-304); agents which interfere with signaling by proinflammatory cytokines such as TNFa or IL-1 (e.g. IRAK, NIK, IKK, p38 or MAP kinase inhibitors); COX2 inhibitors, e.g., celecoxib, rofecoxib, and variants thereof, see, e.g., *Arthritis & Rheumatism* (1996) Vol. 39, No. 9 (supplement), S81); phosphodiesterase inhibitors, e.g., R973401 (phosphodiesterase Type IV inhibitor; see, e.g., *Arthritis & Rheumatism* (1996) Vol. 39, No. 9 (supplement), S282)); phospholipase inhibitors, e.g., inhibitors of cytosolic phospholipase 2 (cPLA2) (e.g., trifluoromethyl ketone analogs (U.S. Pat. No. 6,350,892)); inhibitors of vascular endothelial cell growth factor or growth factor receptor, e.g., VEGF inhibitor and/or VEGF-R inhibitor; and inhibitors of angiogenesis. Preferred therapeutic agents for use in combination with GITR antagonists (e.g., GITRL inhibitory polynucleotides, antagonistic small molecules, and/or neutralizing antibodies to GITR and/or GITRL) are immunosuppresants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with a GITRL antagonist include one or more of: 6-mercaptopurines (6-MP); azathioprine sulphasalazine; mesalazine; olsalazine chloroquinine/hydroxychloroquine; pencillamine; aurothiomalate (intramuscular and oral); azathioprine; cochicine; beta-2 adrenoreceptor agonists (salbutamol, terbutaline, salmeteral); xanthines (theophylline, arninophylline); cromoglycate; nedocromil; ketotifen; ipratropium and oxitropium; mycophenolate mofetil; adenosine agonists; antithrombotic agents; complement inhibitors; and adrenergic agents.

The use of the GITR antagonists disclosed herein in combination with other therapeutic agents to treat or prevent specific immune disorders is discussed in further detail below.

Nonlimiting examples of agents for treating or preventing arthritic disorders (e.g., rheumatoid arthritis, inflammatory arthritis, rheumatoid arthritis, juvenile rheumatoid arthritis, osteoarthritis and psoriatic arthritis), with which a GITR antagonists can be combined include one or more of the following: IL-12 antagonists as described herein, NSAIDs; CSAIDs; TNFs, e.g., TNFa, antagonists as described herein; nondepleting anti-CD4 antibodies as described herein; IL-2 antagonists as described herein; anti-inflammatory cytokines, e.g., IL-4, IL-10, IL-13 and TGFa, or agonists thereof; IL-1 or IL-1 receptor antagonists as described herein; phosphodiesterase inhibitors as described herein; COX-2 inhibitors as described herein; iloprost (see, e.g., *Arthritis & Rheumatism* (1996) Vol. 39, No. 9 (supplement), S82); methotrexate; thalidomide (see, e.g., *Arthritis & Rheumatism* (1996) Vol. 39, No. 9 (supplement), S282) and thalidomide-related drugs (e.g., Celgen); leflunomide; inhibitor of plasminogen activation, e.g., tranexamic acid; see, e.g., *Arthritis & Rheumatism* (1996) Vol. 39, No. 9 (supplement), S284); cytokine inhibitor, e.g., T-614; see, e.g., *Arthritis & Rheumatism* (1996) Vol. 39, No. 9 (supplement), S282); prostaglandin E1 (see, e.g., *Arthritis & Rheumatism* (1996) Vol. 39, No. 9 (supplement), S282); azathioprine (see, e.g., *Arthritis & Rheumatism* (1996) Vol. 39, No. 9 (supplement), S281); an inhibitor of interleukin-1 converting enzyme (ICE); zap-70 and/or 1ck inhibitor (inhibitor of the tyrosine kinase zap-70 or 1ck); an inhibitor of vascular endothelial cell growth factor or vascular endothelial cell growth factor receptor as described herein; an inhibitor of angiogenesis as described herein; corticosteroid anti-inflammatory drugs (e.g., SB203580); TNF-convertase inhibitors; IL-11 (see, e.g., *Arthritis & Rheumatism* (1996) Vol. 39, No. 9 (supplement), S296); IL-13 (see, e.g., *Arthritis & Rheumatism* (1996) Vol. 39, No. 9 (supplement), S308); IL-17 inhibitors (see, e.g., *Arthritis & Rheumatism* (1996) Vol. 39, No. 9 (supplement), S120); gold; penicillamine; chloroquine; hydroxychloroquine; chlorambucil; cyclophosphamide; cyclosporine; total lymphoid irradiation; antithymocyte globulin; CD5-toxins; orally administered peptides and collagen; lobenzarit disodium; cytokine regulating agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see, e.g., DeLuca et al. (1995) *Rheum. Dis. Clin. North Am.* 21:759-77); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine. Preferred combinations include one or more GITR antagonists (e.g., GITRL inhibitory polynucleotides, antagonistic small molecules, and/or neutralizing antibodies to GITR and/or GITRL) in combination with methotrexate or leflunomide, and in moderate or severe rheumatoid arthritis cases, cyclosporine.

Preferred examples of inhibitors to use in combination with GITR antagonists to treat arthritic disorders include TNF antagonists (e.g., chimeric, humanized, human or in vitro-generated antibodies, or antigen binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, Enbrel™), p55 kD TNF receptor-IgG fusion protein; TNF enzyme antagonists, e.g., TNFa converting enzyme (TACE) inhibitors); antagonists of IL-12, IL-15, IL-17, IL-18, IL-22; T cell and B cell-depleting agents (e.g., anti-CD4 or anti-CD22 antibodies); small molecule inhibitors, e.g., methotrexate and leflunomide; sirolimus (rapamycin) and analogs thereof, e.g., CCI-779; cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Most preferred additional therapeutic agents that can be coadministered and/or coformulated with one or more GITR antagonists (e.g., GITRL inhibitory polynucleotides, antagonistic small molecules, and/or neutralizing antibodies to GITR and/or GITRL) include one or more of: a soluble fragment of a TNF receptor, e.g., p55 or p75 human TNF receptor or derivatives thereof, e.g., 75 kdTNFR-IgG (75 kD TNF receptor-IgG fusion protein, Enbrel™); methotrexate, leflunomide, or a sirolimus (rapamycin) or an analog thereof, e.g., CCI-779.

Nonlimiting examples of agents for treating or preventing multiple sclerosis with which a GITR antagonist can be combined include the following: interferons, e.g., interferon-alphala (e.g., Avonex™; Biogen) and interferon-1b (Betaseron™; Chiron/Berlex); Copolymer 1 (Cop-1; Copaxone™; Teva Pharmaceutical Industries, Inc.); hyperbaric oxygen; intravenous immunoglobulin; cladribine; TNF antagonists as described herein; corticosteroids; prednisolone; methylprednisolone; azathioprine; cyclophosphamide; cyclosporine; methotrexate; 4-aminopyridine; and tizanidine. Additional agents that can be used in combination with GITR antagonists (e.g., GITRL inhibitory polynucleotides, antagonistic small molecules, and/or neutralizing antibodies to GITR and/or GITRL) include antibodies to or antagonists of human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. GITR antagonists (e.g., GITRL inhibitory polynucleotides, antagonistic small molecules, and/or neutralizing antibodies to GITR and/or GITRL) as described herein can be combined with antibodies to other cell surface molecules such as CD2, CD3, CD4, CD8, CD25, CD28, CD30, CD40, CD45, CD69, CD80, CD86, CD90 or their ligands. The GITR antagonists (e.g., GITRL inhibitory polynucleotides, antagonistic small molecules, and/or neutralizing antibodies to GITR and/or GITRL) may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines as described herein, IL-Ib converting enzyme inhibitors (e.g., Vx740), anti-P7s, PSGL, TACE inhibitors, T cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, and anti-inflammatory cytokines (e.g. IL-4, IL-10, IL-13 and TGF).

Preferred examples of therapeutic agents for multiple sclerosis with which the GITR antagonists (e.g., GITRL inhibitory polynucleotides, antagonistic small molecules, and/or neutralizing antibodies to GITR and/or GITRL) can be combined include interferon-b, for example, IFNb-1a and IFNb-1b; copaxone, corticosteroids, IL-1 inhibitors, TNF inhibitors, antibodies to CD40 ligand and CD80, and IL-12 antagonists.

Nonlimiting examples of agents for treating or preventing inflammatory bowel disease (e.g., Crohn's disease, ulcerative colitis) with which a GITR antagonist (e.g., GITRL inhibitory polynucleotides, an antagonistic small molecule, a neutralizing anti-GITR antibody, and/or neutralizing anti-GITRL antibody) can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13 and/or TGFb cytokines or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of platelet activating factor (PAF); ciprofloxacin; and lignocaine.

In one embodiment, a GITR antagonist (e.g., GITRL inhibitory polynucleotides, an antagonistic small molecule, a neutralizing anti-GITR antibody, and/or neutralizing anti-GITRL antibody) can be used in combination with one or more antibodies directed at other targets involved in regulating immune responses, e.g., transplant rejection or graft-v-host disease. Nonlimiting examples of agents for treating or preventing immune responses with which a GITR antagonist (e.g., GITRL inhibitory polynucleotides, an antagonistic small molecule, a neutralizing anti-GITR antibody, and/or neutralizing anti-GITRL antibody) of the invention can be combined include the following: antibodies against other cell surface molecules, including but not limited to CD25 (interleukin-2 receptor-a), CD11a (LFA-1), CD54 (ICAM-1), CD4, CD45, CD28/CTLA4, CD80 (B7.1) and/or CD86 (B7.2). In yet another embodiment, a GITR antagonist (e.g., GITRL inhibitory polynucleotides, an antagonistic small molecule, a neutralizing anti-GITR antibody, and/or neutralizing anti-GITRL antibody) is used in combination with one or more general immunosuppressive agents, such as cyclosporin A or FK506.

In other embodiments, GITR antagonists (e.g., GITRL inhibitory polynucleotides, an antagonistic small molecule and/or neutralizing anti-GITRL antibody) are used as vaccine adjuvants against autoimmune disorders, inflammatory diseases or transplant rejection. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

For example, desirable vaccines for moderating responses to allergens in a vertebrate host, which contain the adjuvant combinations of this invention, include those containing an allergen or fragment thereof. Examples of such allergens are described in U.S. Pat. No. 5,830,877 and published International Patent Application No. WO 99/51259, which are hereby incorporated by reference in their entireties, and include pollen, insect venoms, animal dander, fungal spores and drugs (such as penicillin). The vaccines interfere with the production of IgE antibodies, a known cause of allergic reactions. In another example, desirable vaccines for preventing or treating disease characterized by amyloid deposition in a vertebrate host, which contain the adjuvant combinations of this invention, include those containing portions of amyloid peptide protein (APP). This disease is referred to variously as Alzheimer's disease, amyloidosis or amyloidogenic disease. Thus, the vaccines of this invention include the adjuvant combinations of this invention plus Aβ peptide, as well as fragments of Aβ peptide and antibodies to Aβ peptide or fragments thereof.

Methods of 1) downregulating antigen presenting cell function; and 2) combination therapy for managing immunosuppression are well known in the art (see, e.g., Xiao et al. (2003) Dendritic cell vaccine design: strategies for eliciting peripheral tolerance therapy of autoimmune diseases. *BioDrugs* 17:103-11; Kuwana (2002) Induction of anergic and regulatory T cells by plasmacytoid dendritic cells and other dendritic cell subsets. *Hum. Immunol.* 63:1156-63; Lu et al. (2002) Manipulation of dendritic cells for tolerance induction in transplantation and autoimmune disease. *Transplantation* 73:S19-S22; Rifle et al. (2002) Dendritic cells and second signal blockade: a step toward allograft tolerance. *Transplantation* 73:S1-S2; Mancini et al. (2004) The management of immunosuppression: the art and the science. *Crit. Care. Nurs. Q.* 27:61-64).

Another aspect of the present invention accordingly relates to kits for carrying out the combined administration of GITR antagonists (e.g., GITRL inhibitory polynucleotides, antagonistic small molecules, and/or neutralizing antibodies to GITR and/or GITRL) with other therapeutic compounds. In one embodiment, the kit comprises one or more binding agents formulated in a pharmaceutical carrier, and at least one agent, e.g., therapeutic agent, formulated as appropriate, in one or more separate pharmaceutical preparations.

The present invention is illustrated by the following Examples related to a novel mouse cDNA, designated mouse GITRL cDNA, encoding a novel ligand polypeptide designated mouse GITRL, as well as novel antibodies to GITRL. One of skill in the art would understand the teachings of the Examples to be applicable to all homologs of mouse GITRL.

EXAMPLES

The Examples which follow are set forth to aid in the understanding of the invention but are not intended to, and should not be construed to, limit its scope in any way. The Examples do not include detailed descriptions of conventional methods, such as flow cytometry (e.g., FACS), PCR, Northern and in situ hybridization, or those methods employed in the construction of vectors, the insertion of genes encoding the polypeptides into such vectors and plasmids, the introduction of such vectors and plasmids into host cells, and the expression of polypeptides from such vectors and plasmids in host cells. Such methods are well known to those of ordinary skill in the art.

Example 1

Identification of GITRL DNA Sequences

Example 1.1

Identification of the Mouse GITRL cDNA and Genomic Sequences

Two approaches were taken to identify the murine GITRL homolog. In one approach, the amino acid sequence of human GITRL (from GenBank Acc. No. AX077015) was used in a Tblastn search against div1; div2; div3; div4; gbdiv_cu; Celera mouse (cm); and draft_mouse-dna databases. Genomic sequence ga_69772862.cm_4 was identified as one of the possible hits to investigate. Missing amino acid sequences were identified in a Thlastn search with the amino acid sequence of human GITRL (GenBank Acc. No. AX077015) against the unmasked Celera mouse genomic assembly (cm) using expectation value (E) =10 (default), 100 and 1000. Genomic sequence ga_x5j8b7w7wj5_041.cm_aa_2 was identified as the genomic sequence containing the missing amino acid sequences.

In another approach, the amino acid sequence of human GITRL (from GenBank Acc. No. NM_005092) was used in a Tblastn search against the unmasked Celera mouse genomic assembly (cm) using default expectation value (E)=10 and 1000. Genomic sequence ga_x5j8b7w7wj5_041.cm_aa_2 was identified as the genomic sequence containing three high scoring pair (HSP) regions.

A putative mouse cDNA sequence was constructed based on the three HSP regions obtained in the above-described Thlastn search. This cDNA sequence was edited based on the comparison between the alignments of the three human exon sequences with the corresponding human genomic sequence from Celera (ga_x2htbl3vud5_66.ch_r25h_1) and the three derived mouse putative exon sequences with the corresponding mouse genomic sequence from Celera (ga_x5j8b7w7wj5_041.cm_aa_2). This editing took into account the splice junctions for the human sequence. The edited mouse GITRL cDNA sequence contained an open reading frame of 519 bp (coding sequence of 522 bp), corresponding to a protein of 173 amino acids.

Primers were designed based on the putative exons of mouse GITRL genomic sequence and used to isolate the corresponding physical cDNA clone from a murine thymus cDNA library by PCR. The sequences of the forward (SEQ ID NO:4) and reverse (SEQ ID NO:5) PCR primers were:

```
5' ATGGAGGAAATGCCTTTGAGAG 3',      (forward primer)
and

5' GAATGGTAGATCAGGCATTAAGATG 3'.   (reverse primer)
```

The resulting fragment was subcloned and the DNA sequence was determined using standard methods. The resulting fragment confirmed the existence of a mouse GITRL cDNA comprising all three predicted exons (see below). This fragment was extended to include the final coding segment (two amino acids) of the cDNA by PCR amplification of this resulting cDNA clone. The sequences of the forward (SEQ ID NO:6) and reverse (SEQ ID NO:7) PCR primers for this step were:

```
5' TTTAAAGTCGACCCACCATGGAGGAAATGCCTTTGAGAG 3',
(forward primer)
and

5' TTTAAAGAATTCTCATTAAGAGATGAATGGTAGATCAGGCAT 3'.
(reverse primer)
```

The forward PCR primer contained a SalI site, a Kozak sequence for translation initiation, and the ATG encoding the initiating methionine. The reverse primer contained an EcoRI site. The SalI and EcoRI sites were used for directional subcloning, and sequence determination of the final cDNA clone was performed.

The full-length mouse GITRL cDNA sequence and its deduced amino acid sequence are set forth in SEQ ID NO:1 and SEQ ID NO:2, respectively. Alignment of the human GITRL cDNA (SEQ ID NO:8) and mouse GITRL cDNA sequences revealed 69.6% identity. Alignment of the human GITRL amino acid (SEQ ID NO:9) and mouse GITRL amino acid sequences (FIG. 1) revealed 54.1% identity and 60.0% similarity. This degree of amino acid identity is similar to that which exists in general between human and mouse homologs of other TNFR ligands (Oshima et al. (1998) *Int. Immunol.* 10:517-26).

Comparison of the cloned mouse GITRL cDNA sequence (SEQ ID NO:1) with publicly available murine databases revealed a single nucleotide polymorphism (SNP) in the coding region of mouse GITRL (an A/C transversion at nucleotide position 470 of SEQ ID NO:1 in exon 3, which results in an asparagine to threonine change at amino acid position 157 of SEQ ID NO:2).

Comparison of the mouse GITRL cDNA sequence with the mouse genomic sequence from Celera (ga_x5j8b7w7wj5_041.cm aa_2) described above revealed that the mouse GITRL locus contains three exons and two introns (see Table 2 below), with exonic size and position well conserved between mouse and human GITRL. The mouse GITRL genomic DNA sequence is set forth in SEQ ID NO:3.

TABLE 2

| Region in SEQ ID NO: 3 | Sequence Attribute | Length (bp) | Position in SEQ ID NO: 1 |
|---|---|---|---|
| 1-255 | 5'-sequence | 255 | — |
| 256-390 | Exon#1 | 135 | 1-135 |
| 391-6010 | Intron#1 | 5620 | — |
| 6011-6044 | Exon#2 | 34 | 136-169 |
| 6045-8990 | Intron#2 | 2946 | — |
| 8991-9340 | Exon#3 | 350 | 170-519 |
| 9341-9343 | Stop | 3 | 520-522 |
| 9344-10289 | 3'-Sequence | 946 | — |

A comparison of the genomic structure of mouse GTRL (Table 2) with the genomic structure of human GITRL (see Table 3 below) shows that exonic size and intronic position are well conserved between the human and mouse GITRL genomic DNA sequences. The human GITRL genomic DNA sequence is set forth in SEQ ID NO:10.

TABLE 3

| Region in SEQ ID NO: 10 | Sequence Attribute | Length (bp) | Position in SEQ ID NO: 8 |
|---|---|---|---|
| 1-421 | 5'-sequence | 421 | — |
| 422-577 | Exon#1 | 156 | 1-156 |
| 578-7348 | Intron#1 | 6771 | — |
| 7349-7379 | Exon#2 | 31 | 157-187 |
| 7380-9604 | Intron#2 | 2225 | — |
| 9605-9948 | Exon#3 | 344 | 188-531 |
| 9949-9951 | Stop | 3 | 532-534 |
| 9952-10331 | 3'-Sequence | 380 | — |

Example 1.2

Hydrophobicity Profile of Mouse GITRL

The hydrophobicity profile of mouse GITRL was determined by TopPred (Claros and von Heijne (1994) *Comput. Appl. Biosci.* 10:685-6). A plot of the hydrophobicity score against the amino acid residues of mouse GITRL (SEQ ID NO:2) revealed a single putative hydrophobic region located approximately between amino acids 25-50, similar to human GITRL. This hydrophobic segment corresponds to the predicted transmembrane region for type II transmembrane proteins.

Example 2

Tissue Expression of Mouse GITRL

Oligonucleotide probes based on the mouse GITRL cDNA sequence (SEQ ID NO:1) were used to test several murine tissue samples for GITRL expression by Northern hybridization, in situ hybridization, and real-time PCR (e.g., Heid et al. (1996) *Genome Res.* 6:986-94; Mullah et al. (1998) *Nucleic Acids Res.* 26:1026-31; Giulietti et al. (2001) *Methods* 25:386-401).

Although Northern hybridization revealed barely detectable transcripts in heart, spleen, lung, lymph node, kidney, and liver, subsequent in situ hybridization revealed GITRL expression in the heart, spleen, lymph node and thymus. GITRL expression in these tissues was generally limited to the pericardial and endocardial cells of the heart, the white pulp of the spleen, the cortical, paracortical and medullary zones of lymph nodes, and the cortical and medullary zones of the thymus.

GITRL expression in thymus, spleen and lymph node was further confirmed by real-time PCR analysis. GITRL was expressed at the highest levels in spleen and lipopolysaccharide (LPS)-stimulated spleen cells, which are primarily B lymphocytes. Vanishingly low levels of GITRL expression were detected in stomach, brain, and kidney. Real-time PCR analysis also revealed GITRL transcripts in liver, activated $CD25^-$ cells, activated $CD25^+$ cells, and concanavalin A-activated lymph node cells, although to a lesser degree than the spleen and LPS blasts. No GITRL expression was detected in resting $CD25^-$ or $CD25^+$ cells. Real-time PCR analysis of immature and LPS-stimulated bone marrow-derived dendritic cells (DC) also demonstrated baseline GITRL expression by immature DC that increased upon stimulation with LPS for 24 hours, but decreased below baseline after 48 hours of LPS stimulation. GITRL expression was also detected to varying degrees in all endothelial cell lines tested (bEND3, C166, EOMA, MSI and SVEC4-10), and was demonstrated to remain relatively unchanged when the cell lines were stimulated with LPS. In contrast, GITRL cDNA was not detected by PCR in the following unstimulated murine cell lines of specified origin: E10 T cell line, T2 fetal thymus line, T10 plasmacytoma, EL4 thymoma, BAF3 and PREB pre-B cell lines, B9 B cell hybridoma, DAIG monocytic, M1 monocytic, FBMD-1 fetal bone marrow, P19 embryonic carcinoma, MDF liver, and E14 embryonic stem cell line.

Example 3

Functional Expression of Recombinant Mouse GITRL

Example 3.1

Binding of GITRL to Cell-Surface GITR

To determine whether the mouse cDNA isolated in Example 1 encoded a functional GITR ligand (GITRL), Cos cells expressing mouse GITRL fused to the FLAG epitope (GITRL-Flag-Cos) or control mouse IL-21 receptor fused to the FLAG epitope (IL-21R-Flag-Cos) were incubated for various lengths of time with 293T cells expressing mouse GITR (GITR-293T). Cell-cell interaction was detected by flow cytometry using phycoerythrin-labeled anti-Flag antibody (PE-FLAG) and fluorescein isothiocyanate (FITC)-labeled anti-GITR. Even 1 min post cocentrifugation of the GITR-293T and GITRL-Flag-Cos cells, ~90% of GITR-293T cells (as detected by FITC fluorescence) costained for FLAG (as detected by PE fluorescence), indicating that the GITR-293T cells were bound to the GITRL-Flag-Cos cells, and this interaction persisted throughout the entire 60 min of the experiment. In contrast, GITR-293T cells incubated with IL-21 R-Flag-Cos cells did not significantly costain for FLAG, even at 60 min post cocentrifugation. These data demonstrate that the mouse cDNA isolated in Example 1 encodes for a functional GITRL capable of binding cell-surface GITR.

Example 3.2

Binding of GITRL to Soluble GITR

The ability of mouse GITRL to bind GITR was confirmed by incubating Cos cells expressing mouse GITRL (GITRL-Cos) or mock-transfected Cos cells with recombinant GITR fused to the Fc portion of human IgG (GITR-Fc) or control human IgG (HIgG). Binding of GITR-Fc to GITRL was determined by flow cytometry using donkey antihuman antibody conjugated to FITC (FITC-Ab). Incubation of GITRL-Cos cells with GITR-Fc resulted in a 3.6-fold increase in FITC-Ab binding (28.8%) compared to incubation of GITRL-Cos cells with control HIgG (7.9%). Unstained GITRL-Cos cells, GITRL-Cos cells incubated with CTLA-4:Fc fusion protein and FITC-Ab, and GITRL-Cos cells incubated with FITC-Ab alone exhibited no fluorescence. Neither treated nor untreated mock-transfected Cos cells exhibited any appreciable fluorescence. These data demonstrate that the mouse cDNA isolated in Example 1 encodes for a functional GITRL capable of binding soluble GITR.

Example 4

Binding of Mouse GITRL to GITR Results in Proliferation of $CD4^+CD25^+$ Cells

The effect of GITRL:GITR binding on cellular proliferation was determined by stimulating ~50,000 murine T cells with ~50,000 irradiated T cell-depleted splenocytes, and 100 IU/ml IL-2 for 65-72 hrs in the absence or presence of varying concentrations of a GITR-binding protein. Two GITR-binding proteins were used in these assays: either an agonistic anti-GITR antibody (see, e.g., McHugh et al. (2002) *Immunity* 16:311-23; see also U.S. patent application Ser. No. 10/194,754) or murine GITRL expressed on the surface of modified rat YB2/0 cells (GITRL-YB2/0). Cellular proliferation was assayed by pulsing cells with 1 µCi $^3$H-thymidine for the last 6-12 hr of culture and then measuring $^3$H-thymidine incorporation via scintillation counting.

As shown in FIG. 2A, $CD4^+CD25^-$ T cells did not respond to any concentration of anti-GITR antibody. In contrast, anti-GITR antibody stimulated the proliferation of $CD4^+CD25^+$ T cells at all concentrations tested. For example, culture of $CD4^+CD25^+$ T cells in the presence of the lowest titre of anti-GITR antibody tested (~0.02 µg/ml) resulted in a ~3-fold increase in $^3$H-thymidine incorporation (~15,000 cpm) over cells cultured in the absence of anti-GITR antibody. The ability of anti-GITR antibody to stimulate $CD4^+CD25^+$ T cell proliferation reached a plateau of ~45,000 cpm at an antibody concentration of ~0.3 µg/ml, corresponding to a ~9-fold increase in $^3$H-thymidine incorporation over cells cultured in the absence of anti-GITR antibody.

Similar to the results obtained with the anti-GITR antibody, GITRL-YB2/0 cells did not stimulate proliferation of $CD4^+CD25^-$ T cells (FIG. 2B). In contrast, GITRL-YB2/0 cells markedly stimulated the proliferation of $CD4^+CD25^+$ T cells. For example, culture of $CD4^+CD25^+$ T cells in the presence of ~10,000 GITRL-YB2/0 cells resulted in a ~4-5-fold increase in $^3$H-thymidine incorporation over cells cultured in the presence of an equal number of unmodified YB2/0 cells. Increasing the number of YB2/0 cells to ~50,000 resulted in a ~15-fold increase in $^3$H-thymidine incorporation over cells cultured in the presence of an equal number of unmodified YB2/0 cells (FIG. 2B).

Example 5

Binding of Mouse GITRL to GITR Reverses $CD4^+CD25^+$ T Cell-Mediated Suppression of $CD4^+CD25^-$ T Cells The T cell suppressor assay used in these Examples has been previously described (see, e.g., Thornton and Shevach (2000) *J. Immunol.* 164:183-90; McHugh et al. (2002) *Immunity* 16:311-23; both hereby incorporated by reference). Briefly, ~50,000 $CD4^+CD25^-$ responder T cells were cultured in the presence of ~50,000 irradiated T cell-depleted splenocytes, 0.5 µg/ml anti-CD3 antibody, and various numbers of freshly isolated suppressor $CD4^+CD25^+$ T cells. The ability of ~50,000 irradiated GITRL-YB2/0 cells or 2 µg/ml agonistic anti-GITR antibody to reverse suppression of $CD4^+CD25^-$ proliferation was then assessed by measuring $^3$H-thymidine incorporation via scintillation counting.

Figure 3:
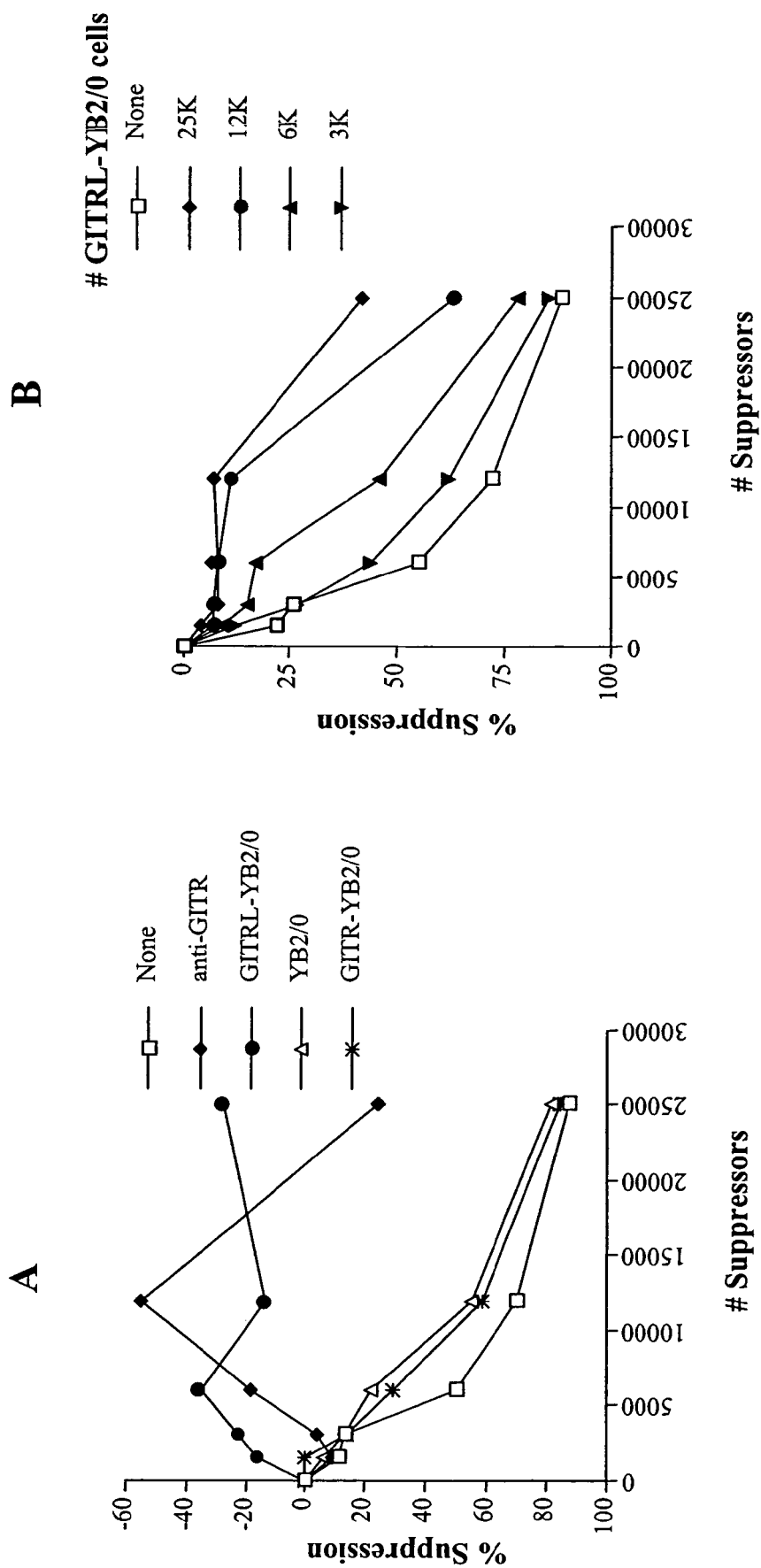
FIG. 3A shows that GITRL expressed by YB2/0 cells (~50,000), as well as agonistic anti-GITR antibody (2 µg/ml), reversed the suppression (i.e., negative percent suppression) produced by freshly isolated $CD4^+CD25^+$ suppressor T cells (# suppressors).
FIG. 3B shows that GITRL-YB2/0 cells in numbers less than 50,000 (i.e., ~3,000-25,000) were able to partially reverse suppression in a dose-dependent manner.

As shown in FIG. 3A, $CD4^+CD25^+$ cells reduced proliferation of $CD4^+CD25^-$ cells in a dose-dependent manner. Both anti-GITR antibody and GITRL-YB2/0 cells were able to completely reverse the suppression of $CD4^+CD25^-$ proliferation over the entire range of number of $CD4^+CD25^+$ suppressor cells tested. Thus binding of GITRL to its receptor GITR, like binding of agonistic anti-GITR antibody to GITR, blocked the suppressive function of $CD4^+CD25^+$ cells. The ability of GITRL-YB2/0 cells to reverse suppression occurred in a dose-dependent manner, with as few as ~3,000 GITRL-YB2/0 cells at least partially reversing or decreasing suppression in this assay (FIG. 3B). Neither unmodified YB2/0 nor YB2/0 cells expressing GITR had an appreciable effect on $CD4^+CD25^+$ T cell-mediated suppression (FIG. 3A).

Figure 4:
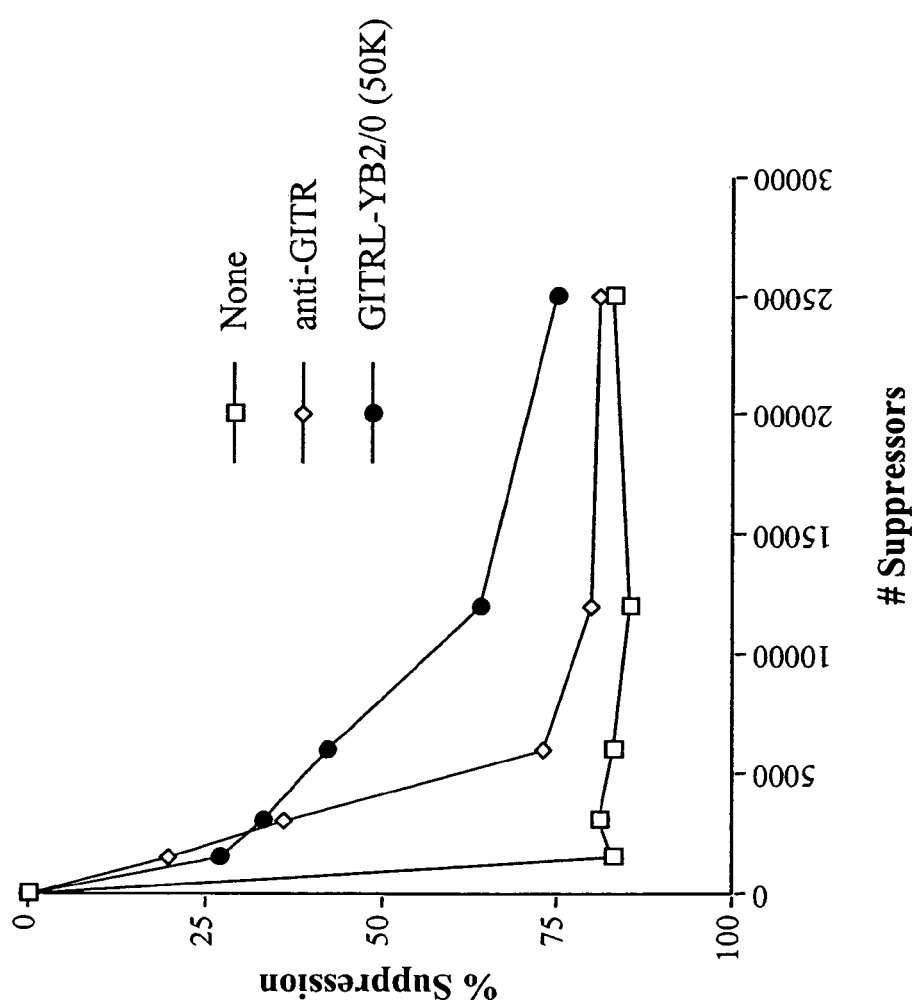
FIG. 4 shows that GITRL-YB2/0 cells (~50,000) did not reverse suppression when activated $CD4^+CD25^+$ T cells were used in place of freshly isolated $CD4^+CD25^+$ T cells; similar results were obtained with agonistic anti-GITR antibody.

In contrast to the results obtained with freshly isolated $CD4^+CD25^+$ T cells, GITRL:GITR binding had little-to-no effect on suppression mediated by $CD4^+CD25^+$ T cells activated with anti-CD3 antibody, T cell-depleted splenocytes, and IL-2 (FIG. 4). Neither the addition of anti-GITR antibody nor ~50,000 GITRL-YB2/0 cells was able to reverse suppression mediated by ~25,000 activated $CD4^+CD25^+$ T cells. When fewer activated $CD4^+CD25^+$ T cells were added to the assay (e.g., ~1,500-12,500 cells), however, anti-GITR antibody and GITRL-YB2/0 cells were able to partially decrease, but not completely abrogate, suppression.

Example 6

Anti-Mouse GITRL Antibody Restores Suppression Mediated by $CD4^+CD25^+$ T Cells Example 6.1

Isolation of Anti-Mouse GITRL Antibodies

Antibodies specific for mouse GITRL were produced by immunizing rats with rat YB2/0 cells expressing the mouse GITRL cDNA (GITRL-YB2/0). Using methods well known in the art, antibody hybridomas were created and screened against Phoenix cells expressing mouse GITRL using flow cytometry. Two antibodies, 5F1 and 10F12, were identified that bound specifically to GITRL-Phoenix cells and not mock-transfected Phoenix control cells. These antibody hybridomas were deposited with the American Type Culture Collection (ATCC) on Jul. 22, 2003; ATCC assigned number PTA-5336 to hybridoma 5F1, and number PTA-5337 to hybridoma 10F12.

Example 6.2

Anti-Mouse GITRL Antibodies Block the Effects of GITRL on Suppressor Activity of $CD4^+CD25^+$ T Cells As described in Example 5 above, YB2/0 cells expressing GITRL on their cell surface were able to reverse the suppression of $CD4^+CD25^-$ T cell proliferation mediated by freshly isolated $CD4^+CD25^+$ T cells. To determine whether anti-GITRL antibodies could restore $CD4^+CD25^+$ T cell-mediated suppression, the T cell suppressor assay as described in Example 5 was performed in the presence or absence of either 5F1 or 10F12 anti-GITRL antibody or control antibodies.

Figure 5:
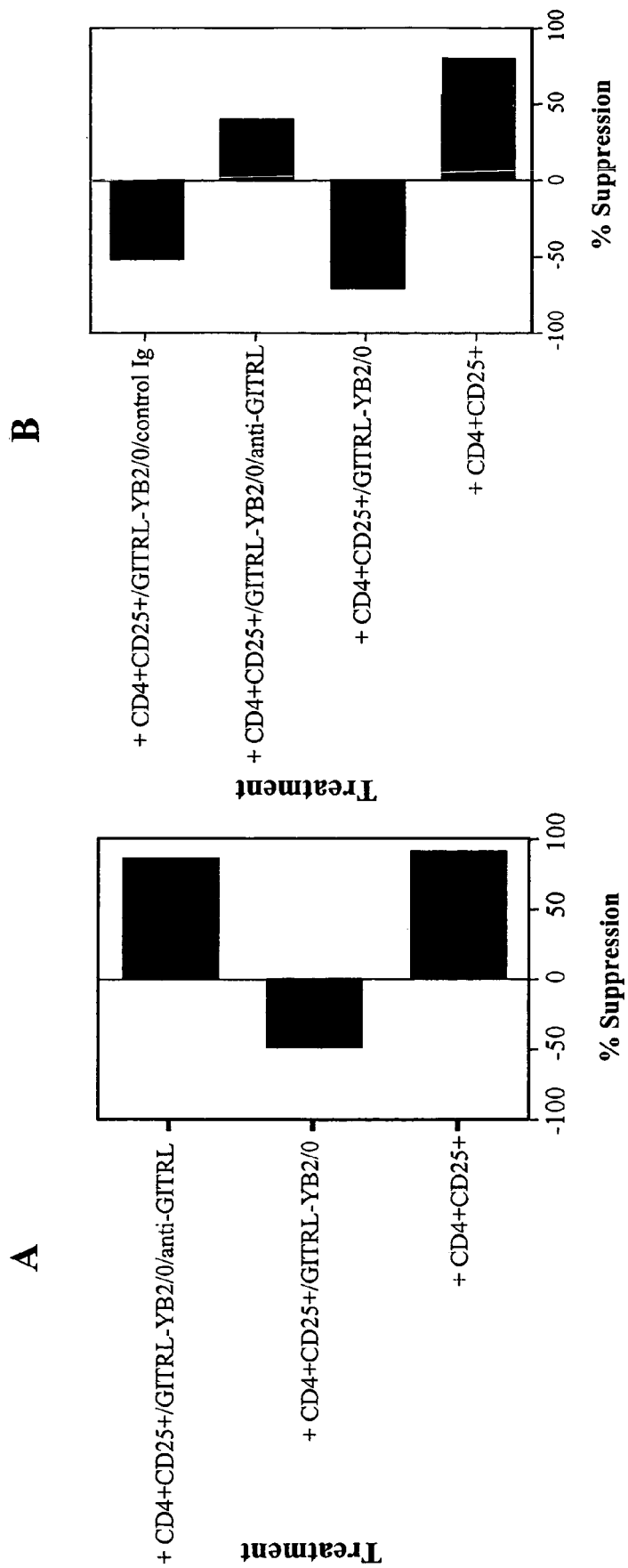
FIGS. 5A and 5B show that the GITRL-induced reversal of the suppression produced by freshly isolated $CD4^+CD25^+$ T cells can itself be reversed (i.e., restoration of suppression) in the presence of anti-GITRL antibody ("anti-GITRL"=5F1 antibody).

As seen in Example 5, culture of $CD4^+CD25^-$ responder T cells and freshly isolated $CD4^+CD25^+$ suppressor T cells in the presence of GITRL-YB2/0 cells resulted in complete reversal of suppression of $CD4^+CD25^-$ cell proliferation (FIG. 5A and 5B). The addition of 10% hybridoma culture supernatants containing 5F1 anti-GITRL antibody to the assay resulted in partial (FIG. 5B) to almost complete (FIG. 5A) restoration of $CD4^+CD25^+$-mediated suppression. Addition of 10F12 anti-GITRL antibody gave similar results. As expected, the presence of control antibodies ("control Ig") had no appreciable effect on the ability of GITRL-YB2/0 cells to reverse suppression (FIG. 5B). These data demonstrate that anti-GITRL antibodies block the ability of GITRL to turn off the suppressor activity of $CD4^+CD25^+$ cells.

Example 6.3

Anti-Mouse GITRL Antibodies Suppress T Cell Responses only in the Presence of $CD4^+CD25^+$ T Cells Lymph node cell cultures were stimulated in the presence of varying concentrations of agonistic anti-CD3 antibody prior to (FIG. 6A) or after the depletion of (FIG. 6B) $CD4^+CD25^+$ T cells, and proliferation was measured by determining $^3$H-thymidine incorporation via scintillation counting. To determine the effects of anti-GITRL antibody on proliferation, 10% hybridoma culture supernatants containing 5F1 anti-GITRL antibody were added to parallel cultures.

Figure 6:
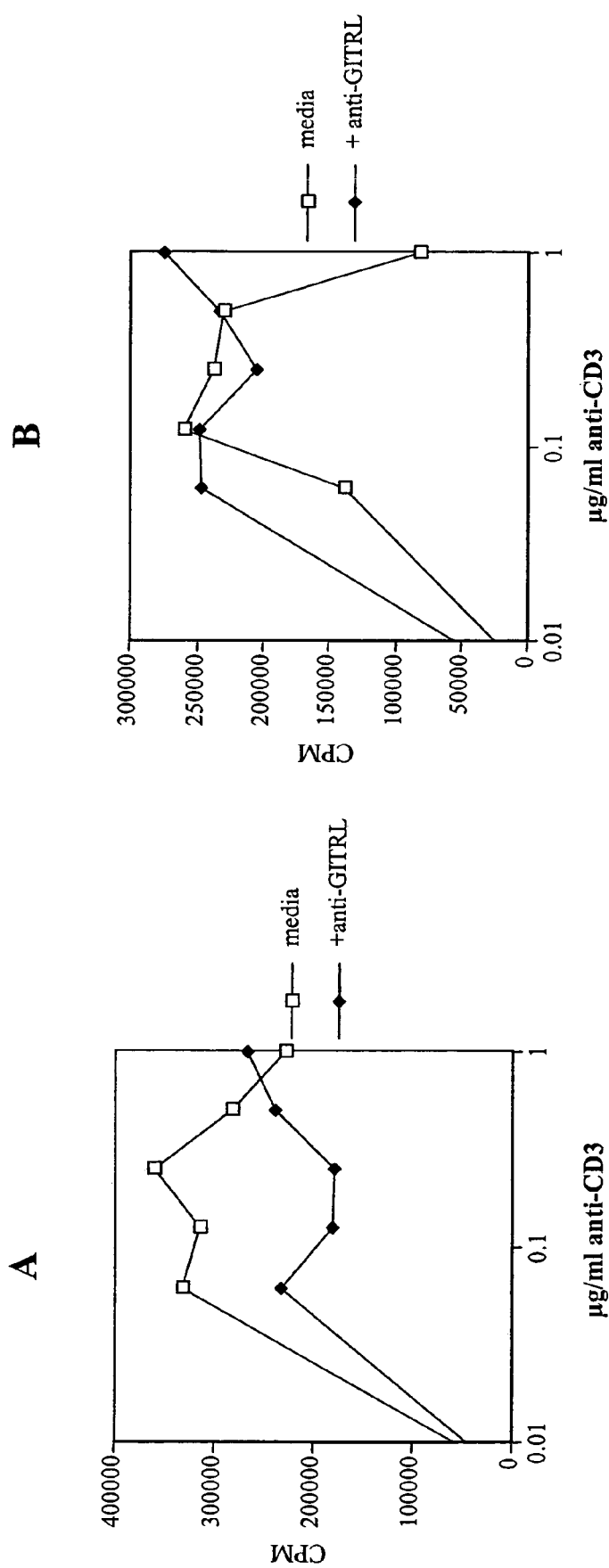
FIG. 6 shows that anti-GITRL antibody can only enhance suppression in the presence of $CD4^+CD25^+$ T cells.

As shown in FIG. 6A, addition of anti-GITRL antibody suppressed proliferation of lymph node cells containing $CD4^+CD25^+$ T cells when the cells were stimulated with ~0.075 µg/ml to 0.75 µg/ml anti-CD3 antibody. Suppression was not seen in the presence of the anti-GITRL antibody when the lymph node cells containing $CD4^+CD25^+$ T cells were stimulated with 1.0 µg/ml anti-CD3 antibody. In contrast to the results obtained with lymph node cell cultures containing $CD4^+CD25^+$ T cells, the addition of anti-GITRL antibody generally had no suppressive effects on lymph node cell cultures that had been depleted of $CD4^+CD25^+$ T cells (FIG. 6B). Taken together, these data suggest that anti-GITRL antibody blocks the interaction between GITR expressed on $CD4^+CD25^+$ T cells and GITRL expressed on other cells, and that blockade of this GITR/GITRL interaction enhances the regulatory function of $CD4^+CD25^+$ T cells to restore immunosuppression.

Example 7

Distribution of GITRL-expressing Cells in Lymphoid Tissues

Figure 7:
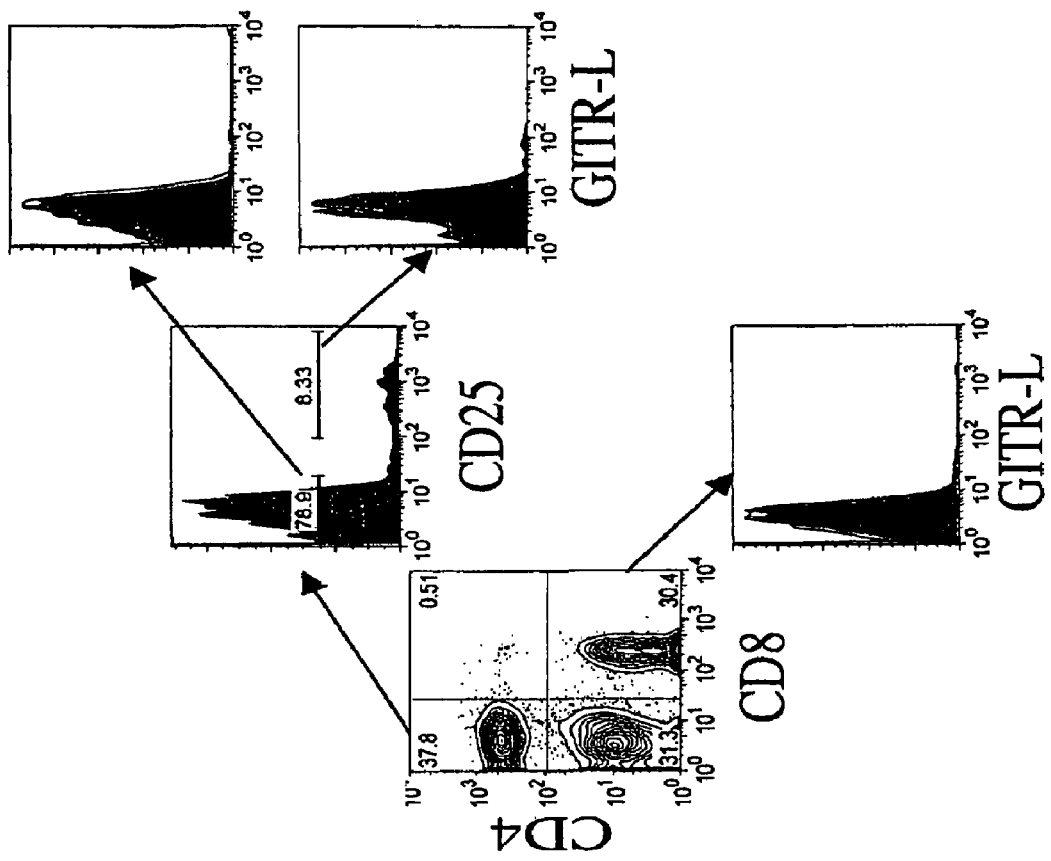
FIG. 7 shows the distribution of GITRL expressing cells in lymphoid tissues.

The agonistic anti-GITRL antibody was used to examine the expression of GITRL in mouse tissues by flow cytometry. Freshly isolated $CD11c^+$ splenic dendritic cell (DC) subsets expressing CD4 only, CD8 only, or both CD4 and CD8, constitutively expressed low levels of GITRL (FIG. 7A). However, surface expression of GITRL was noticeably higher among $CD11c^{low}B220^+$ plasmacytoid dendritic cells (Nakano et al., 2001). In FIG. 7B, staining with anti-GITRL mAb or an isotype control was done on the indicated subsets of freshly isolated $CD11c^+$ splenic DCs from BALB/c mice.

Similarly, freshly isolated $B220^+$ splenic B cells constitutively expressed GITRL, as did peritoneal B-1 B cells (perC $CD11B^+B220^+$), although at higher levels (FIG. 7C, top). Resting peritoneal macrophages (perC $CD11B^+B220^-$) were also found to express this ligand (FIG. 7C, bottom).

Thymocyte subsets undergoing selection did not express measurable amounts of GITRL (FIG. 7D). In contrast, as shown in FIG. 7E, expression of GITRL was detectable on all subsets of $CD4^-CD8^-$ thymic precursors, with $CD44^+CD25^+$ (R2) and $CD44^-CD25^+$ (R3) subsets expressing the highest levels.

GITRL was undetectable on unstimulated lymph node cells (FIG. 7F). GITRL was also undetectable on unstimulated splenic T cells (data not shown). These data demonstrate the expression of GITRL by professional antigen presenting cells (DCs, B cells and macrophages; FIG. 7A-7C) and thymic $CD4^- CD8^-$ precursor cells (FIG. 7E), but not T cells undergoing selection (FIG. 7D) or resting T cells in the periphery (unstimulated lymph node and splenic cells; FIG. 7F, and data not shown). These data correlated with data obtained by Northern hybridization, in situ hybridization, and real-time PCR as described in Example 2 (above).

Example 8

APCs Downregulate GITRL Following TLR Stimulation

Figure 8:
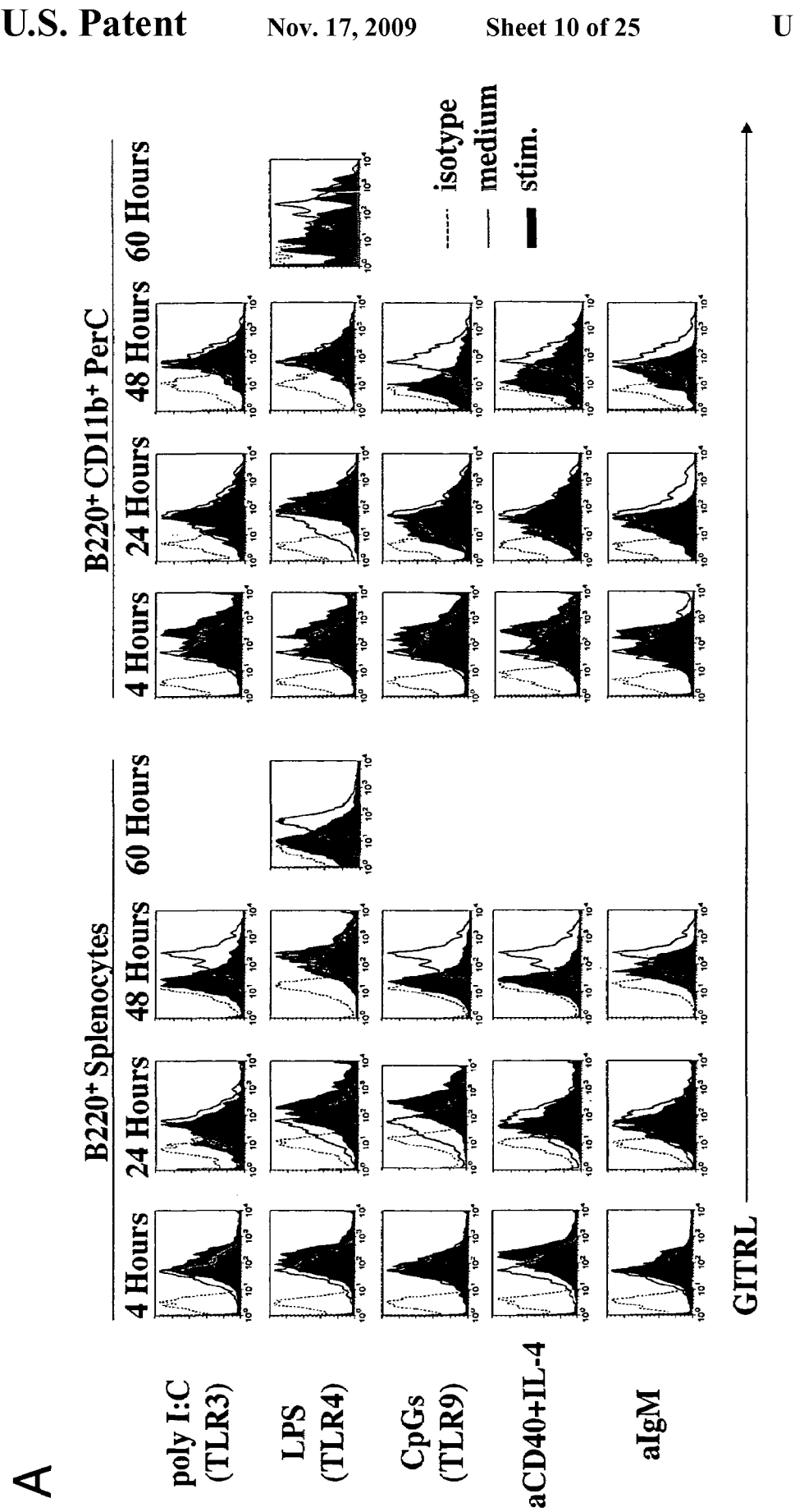
FIG. 8 shows the downregulation by APCs of GITRL following stimulation.

The effects of B cell activation on GITRL expression were examined following treatment with Toll-like receptor (TLR) ligands, or anti-CD40 and IL-4, or anti-IgM. Stimulation of either splenic B cells ($B220^+$ splenocytes) or peritoneal B-1 B cells ($B220^+CD11b^+$ PerC) resulted in a rapid but transient upregulation of GITRL, which was apparent after 4 hours with most of the treatments (FIG. 8A). Following 48-60 hours of stimulation, expression declined to below prestimulation levels where it stabilized. An exception was polyI:C-treated B-1 B cells from the peritoneal cavity, which did not display this downregulation during the time points examined. As expected, levels of CD86 increased over the course of the experiment in all groups, indicating that the observed downregulation of GITRL was not secondary to cell death (data not shown).

The reduction of GITRL expressed by B cells after treatment with anti-CD40 and IL-4 suggested that expression could be modulated following the provision of T cell help. GITRL expression by B cells among total splenocytes was assessed after culture with anti-CD3 antibody. Under these culture conditions, expression of GITRL on $B220^+$ splenocytes was also downregulated after 48 hours (FIG. 8B). Thus, physiological levels of T cell activity also led to a reduction in the expression of GITRL by splenic B cells.

Splenic $CD11c^+$ DCs were enriched with magnetic beads and examined for expression of GITRL after 12 and 36 hours of culture in the presence of LPS. DCs cultured in either medium or LPS expressed GITRL during the initial 12 hours, with modest upregulation induced by LPS. However, by 36 hours, expression of GITRL was undetectable on both LPS-treated DCs as well as those cultured only in medium. FIG. 8C shows expression of GITRL (top histogram panels) and CD86 (B7.2) (bottom histogram panels) by purified $CD11c^+$ DCs following culture with or without LPS (0.5 µg/ml) at the indicated time points. As shown, CD86 (B7.2) expression was upregulated as expected (Banchereau and Steinman, 1998). The reduction in GITRL expression by splenic DCs cultured in medium suggests that the "spontaneous" DC maturation that occurs during in vitro culture (Vremec and Shortman, 1997) is sufficient to downregulate expression of GITRL. For this reason, only results following LPS stimulation are shown, although DCs were subjected to the same treatments shown for B cells. Similar to the results of another published report (Tone et al., 2003), it was found that bone marrow-derived DCs express GITRL constitutively, and that such expression was only marginally reduced after treatment with various TLR ligands (data not shown).

Both CD4 and CD8 T cells expressed measurable levels of GITRL after a 48-hour culture of splenocytes in the absence ("+Med.") or presence ("+aCD3") of soluble anti-CD3 antibody (FIG. 8D), confirming previous real time PCR (see also Example 2).

Example 9

Blockade of GITR/GITRL Interaction Inhibits Lymphocyte Proliferation

Figure 9:
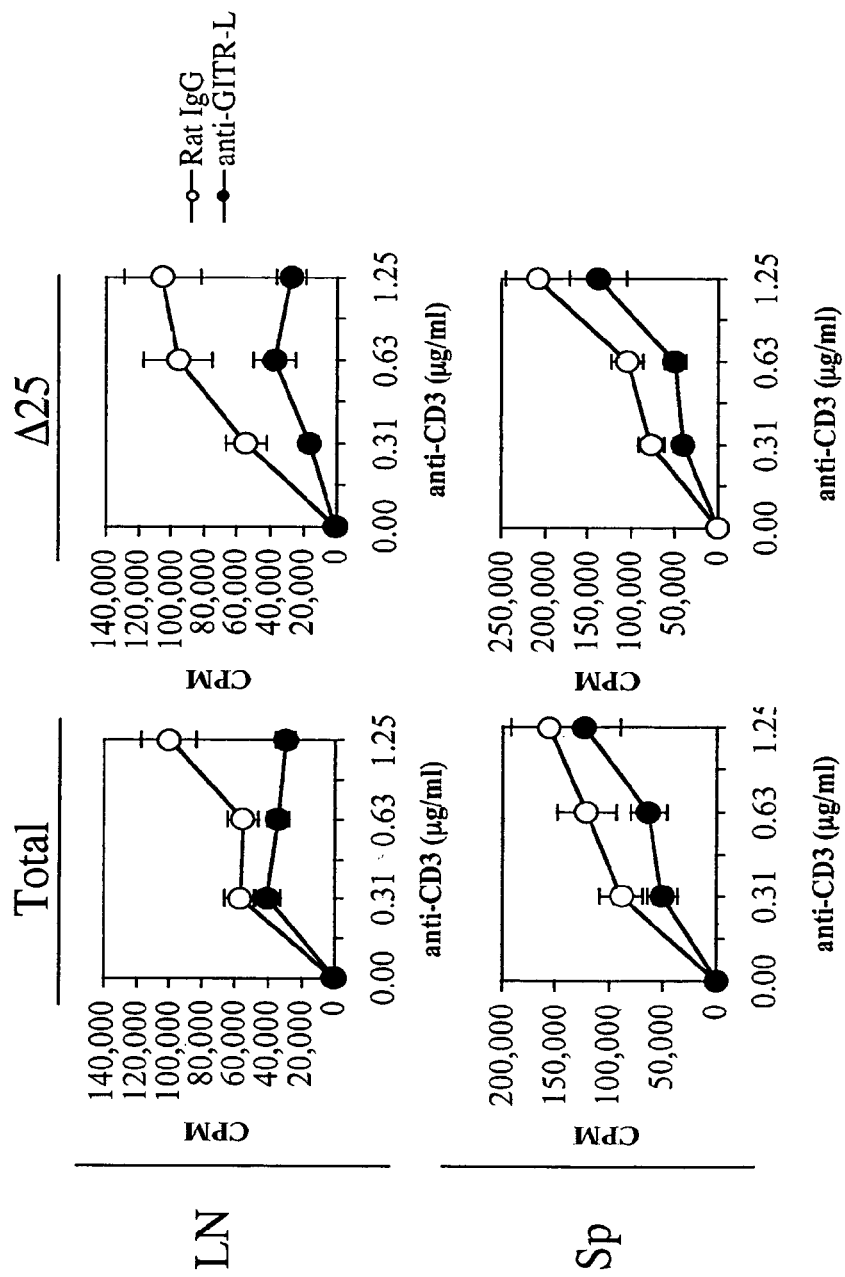
FIG. 9 demonstrates the effects of blocking GITR/GITRL interactions on inhibition of lymphocyte proliferation. For FIGS. 9A and 9B, bars indicate the s.d. values.
Figure 9:
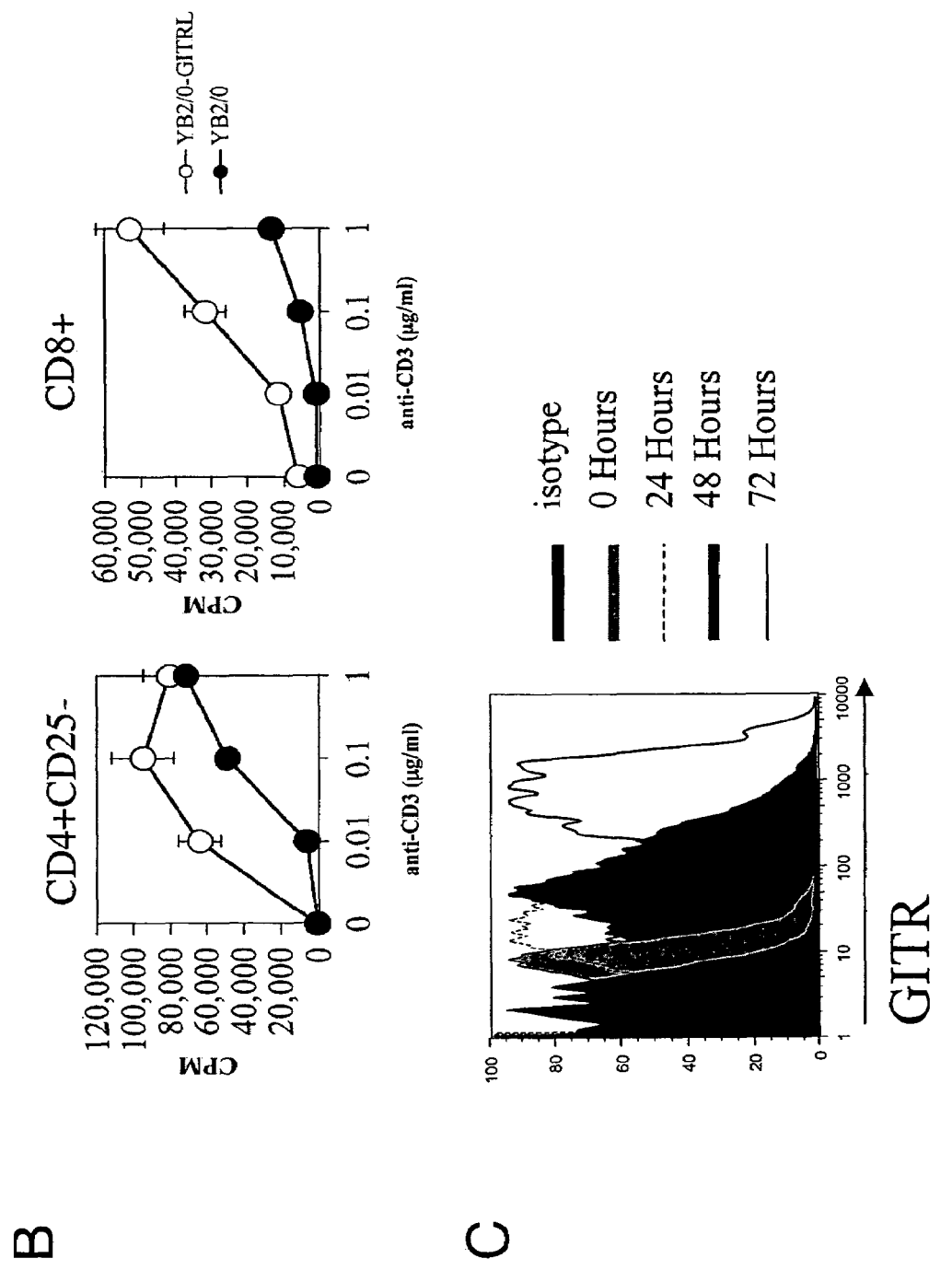

Because GITRL was constitutively expressed by APCs, and because GITR/GITRL interactions were proposed to abrogate the suppressive functions of $CD4^+CD25^+$ T cells, the ability of anti-GITRL antibody to enhance suppression mediated by the endogenous population of $CD4^+CD25^+$ T cells resident in secondary lymphoid organs was tested. A comparison was made of the proliferative responses of total lymph node cells (LN), total splenocytes (Sp), and LN or Sp depleted of $CD25^+$ cells ($\Delta 25$), each of which were cultured with the anti-GITRL antibody (filled circles) or a control antibody (Rat IgG; open circles. The addition of anti-GITRL antibody reduced the proliferative response of total lymph node cells (FIG. 9A, top left) and to a lesser degree, total splenocytes (FIG. 9A, bottom left). However, the inhibitory effect was also apparent in cultures depleted of $CD25^+$ cells (FIG. 9A, top right (LN); bottom right (Sp)), raising the possibility that GITR/GITRL interactions provide costimulatory signals for $CD25^-$ T cells.

To directly test this possibility, the proliferative responses of purified $CD4^+CD25^-$ and $CD8^+$ T cells were examined in the presence of APCs and YB2/0 cells expressing GITRL. The proliferation of both $CD4^+CD25^-$ and $CD8^+$ T cells was substantially enhanced in the presence of GITRL-expressing cells (FIG. 9B), which was particularly evident at low concentrations of anti-CD3 for $CD4^+CD25^-$ T cells.

It may appear discrepant that the anti-GITR antibody mediates its effects by acting on $CD4^+CD25^-$ T cells, as resting T cells express only low levels of GITR. However, the discrepancy is resolved by the demonstration that GITR expression is rapidly upregulated following T cell activation (FIG. 9C), reaching maximal levels between 48 and 72 hours after activation. These results support the possibility GITR/GITRL interactions can influence $CD4^+CD25^-$ T cell activation independently of regulatory $CD4^+CD25^+$ T cells.

Example 10

Reversal of Suppression Requires GITR Expression by $CD25^-$ T Cells

Figure 10:
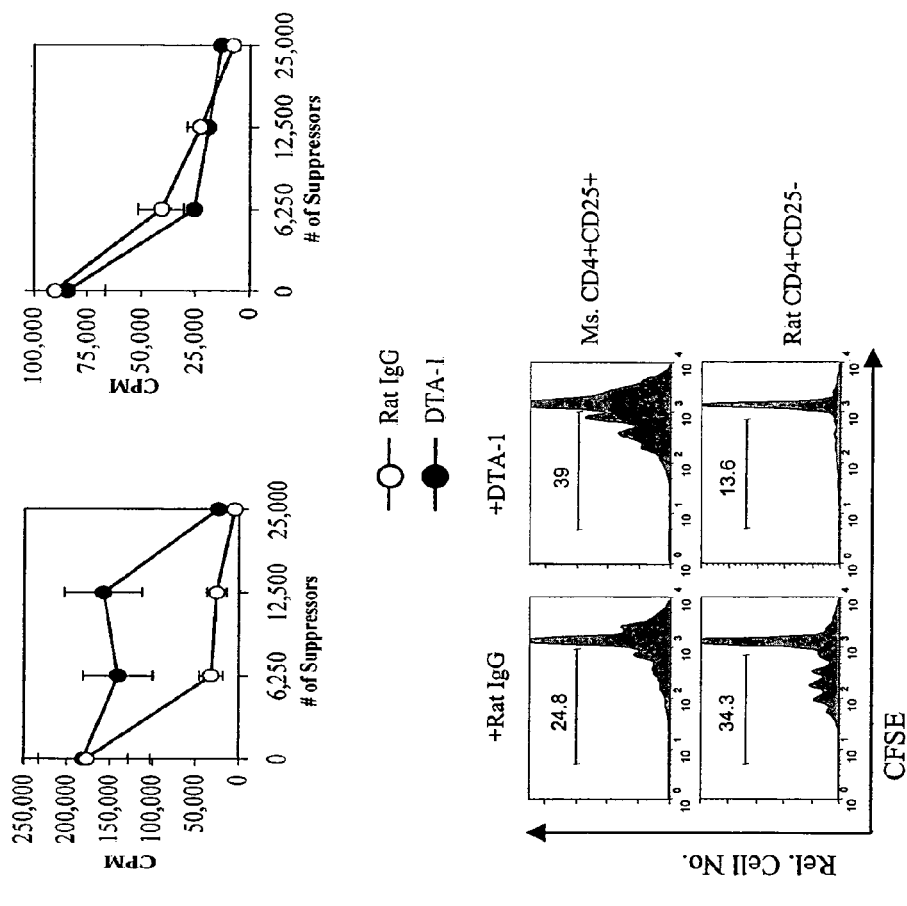
FIG. 10 demonstrates that GITR expression by CD25$^-$ T cells is required to reverse suppression.

Previous studies suggested that ligation of GITR on $CD4^+CD25^+$ T cells inhibited their suppressive capabilities (McHugh et al, 2002; Shimizu et al., 2002). However, because activated T cells also express GITR, we sought to determine the relevant cellular target(s) of GITR engagement resulting in the abrogation of suppression. Proliferation was measured either in the presence or absence of anti-GITR mAb (DTA-1) in cocultures using combinations of $CD4^+CD25^+$ and $CD4^+CD25^-$ T cells from $GITR^{+/+}$ and $GITR^{-/-}$ mice (FIG. 10). As previously reported (Shimizu et al., 2002), when both the $CD4^+CD25^+$ and $CD4^+CD25^-$ T cells expressed GITR, the addition of anti-GITR mAb to cocultures resulted in an increase in the proliferative response compared to cocultures receiving isotype antibody (FIG. 10A, panel a). When $CD4^+CD25^+$, but not $CD4^+CD25^+$, T cells expressed GITR in cocultures, the addition of the anti-GITR antibody led to an enhancement in T cell proliferation similar to that seen when $CD4^+CD25^+$ T cells expressed GITR (FIG. 10A, panel b). However, in cocultures of $CD4^+CD25^-GITR^{-/-}$ and $CD4^+CD25^+ GITR^{+/+}$ T cells, addition of the anti-GITR antibody had no effect on proliferation (FIG. 10A, panel c). As expected, the addition of anti-GITR antibody to cocultures of $CD4^+CD25^-GITR^{-/-}$ and $CD4^+CD25^+ GITR^{-/-}$ T cells also had no effect on T cell proliferation (FIG. 10A, panel d). Results similar to those described above were obtained with a polyclonal anti-mGITR antibody preparation obtained commercially (data not shown).

Strong evidence in support of the hypothesis that the abrogation of suppression was a consequence of ligation of GITR expressed by $CD4^+CD25^+$ T cells was obtained in a previous study, which used combinations of rat responders and mouse $CD4^+CD25^+$ regulatory T cells (Shimizu et al., 2002). The anti-GITR mAb (DTA-1) used in these studies was generated in a rat, and consequently did not bind to rat cells (id.). Experiments analogous to those described above were performed using cocultures of rat $CD4^+CD25^-$ responders, mouse $CD4^+CD25^+$ suppressors, and irradiated rat APCs (FIG. 10B, panel b). Cocultured mouse $CD4^+CD25^-$ responders, mouse $CD4^+CD25^+$ suppressors, and irradiated rat APCs were included as a control (FIG. 10B, panel a). Similar to the data obtained from $GITR^{-/-}$ mice, no abrogation of $CD4^+CD25^+$-mediated suppression occurred (FIG. 10B, panel b), unless GITR could be cross-linked on the responding $CD25^-$ population (FIG. 10B, panel a).

A further analysis of the rat/mouse system was accomplished by examining the dilution of CFSE by cocultured rat $CD4^+CD25^-$ and mouse $CD4^+CD25^+$ T cells by flow cytometry. In the presence of the isotype control antibody, the rat $CD4^+CD25^-$ T cells were only partially suppressed by mouse $CD4^+CD25^+$ T cells when cultured at a 1:8 suppressor to responder ratio (FIG. 10C, left histogram panels). However, the addition of the anti-GITR antibody led to an additional expansion of the mouse $CD4^+CD25^+$ T cells, and a consequent increase in the suppression of the rat T cells (FIG. 10C, right histogram panels). The increased CFSE dilution of mouse $CD4^+CD25^+$ T cells following GITR ligation could be partially inhibited by the addition of blocking anti-CD25 antibodies, suggesting that IL-2 initially made by the responder T cells was also required for this expansion (data not shown). Together, these results unequivocally demonstrate that engagement of GITR on responder $CD4^+CD25^-$ T cells is required to overcome $CD4^+CD25^+$ T cell-mediated suppression.

Example 11

Figure 11:
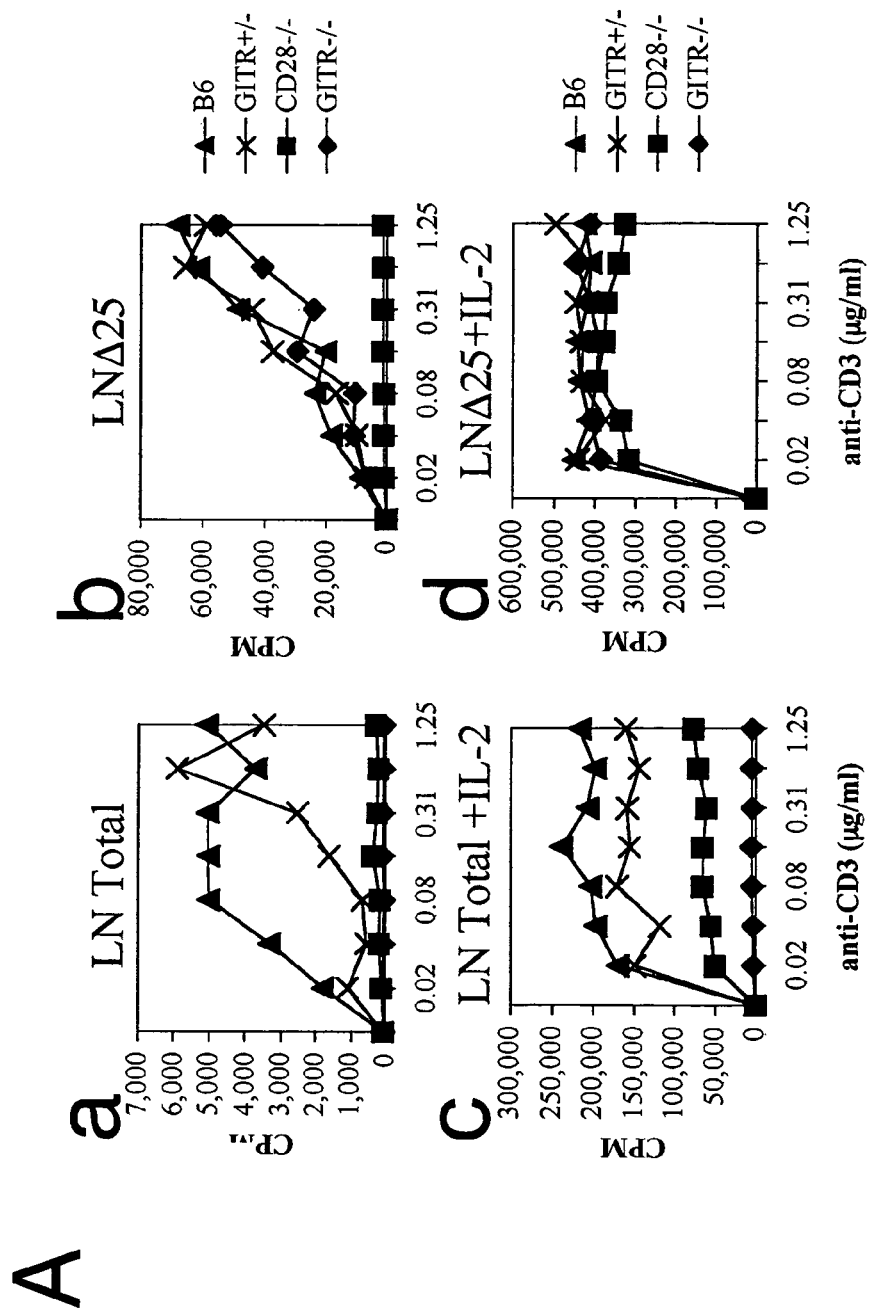
FIG. 11 demonstrates that GITR signals are required to overcome suppression mediated by endogenous regulatory T cells.
Figure 11:
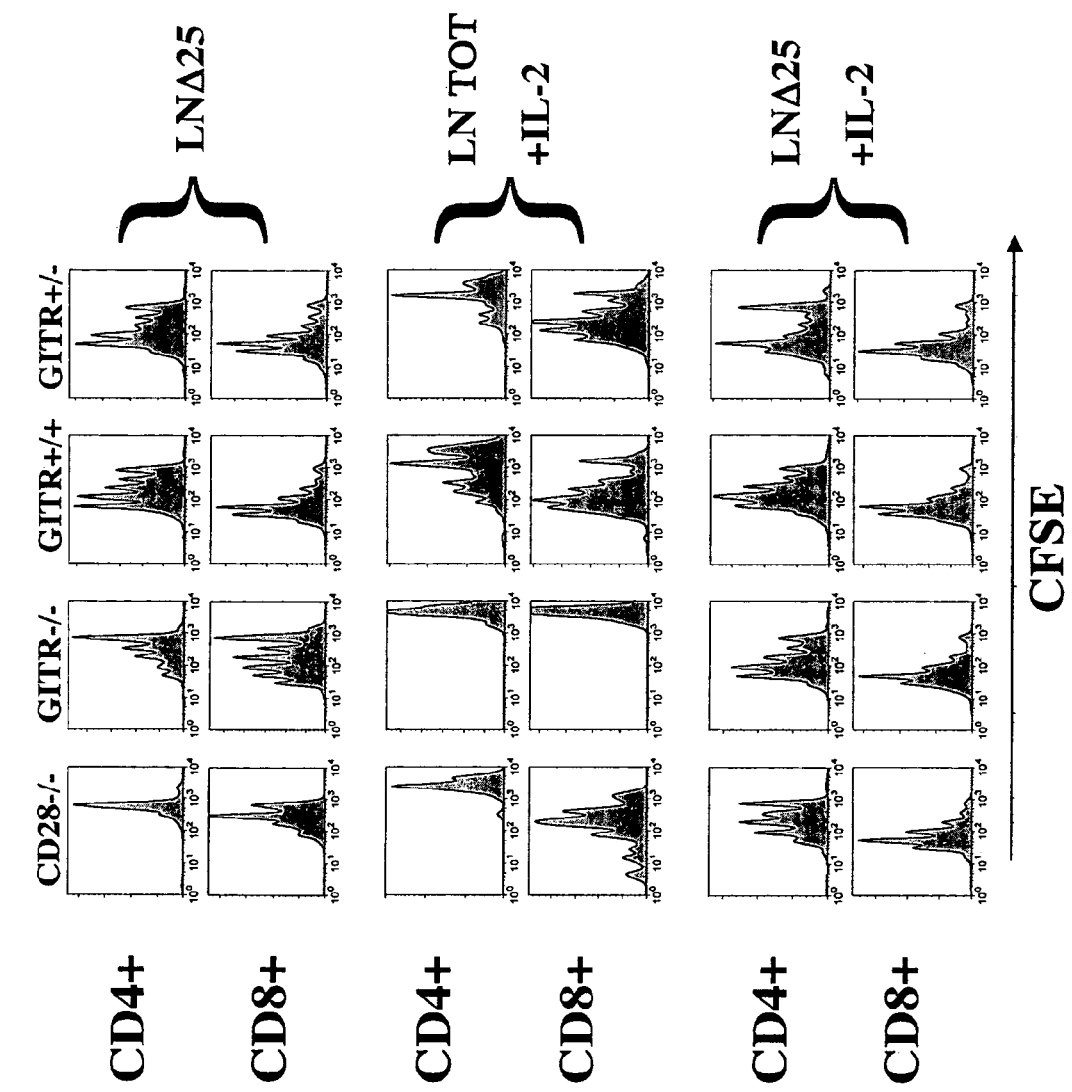
Figure 11:
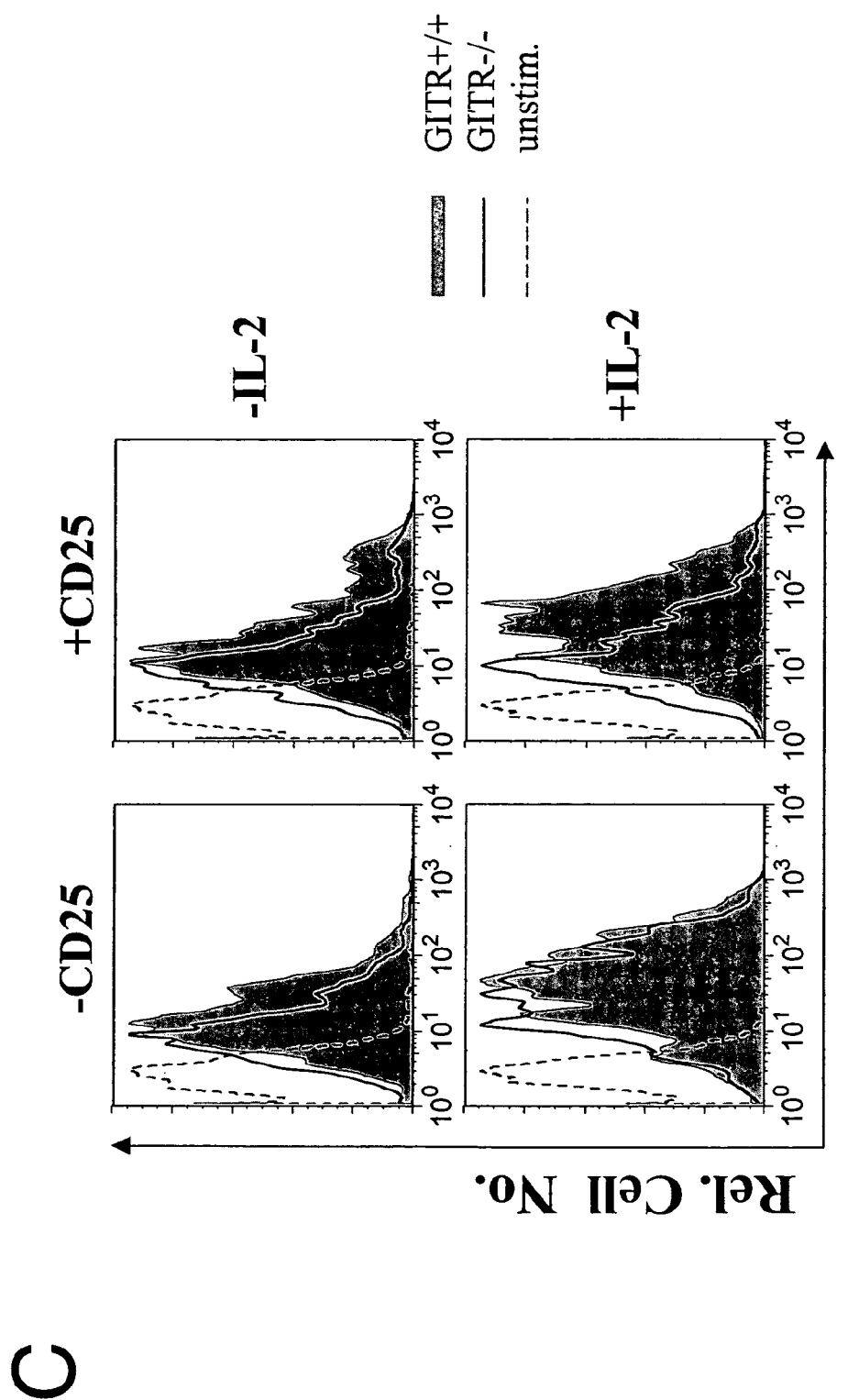

Expression of GITR Signals is Required to Regulate and Overcome Suppression Mediated by Endogenous Regulatory T Cells Since both CD28 and GITR appeared to provide costimulatory signals during the activation of T cells, we sought to determine if they played distinct roles during the primary response. We compared the capacity of GITR and CD28 to promote T cell proliferation in the presence or absence of endogenous lymph node $CD4^+CD25^+$ T cells, and in the presence or absence of exogenous IL-2 (FIG. 11). The same samples used for proliferation studies were simultaneously assessed for CFSE dilution following the 72-hour culture period. In the absence of exogenous IL-2, $CD4^+$ and $CD8^+$ T cells from both GITR$^{-/-}$ and CD28$^{-/-}$ animals failed to proliferate (FIG. 11A, panel a). LN cells from GITR$^{+/-}$ animals displayed a phenotype intermediate between those from wild type and GITR$^{-/-}$ animals (FIG. 11A, panel a). The response of T cells from wild type mice was significantly enhanced following depletion of CD25$^+$ T cells, indicating that suppression under these culture conditions was mediated by the CD25$^+$ T cells resident in the normal lymph node (FIG. 11A, compare panels a and b). Most importantly, in the absence of CD4$^+$CD25$^+$ T cells, the responses of CD4$^+$ and CD8$^+$ lymph node T cells from GITR$^{-/-}$ mice were comparable to those of wild type mice as assessed by $^3$H-thymidine incorporation (FIG. 11A, panel b) and CSFE dilution (FIG. 11B, top set of panels). However, after 72 hours, CD4$^+$ and CD8$^+$ T cells from CD28$^{-/-}$ animals were not proliferating even in the absence of CD4$^+$CD25$^+$ T cells (FIG. 11A, panel b).

A very different pattern of response was observed when exogenous IL-2 was added to the cultures of intact lymph node cells. CD4$^+$ and CD8$^+$ T cell proliferation was completely inhibited in the absence of GITR as assayed by $^3$H-thymidine uptake (FIG. 11A, panel c) or by the lack of CFSE dilution (FIG. 11B, middle set of panels). In contrast, measurable proliferation of T cells from CD28$^{-/-}$ animals was detected by $^3$H-thymidine incorporation (FIG. 11A, panel c), although the CFSE profile demonstrated that CD8$^+$ T cells were largely responsible for the proliferation measured (FIG. 11B). In the presence of IL-2 (50 U/ml), lymph nodes depleted of CD4$^+$CD25$^+$ T cells from all animals displayed similar levels of proliferation as assessed by $^3$H-thymidine incorporation (FIG. 11A, panel d) and CFSE dilution (FIG. 11B, bottom set of panels). Taken together, these results indicate that the defects in T cell activation in GITR$^{-/-}$ and CD28$^{-/-}$ mice are distinct.

The inability of total T cells present in lymph nodes of GITR$^{-/-}$ mice to proliferate in the presence of exogenous IL-2 suggested that the expression of the high affinity IL-2 receptor might be affected in these animals. Since the expression of the IL-2Rα chain is primarily induced by its ligand (Depper et al., 1985; Malek and Ashwell, 1985), the ability of anti-CD3-activated CD4$^+$CD25$^-$ T cells from GITR$^{-/-}$ mice to express this chain was examined in the presence or absence of CD4$^+$CD25$^+$ T cells, and in the presence or absence of IL-2 (FIG. 11C). In the presence of regulatory T cells, the addition of IL-2 to cocultures resulted in enhanced expression of CD25 by GITR$^{+/+}$, but not by GITR$^{-/-}$, CD4$^+$CD25$^-$ T cells after 24 hours (FIG. 11C, bottom right histogram panel). However, the ability of GITR$^{-/-}$ CD4$^+$CD25$^-$ T cells to undergo IL-2-induced CD25 expression could be readily restored by removing CD4$^+$CD25$^+$ T cells (FIG. 11C, bottom left histogram panel). Thus, the impairment in IL-2 responsiveness by GITR$^{-/-}$ T cells in the presence of CD4$^+$CD25$^+$ T cells was due, at least in part, to their inability to express the high affinity IL-2 receptor in the presence of concentrations of exogenous IL-2 sufficient to induce CD25 expression on wild type cells.

Example 12

CD28-dependent Costimulation Enhances GITR Expression and Responsiveness

Figure 12:
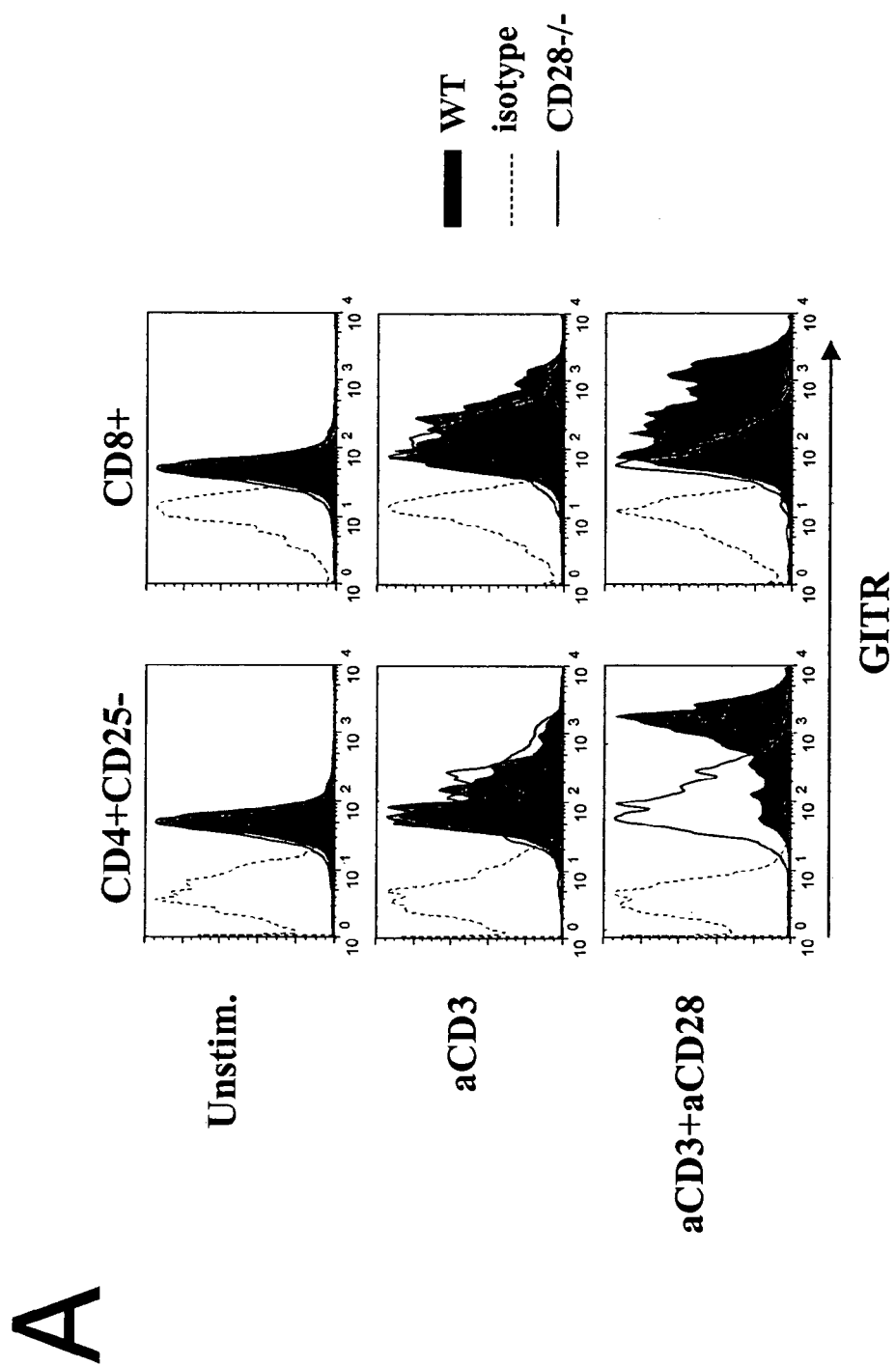
FIG. 12 demonstrates that CD28-dependent costimulation enhances GITR expression and responsiveness.
Figure 12:
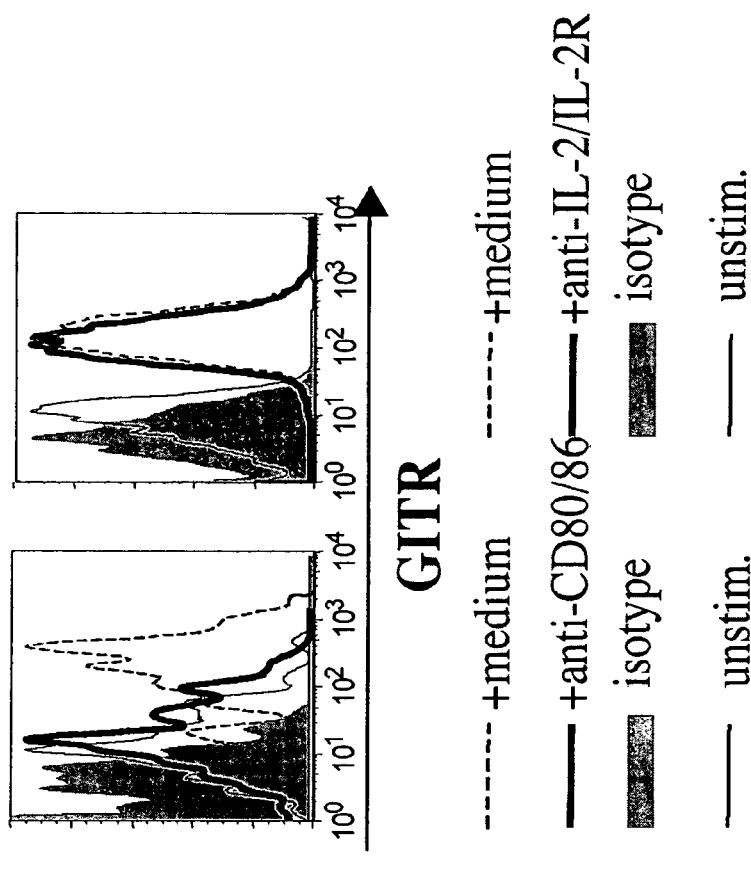

Although the data presented above suggested that engagement of either GITR or CD28 on CD25$^-$ T cells provided a signal that allowed the responder T cells to escape suppression, the nature of the signals involved in this process remained unclear. The partial rescue of the proliferative responses of CD28$^{-/-}$ CD8$^+$ T cells by IL-2 in the presence of CD4$^+$CD25$^+$ T cells suggested that CD28/B7 signaling might regulate T cell sensitivity to GITR/GITRL interactions. Furthermore, previous studies have demonstrated that CD28-80/CD86 interactions can enhance expression of some TNFR-family members (Gilfillan et al., 1998; Rogers et al., 2001). Thus, we examined this possibility with respect to GITR. Purified CD4$^+$CD25$^-$ and CD8$^+$ T cells from CD28$^{-/-}$ or wild type mice either remained unstimulated or were activated with low concentrations of plate-bound anti-CD3 antibody in the presence or absence of plate-bound anti-CD28 antibody (FIG. 12A). Although wild type T cells exposed to anti-CD3 alone only slightly upregulated GITR, the expression of GITR by both CD4$^+$CD25$^-$ and CD8$^+$ T cells was greatly enhanced by the inclusion of anti-CD28.

Similarly, the upregulation of GITR expression on CD4$^+$CD25$^-$ T cells was markedly inhibited by the addition of anti-CD80/CD86 (anti-B7.1/7.2) (FIG. 12B, left histogram panel). The inhibition of GITR expression in cultures containing anti-CD80/CD86 was not secondary to reduced production of IL-2, as GITR upregulation by CD4$^+$CD25$^-$ T cells was not prevented in cultures containing anti-IL-2/IL-2R mAbs (FIG. 12B (right histogram panel).

The enhanced expression of GITR induced by CD28-derived costimulatory signals was paralleled by an enhanced responsiveness to GITR signaling (FIG. 12C). The addition of the anti-GITR antibody substantially enhanced the proliferation of both CD4$^+$ and CD8$^+$ effector T cells from wild type mice (FIG. 12C, left panels). However, when anti-CD80/CD86 was added to these cultures, the presence of the anti-GITR antibody only marginally increased the proliferation of GITR$^{+/+}$CD4$^+$CD25$^-$ T cells (FIG. 12C, GITR$^{+/+}$, top left; GITR$^{-/-}$, top right) and GITR$^{+/+}$CD8$^+$ T cells (FIG. 12C, GITR$^{+/+}$, bottom left; GITR$^{-/-}$, bottom right) over the range of anti-CD3 concentrations tested. Treatment with anti-GITR did not affect the responses of purified CD4$^+$CD25$^-$ and CD8$^+$ T cells from GITR$^{-/-}$ mice (FIG. 12C, right panels). These data suggest that CD28-mediated signals, distinct from costimulation of IL-2 production, enhance GITR expression and facilitate GITR-mediated signaling.

Example 13

GITRL Binding to GITR Provides a Costimulatory Signal to Effector T Cells

Figure 13:
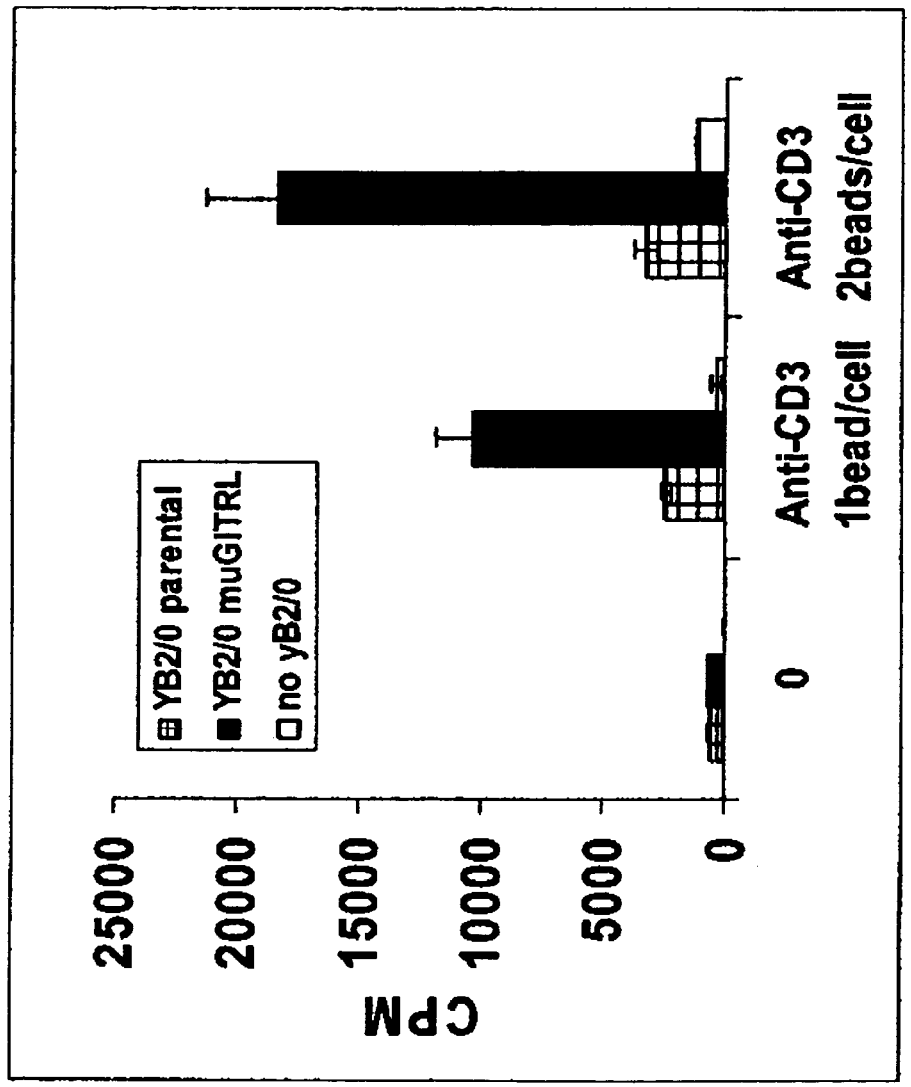
FIG. 13 demonstrates that GITRL binding to GITR provides a costimulatory signal to effector T cells.
Figure 13:
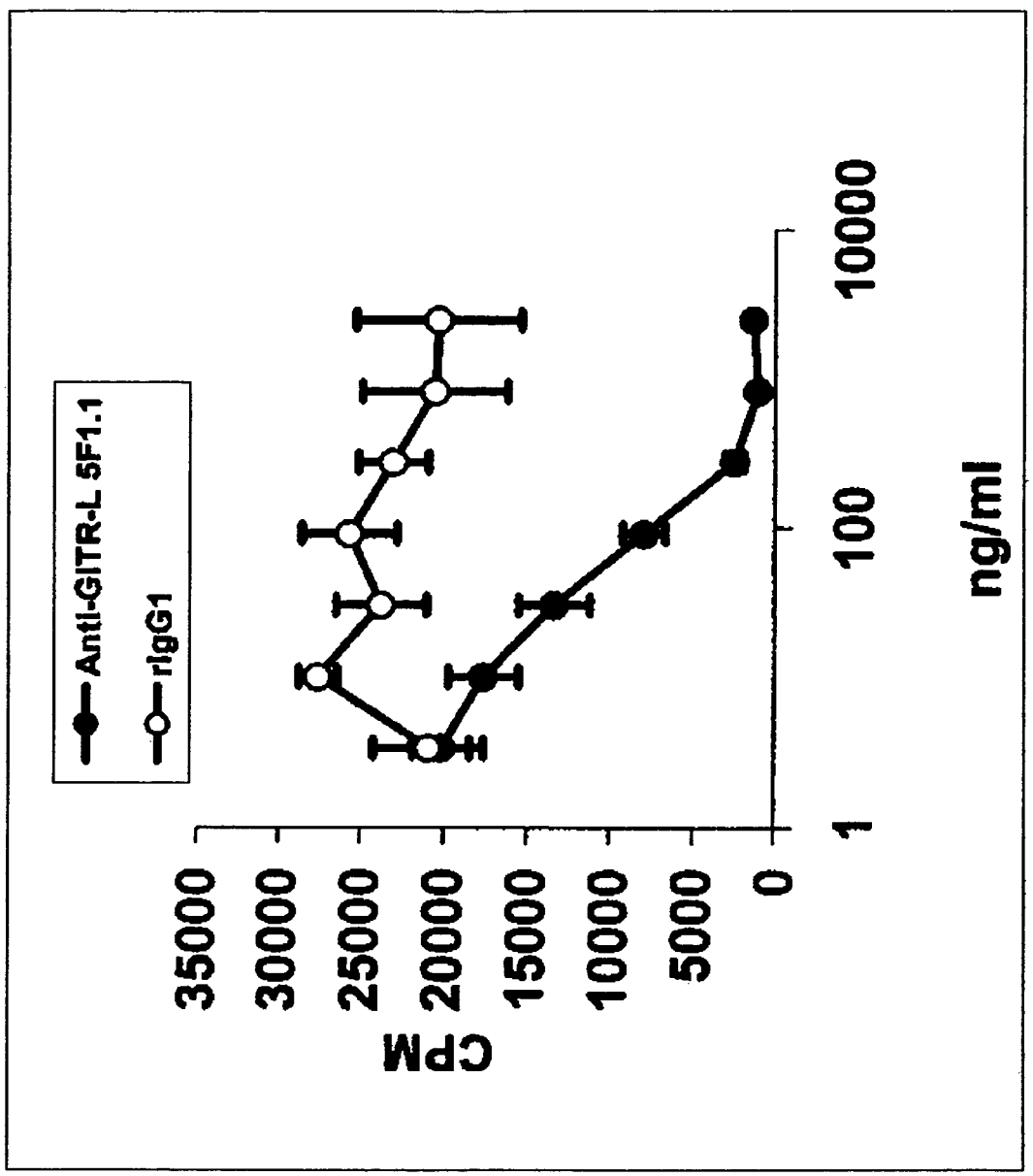
Figure 13:
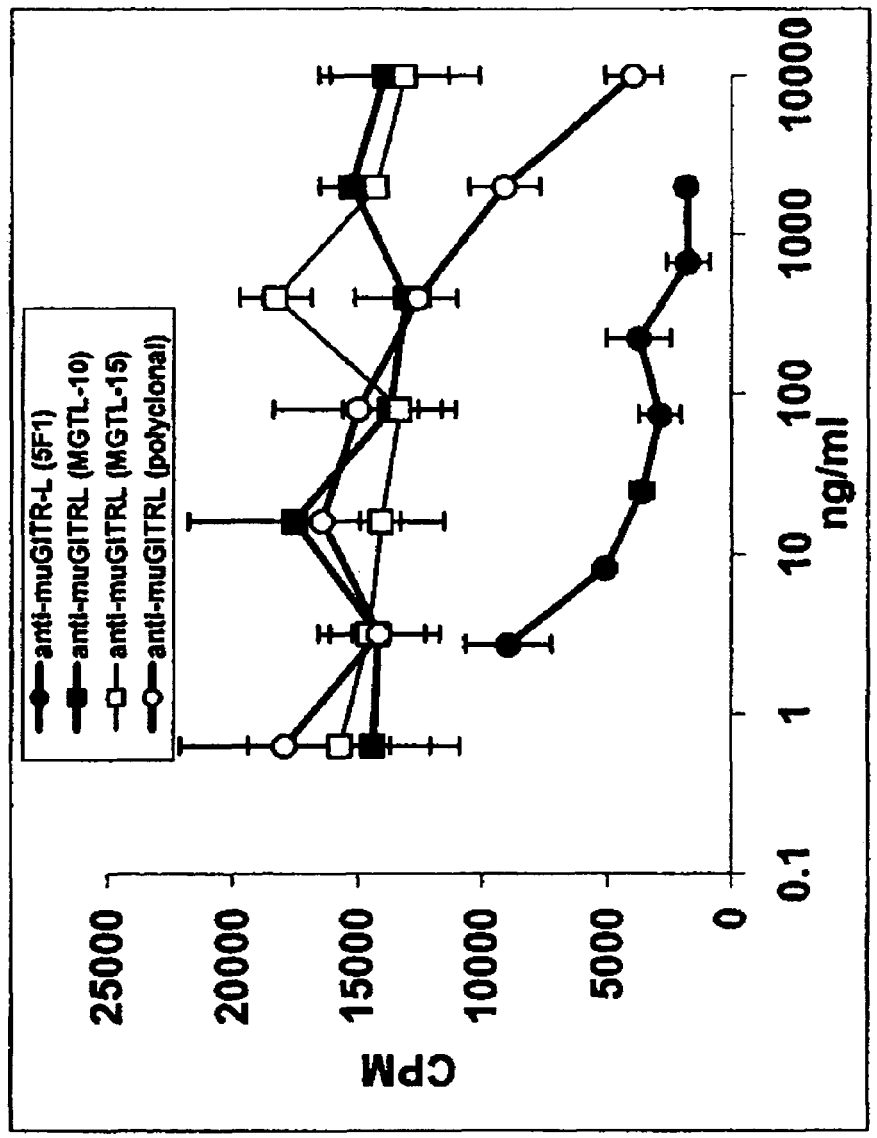

Forty-thousand effector HT-2 T helper cells (GITR$^+$/TCR$^+$) were cultured in the absence or presence of the following reagents: 1) anti-CD3 coated beads at a 1:1 or 1:2 ratio, 2) ten-thousand YB/2 cells that were either not modified to express GITRL (YB2/0 parental) or modified to express GITRL (YB2/0 muGITRL), and-3) increasing concentrations of an isotype control antibody or four different anti-GITRL antibodies (5F1, MGTL-10, MGTL-15, or a polyclonal anti-GITRL antibody). Proliferation was measured by $^3$H-thymidine incorporation for the last 5 hours of a 44-hour culture period. FIG. 13A demonstrates that GITRL enhances the proliferation of T cells stimulated with anti-CD3. Additionally, GITRL-mediated enhancement of T cell proliferation may be blocked with 5F1 antibody, but not the isotype control antibody (FIG. 13B) and commercially available MGTL-10, MGTL-15 and polyclonal anti-GITRL antibodies (FIG. 13C). These data provide further evidence that GITRL provides a costimulatory signal, and also, that 5F1 is a neutralizing antibody to GITRL.

Example 14

Figure 14:
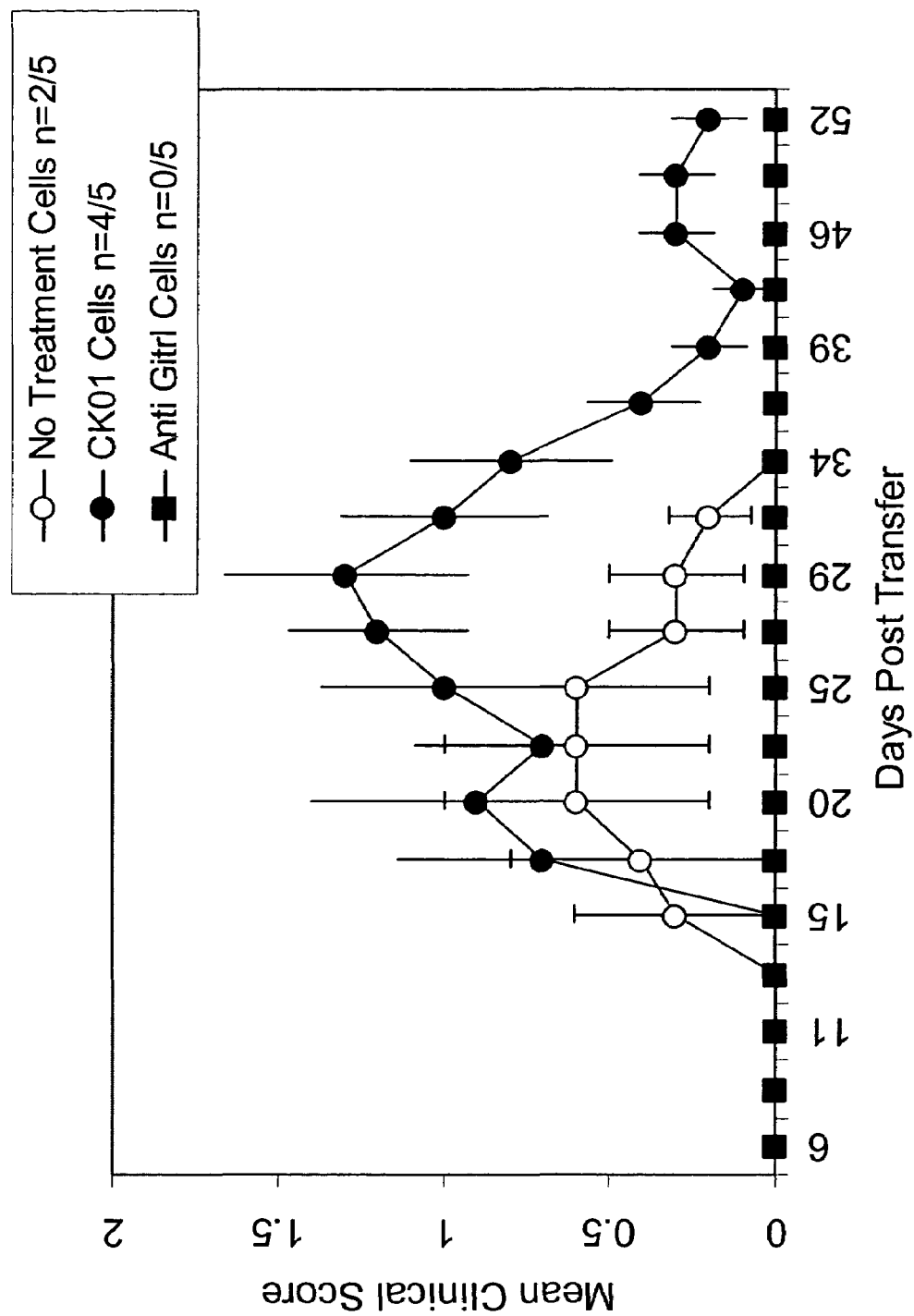
FIG. 14 demonstrates that blocking GITR-GITRL binding with an anti-GITRL antibody prevents adoptive transfer of PLP-induced experimental autoimmune encephalomyelitis (EAE). The incidence of EAE in mice was assessed. Mice were injected with 5×10$^6$ splenocytes that were isolated from female SLJ mice immunized with 150 µg PLP peptide and restimulated ex vivo for 3 days in three different conditions: 10 µg/ml PLP alone (open circles), 10 µg/ml PLP and 10 µg/ml of an isotype control antibody (CKO1; filled circles), or 10 µg/ml PLP and anti-GITRL antibody (5F1.1; filled squares). The incidence of EAE was monitored for 52 days (x-axis) and scored on a scale of 0 to 5 (y-axis).

Blocking GITR-GITRL Binding with an Anti-GITRL Antibody Prevents Adoptive Transfer of PLP Induced Experimental Autoimmune Eencephalomyelitis Nine-week-old female SJL mice were immunized with 150 μg PLP peptide (amino acids 139-151) [HSLGKWLGHP-DKF (SEQ ID NO:12)] in complete Freund's adjuvant. Ten days after immunization, splenocytes were harvested and restimulated ex vivo for 3 days with 10 μg/ml PLP (amino acids 139-151) in the absence (no treatment) or presence of 10 μg/ml antibody (anti-GITRL antibody or control antibody). After restimulation, $5 \times 10^6$ splenocytes were adoptively transferred into 10-week-old naïve SJL mice, and the mice were monitored for 52 days for the experimental autoimmune encephalomyelitis (EAE), as measured on a scale from 0 to 5. EAE developed in 40% and 80% of mice that received splenocytes restimulated in the absence of any antibody (no treatment) and mice that received splenocytes restimulated in the presence of control antibody (CKO), respectively (FIG. 14). Additionally, there was no significance difference in disease scale between animals that received splenocytes with no treatment and animals that received splenocytes treated with control antibody. Significantly, none of the mice that received splenocytes that were restimulated in the presence of anti-GITRL antibody (5F1) developed EAE (p=0.0023 vs. control antibody treatment) (FIG. 14). These data suggest that blockade of the GITR/GITRL pathway will limit the ability of $CD25^-$ T cells to overcome suppression, thereby downmodulating their ability to effect autoimmune responses.

Example 15

Experimental Procedures

Example 15.1:

Antibodies and Reagents

All antibodies used for flow cytometry or functional studies were from BD-Pharmingen, except: tri-color labeled aCD4 (clone CT-CD4) and aB220 (clone RA3-6B2) which were purchased from Caltag (Burlingame, Calif.), and MGTL-10, MGTL-15, and polyclonal anti-GITRL antibodies, which were purchased from Alexis Biochemicals (San Diego, Calif). Purified F(ab')$_2$ fragment of goat-anti-IgM μ-chain was purchased from Jackson Immunoresearch (West Grove, Pa.). Anti-IL-2 (clone S4B6) was used as ascites fluid. Human recombinant IL-2 was obtained from the National Cancer Institute (Frederick, Md.). IL-4, IFN-γ, IL-12, and T cell enrichment columns were purchased from R&D Systems (Minneapolis, Minn.). Poly I:C and LPS were purchased from Sigma. CpGs were purchased from InvivoGen (San Diego, Calif.). Anti-GITRL (clone 5F1; also clone 10F12) and anti-GITR (clone DTA-1) and the PLP peptide were produced "in-house." Anti-B220, -CD11c, -CD11b-CD8, -CD4 and -PE magnetic beads were purchased from Miltenyi (Auburn, Calif.).

Example 15.2

Mice

BALB/c and C57Bl/6 mice (6-8 week old females) were purchased from the NCI Frederick animal facility (Frederick, Md.). $CD28^{-/-}$ mice were provided by Dr. Alfred Singer (NIH/NCI). $GITR^{+/-}$ embryos (Sv129 x B6) were provided by C. Ricarrdi (Perugia University Medical School, Italy) (Ronchetti et al., 2002). The rederived $GITR^{+/-}$ mice were backcrossed once with C57BL/6 mice, and the resulting progeny were screened for the mutant allele by PCR. The identified $GITR^{+/-}$ progeny were then intercrossed to generate $GITR^{-/-}$ mice. All mice were bred and housed at NIH/NIAID facilities under SPF (specific pathogen-free) conditions.

Example 15.3 cDNA Cloning and Expression

The amino acid sequence for human GITRL (GenBank Acc. No. NM_005092) was used to search the Celera database for the mGITRL. Genomic sequence ga_x5j8b7w7wj5_041.cm_aa_2 contained three high scoring pair (HSP) regions. Based on the assumption that these regions correspond to exons for mouse GITRL, primers were designed for PCR amplification. The forward primer (5'-ATGGAGGAAATGCCTTTGAGAG-3') (SEQ ID NO:4) and reverse primer (5'-GAATGGTAGATCAGGCATTAA-GATG-3') (SEQ ID NO:5) amplified a cDNA clone from a mouse thymus library. The resulting fragment was subcloned and the DNA sequence was determined. A subsequent full-length clone was amplified by PCR from the previous construct using 5'-TTTAAAGTCGACCCACCATGGAG-GAAATGCCTTTGAGAG-3' (forward) (SEQ ID NO:6) and 5'-TTTAAAGAATTCTCATTAAGAGAT-GAATGGTAGATCAGGCAT-3' (reverse) (SEQ ID NO:7) primers. The resulting PCR fragment was subcloned into the GFP-RV retroviral vector (Ouyang et al., 1998), and sequence determination of the final cDNA clone was performed. This vector was then transfected into the Phoenix cell line. Supernatants from the transfected Phoenix cells were used to transduce the YB2/0 cell line. GFP-expressing YB2/0 cells were then FACS sorted and maintained in culture. The predicted mGITRL amino acid sequence is identical to that of another group (Kim et al., 2003), except for the substitution of an alanine for a valine at amino acid position 48 in their sequence.

Example 15.4

Production and Purification of Monoclonal Antibodies

Lewis rats were immunized once s.q. with $100 \times 10^6$ YB2/0-GITRL cells in CFA. Two weeks later, these rats were immunized s.q. with $100 \times 10^6$ YB2/0-GITRL cells in IFA. Two weeks later, rats were boosted with $50 \times 10^6$ YB2/0-GITRL cells in PBS. Four days later, the spleen was harvested and cell fusion was performed as previously described (Coligan et al., 2003). The supernatants from the resulting hybridomas were screened by flow cytometry using Phoenix-GITRL and Phoenix cells. Antibodies were purified from cell culture supernatants using protein G-loaded columns, and eluted antibodies were dialyzed against PBS.

Example 15.5

Cell Purification

T cells were purified from peripheral lymph nodes of mice. $CD25^+$ T cells were labeled with magnetic beads and purified on an autoMACS (Miltenyi Biotech, Auburn, Calif.) according to the manufacturer's protocol. Purity of the $CD25^+$ cells was typically between 97 to 99 percent. Cells remaining in the negative fraction were subsequently labeled with either anti-CD4 or anti-CD8 microbeads and purified using the positive selection procedure on the autoMACS. Purity was routinely 90-95 percent. T cell-depleted spleen suspensions were prepared from erythrocyte-lysed suspensions by depleting $Thy1.2^+$ cells using the autoMACS. $B220^+$ cells were purified from splenocytes in a similar fashion using anti-B220 microbeads (Miltenyi Biotech, Auburn, Calif.), and purity of the resulting preparations was routinely greater than 90%. Peritoneal cells were prepared by flushing the peritoneal cavity (PerC) with 10 ml of cold HBSS. For splenic DCs, splenocyte suspensions were prepared in a manner similar to that described (Vremec et al., 2000). Splenic DCs were then purified from the suspensions using anti-CD11c microbeads (Miltenyi Biotech, Auburn, Calif.). The resulting DC suspensions were routinely 85 to 90 percent pure. Rat $CD4^+CD25^-$ cells were generated by depleting rat splenocytes of $CD25^+$ cells using PE-anti-rat CD25 (OX-39) antibodies followed by anti-PE microbeads. After depletion, $CD4^+$ cells were then selected from the depleted fraction using anti-rat-CD4 microbeads.

Example 15.6

In vitro Proliferation Assays

Suppression assays were performed as described (Thornton and Shevach, 1998). Briefly, ($5\times10^4$) cells were cocultured in FBS-supplemented RPMI 1640 (Atlanta Biologicals, Atlanta, Ga.) with irradiated (3000R), T cell-depleted splenocytes ($5\times10^4$) in the presence of 0.5 μg/ml anti-CD3 mAb (2C11) in 96-well flat-bottom plates. To some cultures, antibodies specific for GITR or a Rat Ig isotype were added at a final concentration of 2 μg/ml. Titrated numbers of $CD4^+ CD25^+$ cells were added at final suppressor to responder ratios of 0:1, 1:2, 1:4, or 1:8. Cultures were pulsed with 1 μCi of $^3H$-thymidine for the final 5-8 hours of a 72-hour culture, and were performed in triplicate unless otherwise indicated. Cocultures of rat and mouse T cell subsets were setup in a similar manner except irradiated (3000R) CD4-depleted rat splenocytes were used as APCs, and rat and mouse T cells were stimulated using a cocktail of anti-rat-CD3 (0.25 μg/ml) and anti-mouse-CD3 (0.25 μg/ml) mAbs.

Example 15.7

In vitro Culture of Lymph Node Cells and CFSE Labeling $CD25^+$-depleted lymph node cell suspensions were prepared on the autoMACS as described above. Cells were labeled with CFSE at a concentration of 2 μM for 8 minutes in a 37° C. water bath. Cells were then washed in complete RPMI 1640. Cells ($5\times10^4$/well) were then cultured in 96-well plates in the presence or absence of rhIL-2 (50 U/ml). Duplicate wells were either pulsed with 1 μCi of $^3H$-thymidine for the final 5-8 hours of a 72-hour culture or used for analysis of CFSE dilution.

Example 16

Discussion

The role of GITR in the function of $CD4^+CD25^+$ T cells was inferred from the demonstration that both polyclonal and monoclonal antibodies to GITR reversed the suppressive effects of $CD4^+CD25^+$ T cells when added to cocultures of $CD25^+$ and $CD25^-$ T cells (McHugh et al., 2002; Shimizu et al., 2002). The $CD4^+CD25^+$ T cells appeared to be the likely target for the anti-GITR reagents because freshly explanted $CD25^+$ T cells expressed GITR at higher levels than resting $CD25^-$ T cells and because anti-GITR antibody together with IL-2 triggered the proliferation of $CD25^+$, but not $CD25^+$, T cells in the absence of a TCR signal. Furthermore, when Shimizu et al added a rat anti-mGITR mAb, which was nonreactive with rat cells, to cocultures of mouse $CD25^+$ suppressors and rat responder T cells, a reversal of suppression was observed. These studies led to the hypothesis that engagement of GITR by agonistic anti-GITR antibodies and, presumably, by its physiological ligand, generated a signal that both inhibited the suppressor activity of $CD4^+CD25^+$ T cells and reversed the nonresponsiveness of the $CD25^+$ T cells to exogenous IL-2.

Experiments were designed to attempt to extend and confirm these studies by cloning the mouse GITRL, analyzing its tissue distribution, and definitively determining the target for the agonistic anti-GITR antibodies by using mixtures of $CD25^+$ and $CD25^-$ T cells from wild type and $GITR^{-/-}$ mice. Collectively, the studies demonstrate that the anti-GITR antibodies and GITRL abrogate the suppressive effects of $CD4^+ CD25^+$ T cells by providing $CD25^-$ T cells a unique signal that raises their threshold for suppression by $CD4^+CD25^+$ T cells. The studies indicate that GITRL is selectively expressed on the cell surface of APC, with the highest level of expression on B-1 B lymphocytes; intermediate levels on conventional B-2 B lymphocytes, macrophages, and $B220^+$ DCs; and lower levels on $B220^-$ DC subsets. GITRL is unique among members of the TNF superfamily in that it is expressed on resting APC, and its expression is downregulated by triggering the B cell receptor, CD40, or different Toll-like receptors. Other members of the TNF superfamily (4-1BB-L, OX40-L, LIGHT, CD70, CD30-L) are not detectable on resting APC, and their expression is upregulated by activation of the APC via Toll-like receptor stimulation (Croft, 2003). The present studies do not address whether the downregulation of GITRL expression from the cell surface is accompanied by secretion of soluble GITRL, but Tone et al. (2003) have reported that LPS stimulation of DC, macrophages and B cells results in downregulation of GITRL mRNA. The expression of GITRL on resting APC strongly suggests that it functions early in the process of T cell activation. Other cell types, including endothelial cells (Gurney et al., 1999; Kwon et al., 1999), activated T cells, and certain subsets of DN thymocytes were also shown to express GITRL, and the function of this molecule on these latter cell types remains to be determined.

The ability of both the anti-GITR antibodies and the GITRL expressing cells to enhance the activation of $CD25^-$ T cells alone, as well as the ability of anti-GITRL to partially inhibit the activation of $CD25^-$ T cells in the absence of $CD25^+$ T cells, prompted a careful reexamination of the cellular target(s) of these reagents. The addition of anti-GITR to cocultures of CD25+ and CD25− T cells from wild type and GITR−/− mice demonstrated that the target for the antibody-mediated reversal of suppression was the CD25− T cell. This was further supported by experiments using rat CD25− responder and mouse CD25+ suppressor T cells in cocultures, which conclusively demonstrated GITR ligation on the CD25+ T cell subset does not abrogate their suppressive function. In fact, an examination of CFSE dilution demonstrated that GITR ligation promoted the expansion of CD25+ T cells in cocultures, which ultimately enhanced the suppression of the rat CD25− responders. Therefore, it is possible that the enhancement in proliferation in anti-GITR-treated rat/mouse cocultures reported by Shimizu et al (2002), which was presumed to be due to rat T cells, actually reflected proliferation of the mouse CD25+ suppressor cells. This would not have been apparent by measuring $^3$H-thymidine incorporation alone.

One previous report suggested that GITR-deficient T cells are hyperreactive to TCR stimulation (Ronchetti et al., 2002). However the extrapolation of those observations to the present observations are difficult as that report did not analyze the responses of purified CD4+, CD8+ T lymphocytes, nor did it evaluate the role of CD4+CD25+ T cells. In the present studies, the responses of highly purified CD4+CD25− and CD8+ T cells from GITR−/− mice were comparable to those of controls. However, in the presence of physiological numbers of regulatory T cells, both CD4+ and CD8+ T cells from GITR−/− animals were completely unresponsive to CD3 cross-linking. This result clearly demonstrates that in the absence of GITR/GITRL interactions suppression is dominant. Indeed, the suppression of activation of CD4+CD25− T cells from GITR−/− mice was so strong that it could not be overcome by the addition of a high concentration of exogenous IL-2, which normally abrogates the suppressive effects of much higher numbers of CD25+ T cells on the responses of wild type CD4+CD25− T cells (Takahashi et al., 1998; Thornton and Shevach, 1998). The suppressive effects of the CD4+ CD25+ were mediated by inhibition of both IL-2 production and expression of CD25 by the CD4+CD25− GITR−/− responder population, which resembles what has been previously described for the effects of CD4+CD25+ T cells on normal CD8+ T cell responses (Piccirillo and Shevach, 2001).

The costimulatory signals delivered by GITR and CD28 appeared to be distinct, but interrelated. In the absence of regulatory T cells, the responses of both CD4+ and CD8+ T cells from GITR−/− mice were identical to those of cells from wild type mice. In contrast, under the culture conditions used in this study, CD4+ and CD8+ T cells from CD28−/− mice were nonresponsive. Conversely, when IL-2 was added to cultures containing regulatory T cells, the responses of CD4+ and CD8+ T cells from the GITR−/− mice were not restored, while the responses of CD8+ cells from the CD28−/− mice were partially restored. On the other hand, a potential cooperative relationship and shared signaling hierarchy between CD28 and GITR was supported by the demonstration that (1) CD4+CD25− and CD8 T cells failed to upregulate GITR in the absence of CD28 cross-linking and (2) anti-CD80/CD86 antibodies markedly inhibited both the upregulation of GITR expression and responsiveness to anti-GITR antibodies. Thus, the results suggest that an additional important function of the CD28-CD80/CD86 signaling pathway during T cell activation is to license T cell resistance to CD25+-mediated suppression by enhancing the expression and function of GITR.

Similar to the results suggested by other published studies (Shimizu et al., 2002; Tone et al., 2003), these studies indicate that ligation of GITR on CD25− T cells, in the absence of regulatory T cells, did provide some degree of costimulation. However, GITR ligation is not required for costimulating CD25− T cells in the same manner as CD28, as CD4+CD25− and CD8 T cells from GITR−/− mice respond similar to wild type T cells. We favor the view that engagement of GITR on both CD4+CD25− and CD8+ effector T cells by GITRL early during the course of an immune response serves primarily to render the effector population resistant, e.g., less susceptible, to the suppressive effects of the CD4+CD25+ T cells. During the course of the response, inflammatory signals ultimately result in the downregulation of GITRL expression, thereby increasing the susceptibility of the effector cells to CD25+-mediated suppression. Although only limited data is available as to when CD25+-mediated suppression of immune responses to infectious agents occurs in vivo, some studies have suggested that it operates at the contraction, rather than the initiation, phase of the response to prevent tissue damage secondary to exuberant inflammation (Suvas et al., 2003). It should be pointed out that engagement of GITR on CD25+ T cells in the presence of IL-2 induces their expansion (McHugh et al., 2002). It remains possible that in vivo engagement of GITR on CD25+ T cells by GITRL on resting APC results in the nonspecific expansion of regulatory T cells in the presence of IL-2 secreted by effector T cells early in the course of the immune response. This nonspecific expansion may be critical to the subsequent generation of a pool of antigen-specific suppressor cells that function to inhibit effector cell activity later in the response.

We have previously proposed that manipulation of GITR/GITRL interactions may prove to be an effective way of manipulating regulatory T cell function in vivo (McHugh and Shevach, 2002). Although this concept was based on data suggesting that the CD4+CD25+ T cell was the target of the anti-GITR antibody, it is still the case that the GITR/GITRL interaction represents an important therapeutic target. Thus, treatment with an agonistic anti-GITR antibody or an agonistic GITRL-Fc should render effector cells resistant, e.g., less susceptible, to the suppressive effects of CD4+CD25+ T cells and should prove to be effective for treating cancers and infectious diseases, for enhancement of immune responses to cancers (used alone or in combination with other tumor therapies, such as tumor vaccines), and for enhancement of immune responses to infectious pathogens, including viruses, bacteria, etc. (used alone or in combination with other therapies for infectious pathogens, such as a vaccine adjuvant to weak vaccines for infectious agents). Similarly, inhibition of GITR/GITRL interactions with a GITR agonist, e.g., through the use of a neutralizing anti-GITRL antibody or GITR-Fc, should lower the threshold of effector T cells to suppression and thus be useful for the prevention and/or treatment of autoimmune disorders, inflammatory diseases, transplant (or graft) rejection, and graft-versus-host disease.

REFERENCES

The following references are full citations for several author/year citations in the specification:

Aseffa, A., Gumy, A., Launois, P., MacDonald, H. R., Louis, J. A., and Tacchini-Cottier, F. (2002). The early IL-4 response to Leishmania major and the resulting Th2 cell maturation steering progressive disease in BALB/c mice are subject to the control of regulatory CD4+CD25+ T cells. J. Immunol 169, 3232-3241.

Banchereau, J., and Steinman, R. M. (1998). Dendritic cells and the control of immunity. Nature 392, 245-252.

Belkaid, Y., Piccirillo, C. A., Mendez, S., Shevach, E. M., and Sacks, D. L. (2002). CD4+CD25+regulatory T cells control Leishmania major persistence and immunity. Nature 420, 502-507.

Coligan, J. E., Kruisbeek, A. M., Margulies, D. H., Shevach, E. M., and Strober, W., eds. (2003). Current Protocols in Immunology (John Wiley & Sons, Inc.).

Croft, M. (2003). Co-stimulatory members of the TNFR family: keys to effective T-cell immunity? Nat Rev Immunol 3, 609-620.

Depper, J. M., Leonard, W. J., Drogula, C., Kronke, M., Waldmann, T. A., and Greene, W. C. (1985). Interleukin 2 (IL-2) augments transcription of the IL-2 receptor gene. Proc Natl Acad Sci U S A 82, 4230-4234.

Gavin, M. A., Clarke, S. R., Negrou, E., Gallegos, A., and Rudensky, A. (2002). Homeostasis and anergy of CD4(+)CD25(+) suppressor T cells in vivo. Nat Immunol 3, 33-41.

Gilfillan, M. C., Noel, P. J., Podack, E. R., Reiner, S. L., and Thompson, C. B. (1998). Expression of the costimulatory receptor CD30 is regulated by both CD28 and cytokines. J. Immunol 160, 2180-2187.

Godfrey, D. I., Kennedy, J., Suda, T., and Zlotnik, A. (1993). A developmental pathway involving four phenotypically and functionally distinct subsets of CD3-CD4-CD8-triple-negative adult mouse thymocytes defined by CD44 and CD25 expression. J. Immunol 150, 4244-4252.

Gurney, A. L., Marsters, S. A., Huang, R. M., Pitti, R. M., Mark, D. T., Baldwin, D. T., Gray, A. M., Dowd, A. D., Brush, A. D., Heldens, A. D., et al. (1999). Identification of a new member of the tumor necrosis factor family and its receptor, a human ortholog of mouse GITR. Curr Biol 9, 215-218.

Hisaeda, H., Maekawa, Y., Iwakawa, D., Okada, H., Himeno, K., Kishihara, K., Tsukumo, S., and Yasutomo, K. (2004). Escape of malaria parasites from host immunity requires CD4(+)CD25(+) regulatory T cells. Nat Med 10, 29-30.

Kim, J. D., Choi, B. K., Bae, J. S., Lee, U. H., Han, I. S., Lee, H. W., Youn, B. S., Vinay, D. S., and Kwon, B. S. (2003). Cloning and characterization of GITR ligand. Genes Immun 4, 564-569.

Kursar, M., Bonhagen, K., Fensterle, J., Kohler, A., Hurwitz, R., Kamradt, T., Kaufmann, S. H., and Mittrucker, H. W. (2002). Regulatory CD4+CD25+ T cells restrict memory CD8+ T cell responses. J Exp Med 196, 1585-1592.

Kwon, B., Yu, K. Y., Ni, J., Yu, G. L., Jang, I. K., Kim, Y. J., Xing, L., Liu, D., Wang, S. X., and Kwon, B. S. (1999). Identification of a novel activation-inducible protein of the tumor necrosis factor receptor superfamily and its ligand. J Biol Chem 274, 6056-6061.

Lundgren, A., Suri-Payer, E., Enarsson, K., Svennerholm, A. M., and Lundin, B. S. (2003). Helicobacter pylori-specific CD4+ CD25high regulatory T cells suppress memory T-cell responses to *H. pylori* in infected individuals. Infect Immun 71, 1755-1762.

Malek, T. R., and Ashwell, J. D. (1985). Interleukin 2 upregulates expression of its receptor on a T cell clone. J Exp Med 161, 1575-1580.

Maloy, K. J., Salaun, L., Cahill, R., Dougan, G., Saunders, N. J., and Powrie, F. (2003). CD4+CD25+ T(R) cells suppress innate immune pathology through cytokine-dependent mechanisms. J Exp Med 197, 111-119.

McHugh, R. S., and Shevach, E. M. (2002). The role of suppressor T cells in regulation of immune responses. J Allergy Clin Immunol 110, 693-702.

McHugh, R. S., Whitters, M. J., Piccirillo, C. A., Young, D. A., Shevach, E. M., Collins, M., and Byrne, M. C. (2002). CD4(+)CD25(+) immunoregulatory T cells: gene expression analysis reveals a functional role for the glucocorticoid-induced TNF receptor. Immunity 16, 311-323.

Nakano, H., Yanagita, M., and Gunn, M. D. (2001). CD11c(+)B220(+)Gr-1(+) cells in mouse lymph nodes and spleen display characteristics of plasmacytoid dendritic cells. J Exp Med 194, 1171-1178.

Ouyang, W., Ranganath, S. H., Weindel, K., Bhattacharya, D., Murphy, T. L., Sha, W. C., and Murphy, K. M. (1998). Inhibition of Th1 development mediated by GATA-3 through an IL-4-independent mechanism. Immunity 9, 745-755.

Piccirillo, C. A., and Shevach, E. M. (2001). Cutting edge: control of CD8+ T cell activation by CD4+CD25+ immunoregulatory cells. J Immunol 167, 1137-1140.

Rogers, P. R., Song, J., Gramaglia, I., Killeen, N., and Croft, M. (2001). OX40 promotes Bcl-xL and Bcl-2 expression and is essential for long-term survival of CD4 T cells. Immunity 15, 445-455.

Ronchetti, S., Nocentini, G., Riccardi, C., and Pandolfi, P. P. (2002). Role of GITR in activation response of T lymphocytes. Blood 100, 350-352.

Sakaguchi, S., Sakaguchi, N., Asano, M., Itoh, M., and Toda, M. (1995). Immunologic self-tolerance maintained by activated T cells expressing IL-2 receptor alpha-chains (CD25). Breakdown of a single mechanism of self-tolerance causes various autoimmune diseases. J Immunol 155, 1151-1 164.

Shimizu, J., Yamazaki, S., Takahashi, T., Ishida, Y., and Sakaguchi, S. (2002). Stimulation of CD25(+)CD4(+) regulatory T cells through GITR breaks immunological self-tolerance. Nat Immunol 3, 135-142.

Suvas, S., Kumaraguru, U., Pack, C. D., Lee, S., and Rouse, B. T. (2003). CD4+CD25+ T cells regulate virus-specific primary and memory CD8+ T cell responses. J Exp Med 198, 889-901.

Takahashi, T., Kuniyasu, Y., Toda, M., Sakaguchi, N., Itoh, M., Iwata, M., Shimizu, J., and Sakaguchi, S. (1998). Immunologic self-tolerance maintained by CD25+CD4+ naturally anergic and suppressive T cells: induction of autoimmune disease by breaking their anergic/suppressive state. Int Immunol 10, 1969-1980.

Thornton, A. M., and Shevach, E. M. (1998). CD4+CD25+ immunoregulatory T cells suppress polyclonal T cell activation in vitro by inhibiting interleukin 2 production. J Exp Med 188, 287-296.

Tone, M., Tone, Y., Adams, E., Yates, S. F., Frewin, M. R., Cobbold, S. P., and Waldmann, H. (2003). Mouse glucocorticoid-induced tumor necrosis factor receptor ligand is costimulatory for T cells. Proc Natl Acad Sci U S A 100, 15059-15064.

Uraushihara, K., Kanai, T., Ko, K., Totsuka, T., Makita, S., Iiyama, R., Nakamura, T., and Watanabe, M. (2003). Regulation of murine inflammatory bowel disease by CD25+ and CD25− CD4+ glucocorticoid-induced TNF receptor family-related gene+ regulatory T cells. J Immunol 171, 708-716.

Vremec, D., Pooley, J., Hochrein, H., Wu, L., and Shortnan, K. (2000). CD4 and CD8 expression by dendritic cell subtypes in mouse thymus and spleen. J Immunol 164, 2978-2986.

Vremec, D., and Shortman, K. (1997). Dendritic cell subtypes in mouse lymphoid organs: cross-correlation of surface markers, changes with incubation, and differences among thymus, spleen, and lymph nodes. J Immunol 159, 565-573.

Yu, K. Y., Kim, H. S., Song, S. Y., Min, S. S., Jeong, J. J., and Youn, B. S. (2003). Identification of a ligand for glucocorticoid-induced tumor necrosis factor receptor constitutively expressed in dendritic cells. Biochem Biophys Res Commun 310, 433-438.

What is claimed:

1. A method of treating or ameliorating an immune cell-associated pathology in a subject for whom suppression of immune response is desired, wherein the immune cell is a T cell, comprising administering to the subject a therapeutically effective amount of a neutralizing anti-Glucocorticoid-Induced TNF Receptor Ligand antibody (anti-GITRL antibody), wherein the anti-GITRL antibody is a 5F1 antibody, a 10F12 antibody, or an antigen-binding fragment thereof, and wherein the anti-GITRL antibody treats or ameliorates the immune cell-associated pathology by blocking GITRL binding to the Glucocorticoid-Induced TNF Receptor (GITR) on effector T cells, and wherein the immune cell-associated pathology is selected from the group consisting of rheumatoid arthritis, encephalomyelitis, multiple sclerosis, osteoarthritis, autoimmune gastritis, psoriasis and other inflammatory dermatoses, asthma, allergy, organ transplant rejection, graft-versus-host disease, and inflammatory bowel diseases, including Crohn's disease and ulcerative colitis.

2. The method of claim 1, wherein the method comprises administering the anti-GITRL antibody such that the susceptibility of effector T cells in the subject to suppression by $CD4^+CD25^+$ regulatory T cells is maintained.

3. The method of claim 1, wherein the immune cell-associated pathology is multiple sclerosis.

4. The method of claim 1, where in the effector T cells are $CD4^+CD25^-$ T cells.

* * * * *

UNITED STATES PATENT AND TRADEMARK OFFICE
CERTIFICATE OF CORRECTION

PATENT NO. : 7,618,632 B2
APPLICATION NO. : 10/853032
DATED : November 17, 2009
INVENTOR(S) : Collins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 331 days.

Signed and Sealed this

Twenty-sixth Day of October, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 522
<212> TYPE: DNA
<213> ORGANISM: Mus musculus
<220> FEATURE:
<221> NAME/KEY: CDS
<222> LOCATION: (1)..(522)

<400> SEQUENCE: 1

```
atg gag gaa atg cct ttg aga gag tca agt cct caa agg gca gag agg      48
Met Glu Glu Met Pro Leu Arg Glu Ser Ser Pro Gln Arg Ala Glu Arg
1               5                   10                  15 tgc aag aag tca tgg ctc ttg tgc ata gtg gct ctg tta ctg atg ctg      96
Cys Lys Lys Ser Trp Leu Leu Cys Ile Val Ala Leu Leu Leu Met Leu
                20                  25                  30 ctc tgt tct ttg ggt aca ctg atc tat act tca ctc aag cca act gcc     144
Leu Cys Ser Leu Gly Thr Leu Ile Tyr Thr Ser Leu Lys Pro Thr Ala
            35                  40                  45 atc gag tcc tgc atg gtt aag ttt gaa cta tca tcc tca aaa tgg cac     192
Ile Glu Ser Cys Met Val Lys Phe Glu Leu Ser Ser Ser Lys Trp His
        50                  55                  60 atg aca tct ccc aaa cct cac tgt gtg aat acg aca tct gat ggg aag     240
Met Thr Ser Pro Lys Pro His Cys Val Asn Thr Thr Ser Asp Gly Lys
65                  70                  75                  80 ctg aag ata ctg cag agt ggc aca tat tta atc tac ggc caa gtg att     288
Leu Lys Ile Leu Gln Ser Gly Thr Tyr Leu Ile Tyr Gly Gln Val Ile
                85                  90                  95 cct gtg gat aag aaa tac ata aaa gac aat gcc ccc ttc gta gta cag     336
Pro Val Asp Lys Lys Tyr Ile Lys Asp Asn Ala Pro Phe Val Val Gln
                100                 105                 110 ata tat aaa aag aat gat gtc cta caa act cta atg aat gat ttt caa     384
Ile Tyr Lys Lys Asn Asp Val Leu Gln Thr Leu Met Asn Asp Phe Gln
            115                 120                 125 atc ttg cct ata gga ggg gtt tat gaa ctg cat gct gga gat aac ata     432
Ile Leu Pro Ile Gly Gly Val Tyr Glu Leu His Ala Gly Asp Asn Ile
        130                 135                 140 tat ctg aag ttc aac tct aaa gac cat att cag aaa aat aac aca tac     480
Tyr Leu Lys Phe Asn Ser Lys Asp His Ile Gln Lys Asn Asn Thr Tyr
145                 150                 155                 160 tgg ggg atc atc tta atg cct gat cta cca ttc atc tct taa              522
Trp Gly Ile Ile Leu Met Pro Asp Leu Pro Phe Ile Ser
                165                 170
```

<210> SEQ ID NO 2
<211> LENGTH: 173
<212> TYPE: PRT
<213> ORGANISM: Mus musculus

<400> SEQUENCE: 2

```
Met Glu Glu Met Pro Leu Arg Glu Ser Ser Pro Gln Arg Ala Glu Arg
1               5                   10                  15

Cys Lys Lys Ser Trp Leu Leu Cys Ile Val Ala Leu Leu Leu Met Leu
                20                  25                  30

Leu Cys Ser Leu Gly Thr Leu Ile Tyr Thr Ser Leu Lys Pro Thr Ala
            35                  40                  45

Ile Glu Ser Cys Met Val Lys Phe Glu Leu Ser Ser Ser Lys Trp His
        50                  55                  60
```

```
Met Thr Ser Pro Lys Pro His Cys Val Asn Thr Thr Ser Asp Gly Lys
 65                  70                  75                  80

Leu Lys Ile Leu Gln Ser Gly Thr Tyr Leu Ile Tyr Gly Gln Val Ile
                 85                  90                  95

Pro Val Asp Lys Lys Tyr Ile Lys Asp Asn Ala Pro Phe Val Val Gln
            100                 105                 110

Ile Tyr Lys Lys Asn Asp Val Leu Gln Thr Leu Met Asn Asp Phe Gln
        115                 120                 125

Ile Leu Pro Ile Gly Gly Val Tyr Glu Leu His Ala Gly Asp Asn Ile
    130                 135                 140

Tyr Leu Lys Phe Asn Ser Lys Asp His Ile Gln Lys Asn Asn Thr Tyr
145                 150                 155                 160

Trp Gly Ile Ile Leu Met Pro Asp Leu Pro Phe Ile Ser
                165                 170

<210> SEQ ID NO 3
<211> LENGTH: 10289
<212> TYPE: DNA
<213> ORGANISM: Mus musculus

<400> SEQUENCE: 3
tcaggagaca gctataccag gctcctagct gcaagcactc acaaaccaca tgaaactcaa      60
aaagtaagac caaagtgtgg atgcttcaat ccttcctaga agggtgaaca aaatacccat     120
ggaccaaagg aaaactccac ctcctacacc cacggggcta attactataa acatgacat      180 tgcatcgttc atccatcact tgtgggtatc tgctttcccc agttctcatt ccatcagaga     240
acgagttcta gcctcatgga ggaaatgcct ttgagagagt caagtcctca agggcagag      300 aggtgcaaga agtcatggct cttgtgcata gtggctctgt tactgatgct gctctgttct     360
ttgggtacac tgatctatac ttcactcaag gtaaggtggt catagagtct acagctgcta     420
attatatcat ataaaggtta tttatttgtt agtctggtta ttatcactgc cattcagcat     480
tgctagaggt agtgggaagg aagacatttg acagtacaaa cagtgtaagc aatttaagcc     540
ttgtaatgac atggctcttc aaatgtgttt ttattcatcg aatgttttaa gacaaaagac     600
actagaaaat actatatatt ctctgtaggt gtgagctaga tagaactaca tgtttaaact     660
gagcctttag gtgtctgtgg aagttctttt gtccttcctg ggactctact agaaccttct     720
tgattggcaa agaaaagacc tgaaccatgg tactaatctt cgggtaaccc cagacaagct     780
gtagtctcat tggggaaga gatacaaaac agtaatgggg gacagtgaca ggaagcaact     840
gcatgctgag gaagggcatg gtgtcaaagt agaaaaaaag gaaatcctgg gttccagttc     900
tagattagcc tccccataac cagctgtgca aatttgagta agttgtatcg ttgttctgat     960
tctagttttt aggtctgcaa catggtgata agggaatggc tctgtttact ggcatcctg    1020 ctagctgtaa ttatagcgcg cagtaattga cctaggagaa ggataaacca tatagttgtg    1080
gtttatgagg ggaataactt tgggcttggg tgaccaggga aggcttcatg gaggagggag    1140
gagcacatgt ctgtttggga agccctgat ggttatcagg aatttcccat tgaactctag    1200
tgtaaattgt gggtctagat gggatatgaa ctggaaatgt atatcaatta ggttttctca    1260
gaagtgttct ctcatacaga acagccaggg ctgcagagag agagagagag aaaaaaaaac    1320
agcaaaaacc aaaccaaaac aaacagacaa aaaaaaaaa aaacaacaaa acaaacaaa     1380 acaaaaaaaa ccaaaaaaag cattgaccag aaaagccaga aaggaatcaa atattaaata    1440
agacattata taattcaagg gttggcctat ttatattaaa atatactaaa tcttgggcag    1500
```

```
aattaaatga cgcatagctg tgtaagaaag ggttgtgatg tgagcccagg aacatttttc    1560
taaagagacc aaccagagat ggtcttaaag gtatggttct atattggcaa gatattgaga    1620
aaagatgcag gaggaagtaa tgcactgttg attcgaggtt acttagtatg gtactggcta    1680
aagacttaca taggagccca ttaatctgta gtctgtaact gtacaaatgg atcaaaggca    1740
gagggagttc taaccccagc cccacccttc caaagaatga accaagacac gaactttctg    1800
aagcaatgag tgttgagagg actctcagca ttctcaaggg tttaaaggag gaaggctgag    1860
gatgcattaa gttcacactg aaagggcttt ttcctcaggc aaacttcctc aagtcttatt    1920
aatcaggtgg ctctgagcat cagtgagtct aggtgccgct gactcctgct ggtgaggagt    1980
ggccgaggga aatgcctttc cgagtgacat ctcttcccac aatcaaacct tggtaattca    2040
tgattgctga aactttgatt ccaggttggc ctctcaaaag aacacatccc tttcaatgaa    2100
gggttcctct tctaaacgta aaagttatcc caaatttaag gaagtaaaaa gttttggagt    2160
ctcttttcct gtcaggatgc ttggcagcgt agttactatg gaaacgacac tggctttcag    2220
ggttagcttc agtattacac ttcccttatt ggctacaaat aaatgtcttg agcagagaga    2280
tctgagtggc tggcaggtgc tgagttattg tgaggtggtt gcttccacct tttcatactt    2340
aagaacttag aagttttttt tttctttctt ttttgatgca aatctccatt tttaaaagtc    2400
tcttctaaaa aaagaagact tccctctttt tttttttttt ttttataaat aaccctctta    2460
tgtttaaaag taagatatga agcttggttt ctttcagatt ttttttttctc tctatctcct    2520 aggagacatc tagttaagag actagactgg agctcaaggc ggttggccaa ctcctccatg    2580
aaagcagctc acaaaagttg tctctgaagc atccaaatag tcaggaaagt ccctttcttc    2640
agtgaggaag ggtggaattc cagaagggaa aatggaattt gtacaattgt acttgcaaac    2700
agacggagta gattttcttt ccaaacatat gaggttagga ttagcctgga gtctgccttg    2760
gtcattctga gacaaaacaa gtcaatctgg tcttcaacca aagtgaggtt agaagaccaa    2820
ctgatccttc taaataaaag caaaactaga gtaaactgaa agctttgtat gtagcttttc    2880
gtaacatcaa ttgaattata aatagaaact gccccagtga gtcgtagggg tgagagagag    2940
agagagagag agagagtttt gaataagagt ctggttgagg atgccagcct ttcttatcag    3000
ccatatgacc ttgggcttat tacttcatca ccgtgctctc atttcctcat ctgcagaagg    3060
aacgtggtaa ttcttacaga gttgccttaa ggaataagga ggcagtaatg tgcctgaccc    3120
tcctgactca tgctaggctc tagatggctg tgattaatat ttatgccacg gttacttata    3180
aggtttacaa tgaatacaaa caacaaggtc atttaaaata tacatggctt gtctgacctc    3240
ccttcctcag taaaagacct cttctctcaa ccaaaatgat aattttccaa ttatatttta    3300
acttatggca atagttatgg atgaactcag tggcattttc taactctaaa tagatattaa    3360
agccactcga aataggcttt ctggatgctt ttctctgtca gttcatttgt ctattgattt    3420
agattttctg tgtacttctt acacatggtg atagctggaa caaaatccaa gacatttgta    3480
ttttgctggc tacttaattg cttcctatgt atgatcatgt cagtctagct agattacaaa    3540
cttcctgaga gataacaatt gtacattaaa tgtgtctttc ttgcttagaa tgctagtata    3600
atgtttggga ctataggtaat taagttgttt atttaacttg tttttataat cagcatcatt    3660
atcaaaatag ctgatatttta ctgagaagct tcaggtagcc tgtctggaga aaccctctcc    3720
aagaatcaga gtggtaaagt aagaacaaac ggtttagtga ttccccgctc ttactccctg    3780
cttaatagat aaggaaattg gaattctgga agccctgct ataaccttgt cagtctttgt    3840
gctgaactga cttttggacat ctcttttaag aaaacccaaa atgtggatga ataattgca    3900
```

```
agagtagagt gggtttcagg aaatccagtg tcttttagtt tttagagtca tggcttctcc   3960 cctttttat  tgcaccgcct tattggtata aaatgctctt attataactt ctaacatatg   4020
tatactagat agtatctcac gtctgagtat aaaaccatgt acacaaaaga tgtgtacaca   4080
cacaagatgg aaagtctaaa agtttaatac agattttccc gtctaagtct attttgcttt   4140
agttaagttg ttaagttgtc tataatatat taacattgat gcaaacataa tacagtaatt   4200
gaaatattgt ttctttggtg ctgatctctt agtcacattc agagccctag tgatttgata   4260
ttatttgttt tatttcctta attttagctt aacattttat aatacagtaa cttgagattt   4320
atattctaat ttatcttgat ttatgatttt gactgtacca attgaaaatt accttcttgg   4380
acttgatgtt cacatataat ttcatgtcta aaagcaatga atcttggcat catatatcta   4440
actacctact tgatatctaa taagcaacac aaacccacac cttcaaaagt tgtcatggtt   4500
cccctcttac tttctttcta ttagtctttc gaatttgggt aattaactta attttttca    4560 atgactgcag tcccaaatct tggagttatc tttctttat tgcattgcct catgctagta    4620
ttcatgtcag gaactccagt tacttcttgc ttccttctcc atatagccta gcttgatctg   4680
aaagtcacag ttctcctgct tcaacctaag tgctattaag acaggcgtgc atctctctgt   4740
tggaccctct gccagcacct tggtcagagc catgtgcttt ccagtttata gactccatcc   4800
agtccatgcc taactgactt cattgctttt accttctgtt ctctttgttt ttttttttt    4860 cctagcataa tagctggaaa aatcctttaa aaggatcata gatcagtctc catgcttaaa   4920
aaaagtcttt tgagcacttt gctcccagga aaccaatgca ttctcagtac ccaaaacttt   4980 aatgttggg  ccttattttt aaccctgaag catttaacag catttaagtg attgtatttg   5040
taaattagcc ataattaatg ttaccttcca gcatgtcgca gacattttga aacacttgtt   5100
tctgattctg aaggcattcc atttattata catggcctgt gattttctc tacattaaat    5160 atttctggag ctaatgctgt tgttttaagt aaagggaaaa caaagataag cagaggtccc   5220 attattttc  ccacatgcaa cagatcatct tgggaaatga ttgatgggga tatggagact   5280
gctgtttgta gtgaactaga gaggaagaac ccagcttcat cacttgcctt gtgtgtcaaa   5340
ggaaaacgaa caggatgaga caccaaagtc ttggataaaa gacaccctcc aaaaagatct   5400
gctacctttc ttctcatgat taaatctatc attccatgac accattttaa aaattaaaac   5460
aatgctgctc accacccta  ttcatgcttt cttccctttt ttaagattta tttattatat   5520
gtatgtacac tgtagcaatc ttcagacgct ccagaagaag gcgtcagagc tcgttataga   5580
tggttgtgag ccaccaggta gttgctggga tttgaactca ggacctttgg aagagcattc   5640
agtgctctta actgctgaac catctttgct gccctctctt catgctttct tttgtctctg   5700
tatacagcta aattcgtgtg tctaatatac ctctgcccac acatccttat tcacttgctt   5760
cctcatgtct tcctaaaact ctcatgtaag tcaaatgtaa aggacagaac cagtcatctg   5820
tagagggaaa tgaagaagta tgtcaggtgt acaggtgtct gtgtttgtgt gttgggagga   5880
ggggcatatt ttcggagggg gtttgggggt tggaaaatag tttgcttcag aaactttaaa   5940
ctctaagtaa ttagtcaagc atgtagcagt ggtgccatca ttctgaccag ttcttctttt   6000
ccttcaacag ccaactgcca tcgagtcctg catggttaag tttggtgagt aacccatctc   6060
ccatggtttc ctttcatttt ccttagattc tgaggcaaga aggccagtgc cagtgccctc   6120
ggaaagcccg tgcatccttt agttcacttt cagtgattgt ttattacaat tactcacccc   6180
atacttgctg tctgcccagt gagaactgag gctccagggc tgagcccgat tgacaagccc   6240
```

```
acaccaggtg acactcttgg caggcataga catcccacta acaagagcct tgtggatctg   6300
catacagcaa tcagctttta gtttggtagt ttattaagga tattttttcag attcctacaa   6360 ccttttgtca gagcatttct tatatttcat acatgtctag tgtctagtag agcatatggg   6420
aaccattact gctgttagta agtgcagaga agagaaggaa gaagcgcttc ctctttgctt   6480
ctgagtcact tttcgtgaca gtcacctgat attcgctcag aaaacatgga aaacagtgct   6540
gctgagtgtt ttagtttcat ttctgttgct tttataagat accctgtcaa aaacaactt   6600 ttggagaaaa aggatttgtt ttattcacaa gtgcaaatta tagtccctca accgtggaga   6660
aatcatggcc acaggagttt gaagcatcta gtcacattca gtcaagagca gaggaaaacg   6720
aagtgcactt gcttattgct tgcttttttt taattggata tttttatttat ttacatttca   6780 aatgttattc cctttcccga ttgccccaca gaacccccccc tttccatctc tctcccctg    6840 cttctatgag ggtgttcccc cacccaccca catactcctg cctccctgac ctcacactct   6900
cctacactga ggcatagagc cttcactgga ccaaggcct cttctcccat tgatgcccga    6960
caaggccatc ctctgctaca tatgtagttg gagccatggg tccctccatg tgtactcctt   7020
ggttagtggt ttagaccctg ggagctctgg ttggttcata ctgttgttct tgctatgggg   7080
ttgcaaatcc cttcagctct ctcattactt tctctaactc ctccattggg gacttcatga   7140
tcagttcaat ggttggcttc gagcatctgt atttgtgtat gtcaggctct ggcagagcct   7200
ctcaggaggc agttatgtca ggctcctgtt agctcagttc cttttctcta cttctttaca   7260
gttcaggaca tcttgcctag ggaatggcac caaccatagt gggctggatt ttcccatatc   7320
taataactta attaaaatac tctataagac caacttgata tagacaattc tttcttgggt   7380
cctcttctct ggtgactata gattgtgtca atttgacaag gaaagctaac taccataccg   7440
agtctcagaa tatttcttag agcacatgaa aaatatcaag tgtatacatt tgtgattgct   7500
tgtaccacat tttcatttga cactagacaa tttctttagt tcagttttttc actctcctat   7560 cttttgctcc agttttttaaa aatactttgg tccccagagg ttaggacagt ttttgaatgt   7620
gtcccactct gattttgtgt tttgtttttt cagtgaaaac aagagagtat ataatgtgtt   7680
caaatttctc cttaatgtga taaaaatcaa gtgtttttta aaattccata actgattaa    7740 ataggaaaaa atagactttc ccatggtgtg ccaccaagaa aaaatgcag agttcactgg    7800 agatgcagcg agttttttgtt ttgcttataa cactccattc ctcttgctca ttcctctatt   7860
ctcttccagc atctacctcc aagtcttatc ctagttattt tatgtgtgaa tgagaatcta   7920
agtcagtctt acctctttta ggctatgccc tctataacta aagttatgga gaattagaga   7980
aacattcaga taactttgaa tcaataaaaa cacctgttgg gggccttgaa gttacatagc   8040
tgtacaaaac cactaacatt agggaaatat ttcaatgtaa tacacaggaa aagaaatgac   8100
taaatttgta cacatatccc actttccatg tggcaatatt agacttagga tagttacaat   8160
taaatacata tatattaatt aaattaattt atagcagtaa ataattggaa ataagctaga   8220
taatgttatg ttaagttgaa agtgacacag agaatcatat tttagataca aagcatcaaa   8280
atcagaaata cagacctgtc aatcaattta gagctaatta ctgatactga gctgggaaga   8340
ttatttgaac tcagcaattt gagcccagac agcaatacag caagactccc atatcaaaat   8400
aaaagaaaag tttgttgagc acacacaatt ctgctagctt atttaggtga tgagaatata   8460
gcaattggaa aaaatggaga atacttatta tcaaagacac cacactcaag tagatgtgag   8520
acactagaaa aatggccaaa ttaattgata acatacttct tgctaacacc ttacatgaag   8580
aaaattacag caatgcagag cacggtagtc agaggagaac aatgctgagt gttgattgtc   8640
```

```
tatgtaatgt gttattggca aagcaccata gagtaaacag tatttgaata agaaagatat      8700
ggggacgcct agattataag cggttcttat tctagtcttg tgtgatttgt ctctccattc      8760
cactcccttc ctcattcata ttacctgaga tgagatacag agttattaag atctgaagcc      8820
tctcaaaaac agagagatag tttattctct caatagattc gaaatatggt ctgggaaaag      8880
tagtatatat agtccaggta aagaagccac ctgaaggcag taaaacatat agaggatgga      8940
atagtcatgg aaacatgatc ttttcttcc tcttttcaa tttcttatag aactatcatc        9000
ctcaaaatgg cacatgacat ctcccaaacc tcactgtgtg aatacgacat ctgatgggaa      9060
gctgaagata ctgcagagtg gcacatattt aatctacggc caagtgattc ctgtggataa      9120
gaaatacata aaagacaatg cccccttcgt agtacagata tataaaaga atgatgtcct       9180 acaaactcta atgaatgatt ttcaaatctt gcctatagga ggggtttatg aactgcatgc      9240
tggagataac atatatctga agttcaactc taaagaccat attcagaaaa ctaacacata      9300
ctgggggatc atcttaatgc ctgatctacc attcatctct tagagattgg gtttggtctc      9360
ctcatcttct tctttgtatc ccgagatgct ggtgggtggg ttggaggggg atgattgatg      9420
gcaatgcaca cagtttgtga gggcttacaa attgacacaa tcagagcctc ttggcatata      9480
aaattttagc cctcatatct gtctgaagag gactcagcaa atgggccaat ccctaatgtt      9540
gggtctgcaa atggacttgt acaatccatg ataaaaagga gtatgggcca cagaagacag      9600
aaactcttcc aaagaatgtc tttctaacct tgatccctgg gtagaatgag atcctgtttc      9660
catgggagtc ttacttggct tgcaaaaaag ggtgtagggc agtagcttgg ccttttttcc      9720
atcataattt ccttgagctg ttttaccta atccctccaa actctcacct tctgagagcc       9780
tcctaatgaa acattgttag actggtgggg tggccaagac atgccaacaa cacccttctt      9840
tagaggtggt gtttttagag gacagagaac attatgaagc ctagagcagc agaggtcaag      9900
atgccacgaa atggaattga tctgggaatt tttttttttt ttcattctca ggatgcaggt      9960
tcattctgaa cttttcccctа ggccttcatt gcttttgtgt gtatgtgtgc ataaattctg    10020
caaatagaaa aatgagagtt tgcaccagta ctcactagat ttaacaccag aaagtggtac     10080
ttttctggct gtattatgcc atgatagcac attttctgtt ggtgttccct aactgacaag     10140
tataacagtt ttcctaaacc acacaacaat gctatgatgt taatgggta gatattttg       10200 gaaaaaaatt gcacagtgag aacatgggta gatgaaccct aagactctta cctcaattca    10260
gaactcgcaa ggagttaagt gagtgggt                                        10289

<210> SEQ ID NO 4
<211> LENGTH: 22
<212> TYPE: DNA
<213> ORGANISM: Artificial
<220> FEATURE:
<223> OTHER INFORMATION: Mus musculus GITRL forward PCR primer

<400> SEQUENCE: 4
atggaggaaa tgcctttgag ag                                                 22

<210> SEQ ID NO 5
<211> LENGTH: 25
<212> TYPE: DNA
<213> ORGANISM: Artificial
<220> FEATURE:
<223> OTHER INFORMATION: Mus musculus GITRL reverse PCR primer

<400> SEQUENCE: 5
```

```
gaatggtaga tcaggcatta agatg                                              25

<210> SEQ ID NO 6
<211> LENGTH: 39
<212> TYPE: DNA
<213> ORGANISM: Artificial
<220> FEATURE:
<223> OTHER INFORMATION: Mus musculus GITRL forward PCR primer
      containing SalI site

<400> SEQUENCE: 6
tttaaagtcg acccaccatg gaggaaatgc ctttgagag                               39

<210> SEQ ID NO 7
<211> LENGTH: 42
<212> TYPE: DNA
<213> ORGANISM: Artificial
<220> FEATURE:
<223> OTHER INFORMATION: Mus musculus GITRL reverse PCR primer
      containing EcoRI site

<400> SEQUENCE: 7
tttaaagaat tctcattaag agatgaatgg tagatcaggc at                           42

<210> SEQ ID NO 8
<211> LENGTH: 534
<212> TYPE: DNA
<213> ORGANISM: Homo sapiens
<220> FEATURE:
<221> NAME/KEY: CDS
<222> LOCATION: (1)..(534)

<400> SEQUENCE: 8
```

| | | | | | | | | | | | | | | | | |
|---|---|---|---|---|---|---|---|---|---|---|---|---|---|---|---|---|
| atg | tgt | ttg | agc | cac | ttg | gaa | aat | atg | cct | tta | agc | cat | tca | aga | act | 48 |
| Met | Cys | Leu | Ser | His | Leu | Glu | Asn | Met | Pro | Leu | Ser | His | Ser | Arg | Thr | |
| 1 | | | | 5 | | | | | 10 | | | | | 15 | | |
| caa | gga | gct | cag | aga | tca | tcc | tgg | aag | ctg | tgg | ctc | ttt | tgc | tca | ata | 96 |
| Gln | Gly | Ala | Gln | Arg | Ser | Ser | Trp | Lys | Leu | Trp | Leu | Phe | Cys | Ser | Ile | |
| | | | 20 | | | | | 25 | | | | | 30 | | | |
| gtt | atg | ttg | cta | ttt | ctt | tgc | tcc | ttc | agt | tgg | cta | atc | ttt | att | ttt | 144 |
| Val | Met | Leu | Leu | Phe | Leu | Cys | Ser | Phe | Ser | Trp | Leu | Ile | Phe | Ile | Phe | |
| | | 35 | | | | | 40 | | | | | 45 | | | | |
| ctc | caa | tta | gag | act | gct | aag | gag | ccc | tgt | atg | gct | aag | ttt | gga | cca | 192 |
| Leu | Gln | Leu | Glu | Thr | Ala | Lys | Glu | Pro | Cys | Met | Ala | Lys | Phe | Gly | Pro | |
| | 50 | | | | | 55 | | | | | 60 | | | | | |
| tta | ccc | tca | aaa | tgg | caa | atg | gca | tct | tct | gaa | cct | cct | tgc | gtg | aat | 240 |
| Leu | Pro | Ser | Lys | Trp | Gln | Met | Ala | Ser | Ser | Glu | Pro | Pro | Cys | Val | Asn | |
| 65 | | | | | 70 | | | | | 75 | | | | | 80 | |
| aag | gtg | tct | gac | tgg | aag | ctg | gag | ata | ctt | cag | aat | ggc | tta | tat | tta | 288 |
| Lys | Val | Ser | Asp | Trp | Lys | Leu | Glu | Ile | Leu | Gln | Asn | Gly | Leu | Tyr | Leu | |
| | | | | 85 | | | | | 90 | | | | | 95 | | |
| att | tat | ggc | caa | gtg | gct | ccc | aat | gca | aac | tac | aat | gat | gta | gct | cct | 336 |
| Ile | Tyr | Gly | Gln | Val | Ala | Pro | Asn | Ala | Asn | Tyr | Asn | Asp | Val | Ala | Pro | |
| | | | 100 | | | | | 105 | | | | | 110 | | | |
| ttt | gag | gtg | cgg | ctg | tat | aaa | aac | aaa | gac | atg | ata | caa | act | cta | aca | 384 |
| Phe | Glu | Val | Arg | Leu | Tyr | Lys | Asn | Lys | Asp | Met | Ile | Gln | Thr | Leu | Thr | |
| | | 115 | | | | | 120 | | | | | 125 | | | | |
| aac | aaa | tct | aaa | atc | caa | aat | gta | gga | ggg | act | tat | gaa | ttg | cat | gtt | 432 |
| Asn | Lys | Ser | Lys | Ile | Gln | Asn | Val | Gly | Gly | Thr | Tyr | Glu | Leu | His | Val | |
| | 130 | | | | | 135 | | | | | 140 | | | | | |
| ggg | gac | acc | ata | gac | ttg | ata | ttc | aac | tct | gag | cat | cag | gtt | cta | aaa | 480 |
| Gly | Asp | Thr | Ile | Asp | Leu | Ile | Phe | Asn | Ser | Glu | His | Gln | Val | Leu | Lys | |
| 145 | | | | | 150 | | | | | 155 | | | | | 160 | |

```
aat aat aca tac tgg ggt atc att tta cta gca aat ccc caa ttc atc    528
Asn Asn Thr Tyr Trp Gly Ile Ile Leu Leu Ala Asn Pro Gln Phe Ile
            165                 170                 175 tcc tag                                                            534
Ser
```

<210> SEQ ID NO 9
<211> LENGTH: 177
<212> TYPE: PRT
<213> ORGANISM: Homo sapiens

<400> SEQUENCE: 9

```
Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
        35                  40                  45

Leu Gln Leu Glu Thr Ala Lys Glu Pro Cys Met Ala Lys Phe Gly Pro
    50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu
                85                  90                  95

Ile Tyr Gly Gln Val Ala Pro Asn Ala Asn Tyr Asn Asp Val Ala Pro
            100                 105                 110

Phe Glu Val Arg Leu Tyr Lys Asn Lys Asp Met Ile Gln Thr Leu Thr
        115                 120                 125

Asn Lys Ser Lys Ile Gln Asn Val Gly Gly Thr Tyr Glu Leu His Val
    130                 135                 140

Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser
```

<210> SEQ ID NO 10
<211> LENGTH: 10331
<212> TYPE: DNA
<213> ORGANISM: Homo sapiens

<400> SEQUENCE: 10

```
attaatctca aactttattt tttcttataa aaagtgattt tcttatctag aaataatctg     60
gaatactttc ttagatgaga gcacaccact ttattctccc aagcctcctc tacacgtgca    120
ctgtactgcc gtttgattta ggaaagaaat tttttttccc tctgaacttc ccttgtgctt    180 tttttttat gttctgagtt tgtgttggct ttcagccttc cgttccttt gttgtatttg     240 atctggtgcc aaatgagagt cagcacttaa gttataagta tcattttcta acacagtgac    300
agaaggaaaa ctccgccttc cacacccact actaattacc atattgctac aaaacatgac    360
attgcatcct tcacccatca cttgtgaatt tttgttttcc acagctctca tttctccaaa    420
aatgtgtttg agccacttgg aaaatatgcc tttaagccat tcaagaactc aaggagctca    480
gagatcatcc tggaagctgt ggctcttttg ctcaatagtt atgttgctat tctttgctc    540 cttcagttgg ctaatcttta ttttctcca attgaggta aggaggcaat tgtacctaag    600
gttactattt gctataatcc tctatttatt tgttttttcta gttgttatca ttgtcactca    660
```

```
gtattgttag caatagttgg aaggaagaga tgtgtataca aatgtaaat acaattctaa      720 tattgtcatg acatggcgtt tgaagtttat ctaaaggttt tgagataaaa ggtatcagaa      780
aatgctaaat gttagctgca gaactctgtt agatagagag aactggttaa gccaattgac      840
aggggcctgt ggagtatttt tccttccctc tgctatagct cttggtggaa taaaaaggt      900 aaaaatatga atgaatatca aggaatggga tgcaagctat agtcttattt atggaaaaga      960
cttaaaaaaa tagtgaaaga caggattaag taaatgacag gtggtttgtg tgtctttgag     1020
gagggaagtg gccctgagct aggtgtaaga agatctggat tctggttctg ggtctcctaa     1080
taaccagctg tataaatttg ataaagacat ttaatctctc tagtttgcag cttctttatc     1140
taaaaaaact ggtggtaggg gaatggattt attatgatgt ttcttctagc tataaaatgt     1200
catgatcaag aatttattta agggtagtat gaagaataaa tgcctaagtc actcaaaagc     1260
agggaacaat gactttagat tgagttgatc agggaagact tcatggagga atgagaaagc     1320
ccatatctat ttgggaagcc cctgatgctt gtcaggaatt tcccattgag atgcaggcca     1380
agctgtgggc ctagagaatg ggatggtaca ctgggaatgg agattagttt tgttcttac      1440 taaaaaatct ttcctcacag ttaactacgt agcactgatc aaaagaaaa taagaaatgc     1500 tttatttatt tcaggattta gcctatttct ggctaaattt gaagactcta gttttgggg      1560 agaataaagt ggcatatgtc catctgagaa agagttgaaa tgtgactgca gaaacacttt     1620
tcttaaggga actgaccagc aaagatttca aagatatagt tctaccactt aagataagta     1680
aaagtaattg agaaaagatg caggaggaag cagtccccta ttgatattaa tttagagtag     1740
gtatagcttt ggccaatttt tccacagtag cccattaatt tgtattccat aactgtatac     1800
aaggcttatg tgcaacagag gcatttctaa ttacaaccct gctctctcaa gaaatgtatg     1860
aagcagaagt gtgaactttc tgggtcagtg aagttgaaag aaagaattgt cagaaattct     1920
tagtgtctag atttctgaag aagaggaagg gtgagaatag caataactta aatttggaag     1980
tgcttctttc ttctaaaaat tataagatta attagccaga taaccctgaa gaacactgaa     2040
tataagcatc atcagttcct acatatgact caggaatgaa tacacagaag cctttcccaa     2100
aggcacccag cagttcttgc aaagggaaag agaaagtcta ataatgccag atcatctggg     2160
acacctctct tcagaatcaa actggattaa tcccatgtgt ttgagctctg attctggttt     2220
ctctctccta gatccagttt ctcaatgaaa tgttctacct ctaaagataa cccagagttt     2280
gtttcaaatt tggggaagta taaaatgttt ttagaatatt gttctgacag gacacttgca     2340
ggatttgttt ctatgggaaa agccagtggc ctggccaacc atacatgata ttagcttctg     2400
catttcactt tccacttacc tgtacttccc tttccctatt ggccacaaat aaatatctct     2460
ggaaaagaag tctgagaggc tggcagatag tgattcatta tgatgtggcc acttccacat     2520
tgtcacaata cccatgaacc gtgaagtttt attttggtct ccactctagt ttttacatac     2580
aaagtcccac tttccagatt gtctagacac tactttaaaa agtgtacact taaaagaaag     2640
tgtaacactt taaaaagtgt tagatgggaa gcttggctcc ttgggtcaat ttttttcttt     2700
ttttctctct tctttgagaa aatatttaac taaaaggata gctgtgagtc caaggagttt     2760
ggtcaatccc tcagtgaaaa taatctcaca ggaattatca ctaagaaatc aaatgttcag     2820
cagagtctga acttcagcaa aatgaaggat actttcagaa ggggaagttg tacttatact     2880
taaaagcaga gcagattttta tttttcactga tgatttgatt agggttggtt tggagagaga     2940
atgattgttt tggccatttt gagccgaact acgtaaatct agccttaaat caagaagagg     3000
```

```
ttacaaaagc aactgatcct tctaagcaaa aataacgaac ccatatgtgt ctttaaaagt    3060
gggtatttac tacttccaaa catcagcaga attataaata gaaacttacc ccacagagtg    3120
gtagaggtga gagtgttgac ccagacaggc tgggtgtaga tctcattctt gccttttatt    3180
ggctgcatga ccttaggcta gttacttaat ccctctcatc ctcatttcct catctgcaaa    3240
atgagcaacc taattttttgt agagttgtgc taaggattaa tgagacagta gagtatctga   3300
cataaagtag ctcccagtag aggggagtga ttaatatttg ccccattact attaatgaga    3360
taataatggg caaaaattta acaagaccat ttaacaatat ggatagtctt tgcctaccta    3420
tatcactctc tcaatcaaac actatatctc agagccaaat ttatgatttt gcaattagat    3480 ggattttttag tggtggcaat aattagagag tatcacagtg atggtctctg tagcgctaaa   3540
tagacataaa gcagcctgca gtatattata cggaatttct gactctggaa attagtttgg    3600
acttaggttg tctatagctt aggtttctct gagcacatct catacatgct agtagatggt    3660
gcagatacta tctgtggcac gtattttggc actcattcat atttagattg ttaccaaatt    3720
gctttgggtg tgtaatcatg tctttctaga aagattataa acttcttgag aagcaaggac    3780
caaaaattac atttgtttct catgcttaca atgctgtaca atgttggaaa tatggatgct    3840
taaattgtag ttcaattctt cattacaatc accatcatca cccaaacagc taatatttat    3900
tgaacaggtc caggcaggat atctaggcaa agcccttatt aaaaacgacc tcatttaacc    3960
ccaacaactt caacaagcta ggtgctatta tttctcccat tttatagatg aggaaattgg    4020
ggttaaggga gtcttttgtca cgtccctatc atgggttgaa ctaaattgaa tttcaacatc    4080
tcctccagga aacaccaaaa tgaggatgaa ataattgcaa gaggccaggc acagtggctc    4140
acgcctataa tcccagcact tgggaggct gaggcgggta gattgcttga ggtcaagagt     4200
ttgagaccag cctgggcaac atggcaaaac cctgtctcta caaaaaaata caaaaaaat     4260 agctgggctt ggtggcatgc acctgtagtc ccagctactc aggggggctga cgtgggagaa   4320 ttggttgagt ccaggaggat gaggctgtag tgaactgaga taacaccact gcactccagc    4380
ctgggcaacg gaatgagacc ctgtctcaaa aacaacaac aacaacaaca acaacaaaaa     4440
aaaacaagtg tagggaatca aaaaatttat ttcctagaat agtggctttc agactttta     4500 attgcacctc cctttcaata acatattatc agtataattc ccaacatttg tatgctaatt    4560
attatactat atacaagtac taataatatg tacactaaag agatacacaa aatatatatt    4620
tataagggtg agccaaataa tatattcaat gtaactctca caatgcaaaa ccattttgct    4680
ttcaccaaaa tgttatattt tctataatca ttaatatgtc ataaacatta ctaaaataag    4740
taaaatattt taataacgtg gtgaatgcat ttattttatt ttttaatctg agcttaacac    4800
tatgtgatac agcaatttga agtttgatat gttaatttac cttgtttcat gattttgacc    4860
atcatgactg aaaaattacc cgacaaacaa atatagatta aaatggaaga acacatcttt    4920
ggatattctt atcatgtcat accacttaat tttcaatcca tcattcaatg atggatgcct    4980
ctctttcctt ccttccacaa ctaaattcca agatctatag ctttaacacc tccctcgcat    5040
aaactcactc acttgcttct ctctatcttc attatactct aatgacaaaa gctcgactat    5100
ggaaaacctc caatgctgat taaatccaac tgctctgtct ctttcactgt tgaatatatc    5160
tgaagaaaaa cataaaattt tttgaaaggt cttactttaa attcacagcc actgccttca    5220
agtggatttc attgttgctc tggaaacagc ccatgtttcc ccagtccatt cactctcctc    5280
tactggatga tttcatacct ttagcttctc ttcaaacatc taataactct tccccattct    5340
cactctccac tgataacgtt gcctccatat tttaagagaa aatagaagta cggaggaaag    5400
```

```
aagttccaat atcaacaact cattggcatt tgtgtccagg tatactgtta ttctgtcttg   5460
tcactatgga taaattgtcc atgcatctat ccaagccatc tatgaactaa atcttatcct   5520
ctcttgccta ctcagggaca ttgctgcaac agttctctcc tcgctcttac atattatgcc   5580
tcatccattt tacagaaaca tttccatcaa atggaaatag aaaaacgtgt tgtcatttct   5640
ctcacattaa aacgtaacaa caacaacaac aacaacaaca acaaaaaacc tctttgatct   5700
ctcatcctca tccaaactcc actcattttt ttctgctctc cctacagcaa aattcctcca   5760
acttctcttg tcccatttac ccttaaattt attttaacta agcttctgcc ctcttcacat   5820
atcacagaaa ctaattttgt caagaactcc agtgactacc atgttgctca atctatcagt   5880
caattcactg tactcttctt acttgatcta tcaacagcat ttgacaccag ctgatcactc   5940
gtccttcatg aaatactttc ttttcttggc ttccaaacat cagactctcc tagtttcctt   6000
tcagactcag cttttccttt ctattgtccc ttgcttgttc tttctcattc tccgacctct   6060
aaacatcaca acgccccagt gttcctctcc atctacaccc actaacatga tggcctcata   6120
caatctcaca gcttaaaaca tcaactatga gcttaagact cttaaatgta tatcaccaga   6180
gctccttaaa tttcagcctg cttgacacac ttacttggat ttataataag catcacaaac   6240
taatatgtcc acaaccaaac tcatcattgt tcccctcccc atttattcct cttacatctt   6300
atccatttta gtgaataaca actttatctt tccaattatg caggcctaaa atactggagt   6360
catctttgtt tcttctcatt ccctaccccca tatccatgtc aggaacttct gttggctcta   6420
ttttccaacc aagtatcacc atctacagag ctagcacctt ggtcagagac accatgctct   6480
cttgcctaga tgaatgactg taatgatctc ttagctagtc tcactacatt tgcccttgcc   6540
tctgtttaat ttgttcctag catagcagcc agagaaatcc tacaaaagga aagtgtgcaa   6600
cacgtttaag ttcaaaaagt cttttaagca ctttgccatt aggaaaccaa taacctttgg   6660
gtgatacaaa aaatgtttgt ggttatgcct gaatttacta caacgtattt ttgagcattt   6720
agcattaact acttgtgttt gtaaaattaa ccacacactg atggcatctt gtagcatgtg   6780
aactgccgta cattgcagta gtctgaaact tggaactgtt tttcagggta tctcagatac   6840
tgtatatgac atgtagttat ctgaatatta tacatgggtg gtttcatcaa tctgagttgt   6900
aaatatttct agggcttaat ttactgtttt aaataaaata aacataaata gaagcttcac   6960
tattttcctt tcacatgcca acagatcacc ttgtgcagtc actgggtgt ggaaactgct   7020 attttgttga aaactttta gagcccaagg ttgggggggg ggtccgatat caaatagttg   7080
tcctgtaggt atagattagg taatggaatg agatcttgac cttttgtctaa aagacctaaa   7140 agggaagcta ggtaataaaa ggtaaaggat ggagccactc aactttaaag ggaggctgag   7200
agggctgaga catggtgaag ggaaggattt ttttttatggt tatagaacac tagtttgctt   7260
caggaattca aagctctaaa taaatcaatc aaaaaaatta atgacactgt catcatccta   7320
atcaattcat cttttatttc cccaacagac tgctaaggag ccctgtatgg ctaagtttgg   7380
tgagtaacct atcttgcatg tcttttactt ttccttagttt ttgatgcaag aaggcaggtg   7440
tcagtgatct caagaaaacc tgtatttttct tttattcatt tctgagctac tatgtataat   7500
tacttatcat gtactgggca gttgcccaag agctgaggct ttcagaggta aaccaggcaa   7560
aagaagccca tgccctgata aagcttatgt tgaaggctgc atctctggcc aggaatgagc   7620
atctctctta ctggcctatg aatctgagat ccgggaatct cctttttaatt ctgtgtttta   7680 ataaacacaa caagttcag atttctacaa cctttcctta aagtctttct catgtttcac   7740
```

```
atattgctaa tgtccaatgg agtatgtgag agagtgccat tgttgtttct aaatgtatag    7800
aagagcaatg agagttggaa aagtggccac ttcctctact attttctctt ctaagcttag    7860
cttctgagtc attttccctt gtggtcacct gatatttgct tagaaaacac accagtttac    7920
agttacactg agccttagat tcttagaata catggaaaat ttcagataaa tacattttt     7980
ttaaagttgt ttataggttt caggccaaac atacattttc agttgagaac agaccatttc    8040
tagagttaac tctgcaaccc ctgtgttcct atatagttta aaccagtagg tttccttggc    8100
ttgtgggaat tagaaaatgt ccttttgcct gtctctttct ttgtgttttg ttttttgtttt   8160
gcccataagt ggaatggaat gcatggcatg tgtgaaatta tgccttgatg tggtaaaagt    8220
tgagaaactc aagtgatgct aaggtggtct ttaaatgacc cctttcaca gaattaaatg     8280
ggagaaccaa tgacacttct tcctggtgac ctgcctattg cctattacat gtcaaggaag    8340
aagaaattta ctgggctccg agctcattgg cgatactggg tggctttgtc ttttgttcta   8400
gtgatcgctc tttcattctc ctccagaatc taccttcaga gtcttatatt agtcattcat    8460
atgaatgagc attgaagtaa aaatgttacc tcttccaggg tgtttcctca tcaagttttc    8520
tttttaatta tgggacaaag gacaaaaatt atggagaatt gcagaacaga taagcattct    8580
gggtggtaaa agcacctccc ggggctgtga gatcacactg ctgtgcaaaa ccaagtaatg    8640
ttaggcaaac atctaagttt catatgtgct aatgaaaatg aatgattagg tctttacctt    8700
ttctttacca tttgggacag tattgcacta gggatcctta tatttaaata gtcaagttat    8760
ttctatttat aaactcataa atttacaatt agctatttt gggggattta tttaatgaat     8820
cctaagtagg tcttaaatga tatataccta caaactgagg agaacagcca taatttagac    8880
acaaagcacc taattcagga acatggaagt atcattcaat caataaatat ttatggaaca    8940
tctaccaggt accagggact ttttcaggtg ctgaaaatac aagaatgaac aaaatagaga    9000
tatatttgtc ctaaaaaatt ttacattcaa agtgatacaa gatggacaat aaacaaatga    9060
acaatttagt ttataacatc ctagacactg acacacttta tgaagaaaac tcaagcaagg    9120
taaaatgagg gaatgatagg agaacacttt ttaatatagc ataattaagg aaagccacac    9180
tgataaagtg ataaacagcc agtggtattt acaccgaaaa tgcctggaaa ggcatggact    9240
gccaaccctg gttttcaaaa ttttggcttg tgatttctttt ctccattagt cttttcttct   9300
cctttctttt tcccacaaat attaatcaac aagagatgcg aagtcactta agtcattttt    9360
ctattccaaa ttcttttcct tagaattctt gctccaagca agaaatactc tttggatttg    9420
caatttctct aaaacaagga gtagataggt acttaaaata gaaaaattct gcttgaagag    9480
aactagtgta gatcaggtaa agaaacaaca tgtatgtggt aaataattaa ctacaatctg    9540
gaaaaggatg aaataatgaa ataactatgc tttcatcttt tttatccttg tatatttctt    9600
ataggaccat taccctcaaa atggcaaatg gcatcttctg aacctccttg cgtgaataag    9660
gtgtctgact ggaagctgga gatacttcag aatggcttat atttaattta tggccaagtg   9720
gctcccaatg caaactacaa tgatgtagct ccttttgagg tgcggctgta taaaaacaaa   9780
gacatgatac aaactctaac aaacaaatct aaaatccaaa atgtaggagg acttatgaa    9840
ttgcatgttg gggacaccat agacttgata ttcaactctg agcatcaggt tctaaaaaat   9900
aatacatact ggggtatcat tttactagca aatccccaat tcatctccta gagacttgat   9960
ttgatctcct cattcccttc agcacatgta gaggtgccag tgggtggatt ggagggagaa   10020
gatattcaat ttctagagtt tgtctgtcta caaaaatcaa cacaaacaga actcctctgc   10080
acgtgaattt tcatctatca tgcctatctg aaagagactc aggggaagag ccaaagactt   10140
```

```
ttggttggat ctgcagagat acttcattaa tccatgataa aacaaatatg gatgacagag   10200
gacatgtgct tttcaaagaa tctttatcta attcttgaat tcatgagtgg aaaaatggag   10260
ttctattccc atggaagatt tacctggtat gcaaaaagga tctggggcag tagcctggct   10320
ttgttctcat a                                                        10331
```

```
<210> SEQ ID NO 11
<211> LENGTH: 21
<212> TYPE: PRT
<213> ORGANISM: Apis mellifera

<400> SEQUENCE: 11

Met Lys Phe Leu Val Asn Val Ala Leu Val Phe Met Val Val Tyr Ile
1               5                   10                  15

Ser Tyr Ile Tyr Ala
            20

<210> SEQ ID NO 12
<211> LENGTH: 13
<212> TYPE: PRT
<213> ORGANISM: artificial
<220> FEATURE:
<223> OTHER INFORMATION: synthesized PLP peptide

<400> SEQUENCE: 12

His Ser Leu Gly Lys Trp Leu Gly His Pro Asp Lys Phe
1               5                   10
```